United States Patent [19]

Rubenstein et al.

[11] 4,067,774
[45] Jan. 10, 1978

[54] COMPOUNDS FOR ENZYME AMPLIFICATION ASSAY

[75] Inventors: Kenneth E. Rubenstein, Palo Alto; Edwin F. Ullman, Atherton, both of Calif.

[73] Assignee: Syva Company, Palo Alto, Calif.

[21] Appl. No.: 722,964

[22] Filed: Sept. 13, 1976

Related U.S. Application Data

[60] Continuation of Ser. No. 481,022, June 20, 1974, abandoned, which is a division of Ser. No. 304,157, Nov. 6, 1972, Pat. No. 3,852,157, which is a continuation-in-part of Ser. No. 143,609, May 14, 1971, abandoned.

[51] Int. Cl.$^2$ .............................................. C07G 7/02
[52] U.S. Cl. ...................................................... 195/63
[58] Field of Search ........................... 195/63, DIG. 11

[56] References Cited
U.S. PATENT DOCUMENTS 3,878,187 4/1975 Schneider et al. ..................... 195/63

*Primary Examiner*—Alvin E. Tanenholtz
*Attorney, Agent, or Firm*—Townsend and Townsend

[57] ABSTRACT

Novel biological assay method for determining the presence of a specific organic material by employing a modified enzyme for amplification. By employing receptors specific for one or a group of materials (hereinafter referred to as "ligands") and binding an enzyme to the ligand or ligand counterfeit to provide an "enzyme-bound-ligand", an extremely sensitive method is provided for assaying for ligands. The receptor when bound to the enzyme-bound-ligand substantially inhibits enzymatic activity, providing for different catalytic efficiencies of enzyme-bound-ligand and enzyme-bound-ligand combined with receptor.

The receptor, ligand and enzyme-bound-ligand are combined in an arbitrary order and the effect of the presence of ligand on enzymatic activity determined. Various protocols may be used for assaying for enzymatic activity and relating the result to the amount of ligand present.

8 Claims, No Drawings

COMPOUNDS FOR ENZYME AMPLIFICATION ASSAY

CROSS REFERENCE TO RELATED APPLICATION

This application is a continuation, of application Ser. No. 481,022, filed June 20, 1974, now abandoned which is a division of application Ser. No. 304,157, filed Nov. 6, 1972 now U.S. Pat. No. 3,852,157 which is a Continuation-in-Part of Application Ser. No. 143,609, filed May 14, 1971, now abandoned.

BACKGROUND OF THE INVENTION

1. Field of the Invention

There is a continually pressing need for rapid, accurate qualitative and quantitative determinations of biologically active substances at extremely low concentrations. The purpose of the determination can be extremely varied. Today, there is a wide need for determining the presence of drugs or narcotics in body fluids, such as saliva, blood or urine. In addition, in medical diagnosis, it is frequently important to know the presence of various substances which are synthesized naturally by the body or ingested. These include hormones, both steroidal and polypeptides, prostaglandins, toxins, as well as other materials which may be involved in body functions. Frequently, one is concerned with extremely small amounts and occassionally, with very small differences in concentrations.

To meet these needs, a number of ways have been devised for analyzing for trace amounts of materials. A common method is to use thin layer chromatography (TLC). By determining the flow factors and using specific reagents, the presence of certain materials can be detected; in many instances, the particular material can be isolated and identified quantitatively, for example, by mass spectroscopy or gas phase chromatography. However, thin layer chromatography has a number of deficiencies in being slow, requiring a high degree of proficiency in its being carried out, being subject to a wide range of interfering materials, and suffering from severe fluctuations in reliability. Therefore, the absence of satisfactory alternatives has resulted in intensive research efforts to determine improved methods of separation and identification.

An alternative to thin layer chromatography has been radioimmunoassay. Here, antibodies are employed for specific haptens or antigens. A radioactive analog employing a radioactive atom of high flux is used and bound to the antigen. By mixing an antibody with solutions of the hapten or antigen and the radioactive hapten or antigen analog, the radioactive analog will be prevented from bonding to the antibody in an amount directly related to the concentration of the hapten or antigen in the solution. By then separating the free radioactive analog from the antibody bound radioactive analog and determining the radioactivity of the separate components, one can determine the amount of hapten or antigen in the original solution.

The use of radioactive materials is not desirable for a variety of reasons. First, radioactivity creates handling problems and undesirable hazards. Secondly, the preparation of such compounds involves similar hazards, greatly enhanced by the much larger amounts of radioactive materials which are present. Because of their instability, the radioactive materials have only a short life. In addition, the use of radioactive materials requires a license from the Atomic Energy Commission, subjecting the licensee to review by the Commission as to the maintenance of minimum operating standards. These standards may change from time to time, so as to involve added expense and inconvenience to the licensee. Finally, the separation of the bound and unbound radioactive analog is difficult and subject to error. See, for example, Abraham, Prelim. Comm., 29, 866 (1969).

Besides the aforementioned materials, assays at extremely low concentrations would be desirable for a variety of pesticides, such as insecticides, bactericides, fungicides, etc., as well as other organic pollutants, both in the air and water. Organic pollutants may be assayed whenever a receptor can be devised and the pollutant is inert to the reagents employed.

2. Description of the Prior Art

Use of radioimmunoassay is described in two articles by Murphy, J. Clin. Endocr. 27, 973 (1967); ibid., 28, 343 (1968). The use of peroxidase as a marker in an immunochemical determination of antigens and antibodies is found in Stanislawski et al, C. R. Acad. Sci. Ser. D. 1970, 271 (16), 1442-5. (C.A. 74 1144 B). See also, Nakane, et al, J. Histochem. and Cytochem. 14, 929 (1967) and Avrameas, Int. Rev. of Cytology, 27, 349 (1970). A general description of thin layer chromatography for assay may be found in Stahl, Thin Layer Chromatography, Springer Verlag, New York, 1969. See also, Peron, et al, Immunologic Methods in Steroid Determination, Appleton, Century Crofts, New York, 1970.

Also of interest are publications by Van Weemen, et al, FEBS Letters 14, 232 (1971), and Engvall, et al, Immunochemistry, 8, 871 (1971) concerned with immunoassays employing enzymes. See also U.S. Pat. No. 3,654,090. See also, Cinader, Proceedings of the Second Meeting of the Foundation of European Biochemical Societies, Pergamon, Oxford, 1967, vol. II chapter four.

SUMARY OF THE INVENTION

Detection of ligands is obtained at extremely low concentrations by using specific receptor sites for the ligand and enzyme amplification of ligand displacement. By bonding a ligand or a ligand counterfeit to an enzyme while retaining enzymatic activity and then combining the enzyme-bound-ligand to a receptor for the ligand, the presence and amount of ligand in an unknown solution may be readily determined. By competition for receptor sites between the enzyme-bound-ligand and the free ligand, the two ligand moieties being added to the receptor simultaneously or sequentially, the difference in enzymatic activity resulting from the presence or absence of ligand may be determined in accordance with a particular analytical scheme. This difference will be related to the amount of ligand present in the unknown solution. Enzymatic activity is easily determined in known ways by following the change in concentration of an enzyme substrate or product of the substrate by standard techniques.

DESCRIPTION OF THE SPECIFIC EMBODIMENTS

This invention provides a method for detecting or assaying extremely low concentrations of a wide range of organic materials by relating the presence of a particular unknown to enzymatic activity. An amplification is obtained by having a large number of molecules formed or transformed as a result of the presence of one molecule. This amplification is achieved by bonding the compound to be assayed or a counterfeit of the compound to an enzyme. This assemblage is referred to as an enzyme-bound-ligand. The particular molecule to be assayed is referred to as a ligand. The ligand analog will include either a ligand which is modified by replacing a proton with a linking group to bond to the enzyme or a ligand counterfeit which is a ligand modified by other than simple replacement of a proton to provide a linking site to the enzyme. The ligand and the enzyme-bound-ligand are both capable of binding in a competitive fashion to specific receptor sites. It should also be noted that other compounds of very similar structure may serve as ligands capable of competing for these sites, e.g., morphine glucuronide and codeine will compete with enzyme-bound-morphine for binding to certain types of morphine antibodies. In most instances, this is advantageous in permitting one to assay for a class of physiologically closely related compounds.

Various methods or protocols may be employed in assaying for a wide variety of ligands. Normally, the ligand, enzyme-bound-ligand and receptor will be soluble in the medium employed. The substrate(s) for the enzyme may or may not be soluble in the medium. In some situations it may be desirable to provide a synthetic substrate which is not soluble or employ an insoluble natural substrate.

In carrying out the assay, the enzyme-bound-ligand is combined with a high molecular weight receptor which results in inhibition of enzymatic activity. When a ligand and enzyme-bound-ligand are introduced into a solution containing ligand receptor, the enzymatic activity of the solution after the three substances are combined will be affected by the concentration of the ligand present in the solution. That is, the enzyme-bound-ligand and the ligand will compete for the receptor sites. The number of enzyme-bound-ligand molecules not inhibited by the receptor will be directly related to the number of ligand molecules present in the solution. One can achieve this in two ways: (1) either by competition, whereby the enzyme-bound-ligand and ligand are introduced to the receptor substantially simultaneously; or (2) the enzyme-bound-ligand or ligand may be first added to the receptor, and the system allowed to come to equilibrium, and then the ligand added or enzyme-bound-ligand added respectively, in effect, to displace the material originally added from the receptor. Since the enzymatic activity will be diminished or inhibited when the enzyme-bound-ligand is bound to the receptor, the enzymatic activity of the solution will be directly related to the amount of ligand present in the solution.

The assay can be carried out, either by considering the effect of ligand on the rate at which enzyme-bound-ligand binds to receptor or the effect of ligand on the equilibrium between the reagents: enzyme-bound-ligand and receptor. Where enzyme-bound-ligand and ligand are present with receptor, one need not wait until equilibrium is achieved between the three species. If one measures the enzymatic activity at a specific time or interval of time from the time of combination of the three species, the enzymatic activity of the assay mixture will be a function of the effect of the ligand on the rate of binding of the enzyme-bound-ligand to the receptor. By determining standards under the same conditions, including the same time interval, employing different concentrations of ligand, a smooth standard curve is obtained.

By measuring the effect of the ligand on rate of binding, rather than the effect on equilibrium, a shorter time interval between the time of combining the reagents and unknown suspected of containing the ligand and the time for the determination will be involved, as compared with waiting until equilibrium is achieved. It is frequently found that reproducible values can be obtained in from 0.1 to 5 minutes after combining the reagents and unknown. The rate of enzymatic activity is usually determined over a short time interval, e.g., 1 minute. The time interval can be the second, third, etc. minute from the time when the reagents and unknown were combined.

The concentrations of the reagents: the enzyme-bound-ligand and the receptor, may be varied widely. Normally, the concentration of receptor (based on active sites) and enzyme-bound-ligand will be from about $10^{-4}$ to $10^{-14}$ M, more usually from $10^{-6}$ to $10^{-12}$ M. The lower limit for the concentration of enzyme-bound-ligand is predicated on the minimum amount which can be detected. This will vary with different enzymes as well as different detection systems.

The amount of receptor employed is normally calculated based on receptor sites and will vary with the concentration of enzyme-bound-ligand, the ratio of ligand to enzyme in the enzyme-bound-ligand, and the affinity of the receptor for the ligand. Usually, there will be at least 1 active receptor site per molecule of enzyme-bound-ligand and less than about 20 active sites per molecule of ligand as enzyme-bound-ligand, but site-ligand molecule ratios may be as high as 1,000 to 1, depending on the type of assay and the affinity of the receptor. Preferably, the ratio of receptor active sites to molecules of enzyme-bound-ligand will be at least one, usually at least two, and the ratio of active sites to molecules of ligand as enzyme-bound-ligand will be less than about 5 to 1. The ratio will vary to a great degree depending on binding constants and the amount of ligand suspected of being present. The method of determining binding sites for the receptor will be discussed subsequently in the experimental section.

The enzyme-bound-ligand will usually have molecules of ligand to enzyme subunit ratios on the average over the entire composition in the range of 0.01 – 100:1, frequently 0.02 – 50:1, and more frequently about 0.04 – 25:1, wherein the number of ligands when the ligand is a protein is expressed as the number of ligand molecules times the number of its component polypeptide chains. For small ligands (less than about 10,000 molecular weight), there will generally be at least one ligand, more usually at least two ligands per enzyme, while with large ligands (greater than about 5,000 molecular weight) there will generally be at least one enzyme per ligand. In the area of overlap, the ratio will depend on the nature of the ligand, among other factors to be discussed.

The number of small ligands per enzyme will be affected to some degree by the molecular weight of the enzyme. However, normally, the fewer molecules of ligand bound to an enzyme to achieve the desired degree of inhibitability with receptor, the more sensitive the assay. Therefore, the number of small ligands per enzyme will usually not exceed 40, more usually not exceed 30, and will not exceed 1 ligand per 2,000 molecular weight of enzyme on the average over the entire composition. Usually, the range of ligands will be 1 to 40, more usually 1 to 24, and with random substitution 2 to 20.

With large ligands, there will be on the average not more than one enzyme per 2,000 molecular weight, usually not more than one enzyme per 4,000 molecular weight, and more usually not more than one enzyme per 6,000 molecular weight.

In some instances, a number of enzymes bind together in a stable arrangement to form a multienzyme complex. Because of the juxtaposition of the enzymes, a number of reaction may be carried out sequentially in an efficient manner, providing localized high concentrations of reactants. Therefore, the ligand may be bound to a combination of enzymes, whereby there will be a plurality of enzymes per ligand. If a number of ligands were bound to the multienzyme complex, one could have 1:1 mole ratio of enzymes to ligand, although, in fact, there would be a plurality of enzymes and ligands involved in a single aggregation. The number of enzymes bound together, either as a multienzyme complex or by another mechanism will rarely exceed 20, usually not exceed 10, and commonly be in the range of 2 to 5 enzymes.

All other things being equal, the greater the number of enzymes per large ligand, the greater the sensitivity of the assay. However, the enzymes may interfere with receptor recognition, affect solubility and be deleterious in other ways. Therefore, usually, the number of enzymes bonded to a large ligand will be such that there will be no more than one enzyme polypeptide chain for every 2,000 molecular weight of the ligand.

The concentration of receptor and enzyme will be related to the range of concentration of the ligand to be assayed. The solution to be assayed will be used directly, unless a relatively high concentration of ligand is present. If a high concentration is present, the unknown solution will be diluted so as to provide a convenient concentration. However, in many biological systems of interest, the amount of material being assayed will be relatively small and dilution of the unknown substrate will usually not be required.

To illustrate the subject method, a soluble receptor is employed for a particular ligand. For illustrative purposes, the ligand will be considered the hapten, morphine, and the receptor will be an antibody specific for morphine. It should be noted parenthetically, that antibodies generally recognize molecular shape and distribution of polar groups in a ligand, although a portion of the ligand may be significantly modified without preventing recognition. For example, both morphine ant its glucuronide can be bound to certain morphine antibodies.

An enzyme is first modified by bonding one or more morphine molecules to the enzyme; a sufficient number of morphine groups are employed so that greater than about 20% inhibition, usually 50% inhibition, and preferably, at least 70% inhibition is obtained when the maximum number of ligands are conjugated to receptor. Complete inhibition is usually neither necessary or desirable. In many instances, all that is required is that there be a measurable difference between completely uninhibited and maximally inhibited enzyme-bound-ligand which would allow for a semi-quantitative or quantitative determination of a ligand through a desired range of concentrations. Any convenient enzyme can be used that will catalyze the reaction of a substrate that can be easily detected and for which a substrate is available which allows for inhibition of the enzyme when bound to receptor.

A solution is prepared of the antibody at the requisite concentration. Only a few microliters of solution are required. The antibody, maintained at a pH at which it is active in binding morphine, is introduced into a solution of the enzyme-bound-morphine at the desired concentration. The reactivity of the combined antibody and enzyme-bound-morphine solution can be determined by taking an aliquot, adding it to its substrate under conditions where the enzyme is active, and determining the spectroscopic change as a function of time at a constant temperature. The rate of this change will be the result that should be obtained when there is no morphine present in the unknown solution.

Normally, the ligand and enzyme-bound-ligand reversibly bind to receptor, so that the order of addition of reagents is not crucial.

A second aliquot is taken and added to the unknown solution. The unknown solution may contain the substrate and any other additives which are required for enzymatic activity. Alternatively, the unknown solution may first be combined with the antibody-(enzyme-bound-morphine) complex, allowed to come to equilibrium and then mixed with the substrate. In either case the rate of change in the spectrum is determined. A variant of the above method is to add combined enzyme-bound-morphine and unknown solution to the antibody and then add this solution to the substrate. Other obvious variations come readily to mind.

If all concentrations of reagents except morphine are kept constant and several standard solutions of morphine are employed, then one can relate the change in the spectrum over specified periods of time to the morphine concentrations. Obviously, the standardized system can then be used to determine rpaidly, accurately, and efficiently the amount of morphine, or any other ligand in the unknown.

The manner of assaying for the enzyme can be widely varied depending on the enzyme, and to some degree the ligand and the medium in which the ligand is obtained. Conveniently, spectrophotometric measurements can be employed, where absorption of a cofactor, a substrate or the product of the substrate absorbs light in the ultraviolet or visible region. However, in many instances other methods of determination may be preferred. Such methods include fluorimetry, measuring luminenscence, ion specific electrodes, viscometry, electron spin resonance spectrometry, and metering pH, the name a few of the more popular methods.

The assays will normally be carried out at moderate temperatures, usually in the range of from 10° to 50° C, and more usually in the range of about 15° to 40° C. The pH of the assay solutions will be in the range of about 5 to 10, usually about 6 to 9. Illustrative buffers include (trishydroxymethyl)methylamine salt, carbonate, borate and phosphate.

Whether oxygen is present or the assay is carried out in an inert atmosphere, will depend on the particular assay. Where oxygen may be an interferant, an inert atmosphere will normally be employed. Normally, hydroxylic media will be employed, particularly aqueous media, since these are the media in which the enzyme is active. However 0 to 40 volume percent of other liquids may also be present as co-solvents, such as alcohols, esters, ketones, amides, etc. The particular choice of the cosolvent will depend on the other reagents present in the medium, the effect on enzyme activity, and any desirable or undesirable interactions with the substrate or products.

As already indicated, antibodies will frequently recognize a family of compounds, where the geometry and spatial distribution of polar groups are similar. Frequently, by devising the haptenic structure and the method of binding to the antigen when producing the antibodies, the specificity of the antibody can be varied. In some instances, it may be desirable to use two or more antibodies, usually not more than six antibodies, so that the antibody reagent solution will be able to detect an entire group of compounds, e.g., morphine and barbiturates. This can be particularly valuable for screening a sample to determine the presence of any member of a group of compounds or determining whether a particular class of compounds is present, e.g., drugs of abuse or sex hormones. When combinations of antibodies are used, it will usually be necessary to employ corresponding combinations of enzyme-bound-ligands.

Ligand

Turning now to a general consideration of the reagents, the first reagent to be considered is the ligand. Any ligand may be employed for which an appropriate receptor may be found having satisfactory specificity for the ligand. The recent literature contains an increasing number of reports of receptors for an increasingly wide variety of biologically active materials. Compounds for which receptors can be provided range from simple phenylalkylamines, e.g., amphetamine, to very high molecular weight polymers, e.g., proteins.

Among ligands which are drugs, will be compounds which act as narcotics, hypnotics, sedatives, analgesics, antipyretics, anaesthetics, psychotogenic drugs, muscle relaxants, nervous system stimulants, anticholinesterase agents, parasympathomimetic agents, sympathomimetic agents, α-adrenergic blocking agents, antiadrenergic agents, ganglionic stimulating and blocking agents, neuromuscular agents, histamines, antihistamines, 5-hydroxy-tryptamine and antagonists, cardiovascular drugs, antiarrhythmic drugs, antihypertensive agents, vasodilator drugs, diuretics, pesticides (fungicides, antihelminthics, insecticides, ectoparasiticides, etc.), antimalarial drugs, antibiotics, antimetabolites, hormones, vitamins, sugars, thyroid and antithyroid drugs, corticosteroids, insulin, oral hypoglemic drugs, tumor cells, bacterial and viral proteins, toxins, blood proteins, and their metabolites.

(A drug is any chemical agent that affects living protoplasm. (Goodman & Gilman, The Pharmacological Basis of Therapeutics, 3rd Ed., Macmillan, New York (1965).) A narcotic is any agent that produces sleep as well as analgesia.)

Included among such drugs and agents are alkaloids, steroids, polypeptides and proteins, prostaglandins, catecholamines, xanthines, arylalkylamines, heterocyclics, e.g., thiazines, piperazines, indoles, and thiazoles, amino acids, etc.

Other ligands of interest besides drugs are industrial pollutants, flavoring agents, food additives, e.g., preservatives, and food contaminants.

Broadly, the ligands will be organic compounds of from 100 to 100,000 molecular weight, usually of from about 125 to 40,000 molecular weight, more usually 125 to 20,000 molecular weight. The ligand will usually have from about 8 to 5,000 carbon atoms and from about 1 to 3,500 heteroatoms.

A substantial portion of the ligands will be monomers or low order polymers, which will have molecular weights in the range of about 100 to 2,000, more usually 125 to 1,000. Another significant portion of the ligands will be polymers (compounds having a recurring group) which will have molecular weights in the range of from about 750 to 100,000, usually from about 2,000 to 60,000, more usually 2,000 to 50,000. For polymers of varying molecular weight, weight average molecular weight is intended.

In some instances, high molecular weight materials will be of interest. For example, blood proteins will generally be in excess of 100,000 molecular weight. In the case of lipoproteins, the molecular weight will be in the range of 3 million to 20 million. The globulins, albumins and fibrinogens will be in the range of 100,000 to 1,000,000.

The ligands will normally be composed of carbon, hydrogen, nitrogen, oxygen, sulfur, phosphorous, halogen, and metals, primarily as their cations, such as the alkali and alkaline earth metals and the metals of Groups IB, IIB, VIIB, and VIIIB, particularly the third row of the periodic chart. Most usually, the ligands will be composed primarily of carbon, hydrogen, nitrogen, oxygen and sulfur.

Structurally, the ligands may be monomers or polymers, acyclic, mono or polycyclic, having carbocyclic or heterocyclic rings. The ligands will have a wide variety of functionalities, such as halo, oxocarbonyl, nonoxocarbonyl, amino, oxy (hydroxy, aryloxy, alyloxy and cycloalyloxy ["alyl" intends a monovalent aliphatic radical]), thiooxy, dithio, hydrazo, and combinations thereof.

The ligands may be divided into three different categories, based on their biological relationship to the receptor. The first category is antigens, which when introduced into the bloodstream of a vertebrate, result in the formation of antibodies. The second category is haptens, which when bound to an antigenic carrier, and the hapten bound antigenic carrier is introduced into the bloodstream of a vertebrate, elicit formation of antibodies specific for the hapten. The third category of ligands includes those which have naturally occurring receptors in a living organism and the receptors can be isolated in a form specific for the ligand.

Of course, biological substances which are native to one species and have naturally occurring receptors in that species, may also be haptens when bonded to a protein and introduced into an animal of the same or a different species. Therefore, the classification is somewhat arbitrary in that the ligand may be an antigen as to one species, a hapten as to another species, and may have naturally occurring receptors in a third species.

Antigens are for the most part protein or polysaccharide in nature and foreign to the animal into which they are injected.

The most important body of ligands for the purposes of the invention are the haptens. "Substances which on injection do not give rise to antibodies, but which are able to react with antibodies specifically to produce either precipitation or to inhibit precipitation have been termed haptens. This definition has been used to include not only the simple chemical substances which are determinants of specificity when conjugated to protein, and which inhibit precipitation, but also substances obtained from natural sources such as the pneumococcal type specific polysaccharides and dextran which are not antigenic in the rabbit on primary injection." Kabat, et al, Experimental Immunochemistry, Charles C. Thomas, Springfield, Illinois (1967). In the following discussion the term hapten will be confined to groups artificially introduced into antigenic carriers which promote the formation of antibodies to those groups.

The third group of ligands are those which have naturally occurring receptors. The receptors may be proteins, nucleic acids, such as ribonucleic acid (RNA) or deoxyribonucleic acid (DNA), or membranes associated with cells. Illustrative ligands which have naturally occurring receptors are thyroxine, many steroids, such as the estrogens, cortisone, corticosterone, and estradiol; polypeptides such as insulin and angiotensin, as well as other naturally occurring biologically active compounds. See Murphy, et al, J. Clin. Endocr., 24, 187 (1964); Murphy, ibid, 27, 973, (1967); ibid, 28, 343 (1968); BBA, 176, 626, (1969); McEwen, et al, Nature, 226, 263 (1970); Morgan, et al, Diabetes, (1966); Page, et al, J. Clin. Endocr., 28, 200, (1969).

The ligands may also be categorized by the chemical families which have become accepted in the literature. In some cases, included in the family for the purpose of this invention, will be those physiomimetic substances which are similar in structure to a part of the naturally occurring structure and either mimic or inhibit the physiological properties of the natural substances. Also, groups of synthetic substances will be included, such as the barbiturates and amphetamines. In addition, any of these compounds may be modified for linking to the enzyme at a site that may cause all biological activity to be destroyed. Other structural modifications may be made for the ease of synthesis or control of the characteristics of the antibody. These modified compounds are referred to as ligand counterfeits.

A general category of ligands of particular interest are drugs and chemically altered compounds, as well as the metabolites of such compounds. The interest in assaying for drugs varies widely, from determining whether individuals have been taking a specific illicit drug, or have such drug in their possession, to determining what drug has been administered or the concentration of the drug in a specific biological fluid.

The drugs are normally of from eight carbon atoms to 40 carbon atoms, usually of from 9 to 26 carbon atoms, and from 1 to 25, usually from 1 to 10 heteroatoms, usually oxygen, nitrogen or sulfur. A large category of drugs have from one to two nitrogen atoms.

One class of drugs has the following basic functionality:

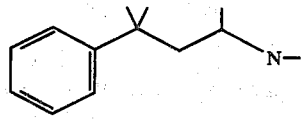

where the lines intend a bond to a carbon atom, and wherein any of the carbon atoms and the nitrogen atom may be bonded to hydrogen, carbon or a heterofunctionality. Drugs which have this basic structure include the opiates such as morphine and heroin, meperidine, and methadone.

Another class of drugs are the epinephrine like drugs which have the following basic functionality:

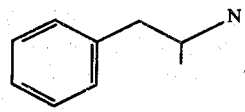

where the lines intend a bond to a carbon atom and wherein any of the carbon atoms and the nitrogen atom may be bonded to hydrogen, carbon or a heterofunctionality. Drugs which have this basic structure include amphetamine, narceine, epinephrine, ephedrine and L-dopa.

The ligand analogs of drugs will usually have molecular weights in the range of 150 to 1,200 more usually in the range of 175 to 700.

Alkaloids

The first category is the alkaloids. Included in the category of alkaloids, for the purpose of this invention, are those compounds which are synthetically prepared to physiologically simulate the naturally occurring alkaloids. All of the naturally occurring alkaloids have an amine nitrogen as a heteroannular member. The synthetic alkaloids will normally have a tertiary amine, which may or may not be a heteroannular member. The alkaloids have a variety of functionalities present on the molecule, such as ethers, hydroxyls, esters, acetals, amines, isoxazole, olefins, all of which, depending on their particular position in the molecule, can be used as sites for bonding to the enzyme.

Opiates

The opiates are morphine alkaloids. All of these molecules have the following functionality and minimum structures:

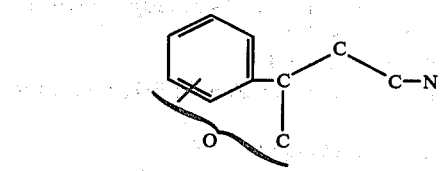

wherein the free valences are satisfied by a wide variety of groups, primarily carbon and hydrogen.

The enzyme-bound-ligand analog of these compounds will for the most part have the following minimum skeletal structure:

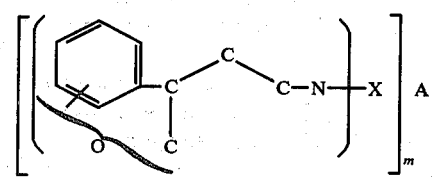

wherein X is a bond or a functionality such as imino, azo, oxy, thio, sulfonyl, oxocarbonyl, nonoxocarbonyl, or combinations thereof. Oxygen will be in the ortho, meta or β position. A is an enzyme which is bonded to X at other than its reactive site and retains a substantial portion of its natural enzymatic activity. There will be $m$ ligands bonded through X to the enzyme A.

The enzyme-bound-morphine and its closely related analogs will have the following formula:

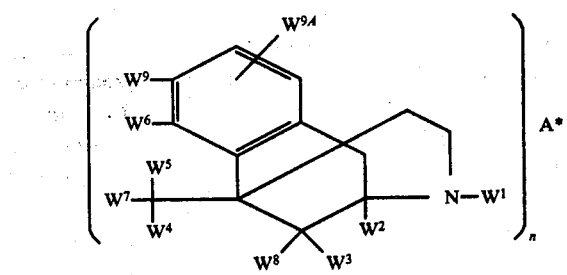

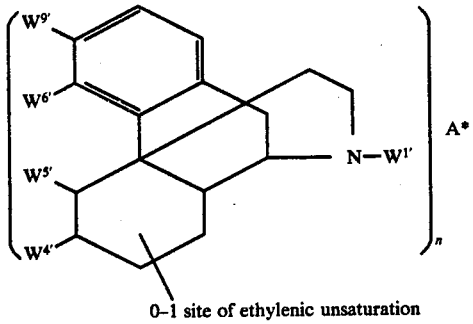

0-1 site of ethylenic unsaturation wherein:
any one of the W groups can be -X*, or an H of any of the W groups may be replaced by -X*, wherein X* is a bond or a linking group;

A* is an enzyme bonded at other than its reactive site, having a number (n) of ligands in the range of 1 to the molecular weight of A* divided by 2,000, usually in the range of 2 to 40;

$W^1$ is hydrogen or hydrocarbon of from one to eight carbon atoms, particularly alkyl or alkenyl of from 1 to 4 carbon atoms, cycloalkylalkyl of from 4 to 6 carbon atoms, or aralkyl, e.g., methyl, allyl, 3-methylbut-2-enyl-1, cyclopropylmethyl and β-phenethyl;

$W^2$ is hydrogen;

$W^3$ is hydrogen;

$W^4$ is hydrogen or taken together with $W^3$ a divalent radical of from 3 to 6 carbon atoms and 0 to 2 oxygen atoms, forming a six membered carbocyclic ring with the carbon chain to which they are attached, e.g., propylene-1,3,1-hydroxyprop-2-enylene-1,3,1-hydroxypropylene-1,3, 1-acetoxypropylene-1,3, 1-acetoxyprop-2-enylene-1,3, 1-oxopropylene-1,3, 1-oxoprop-2-enylene-1,3;

$W^5$ is hydrogen or hydroxyl;

$W^6$ is hydrogen, hydroxyl or taken together with $W^5$ oxy (—O—);

$W^7$ is hydrogen or methyl;

$W^8$ is hydrogen, methyl or hydroxyl;

$W^9$ is hydrogen, hydroxy, acyloxy of from 1 to 3 carbon atoms, e.g., acetoxy, (unless otherwise indicated, acyl intends only nonoxocarbonyl), hydrocarbyloxy of from 1 to 3 carbon atoms, e.g., methoxy, ethoxy, 2-(N-morpholino)ethoxy and glucuronyl; and $W^{9A}$ is hydrogen. (It is understood that in all the formulas, except when a minimum or skeletal structure is indicated, unsatisfied valences are satisfied by hydrogen).

(Hydrocarbyl is an organic radical composed solely of hydrogen and carbon and may be saturated or unsaturated, aliphatic, alicyclic, aromatic or combinations thereof).

By other than its reactive site, it is intended that the ligand is not bonded to the enzyme at a position which prevents the enzyme substrate, including necessary cofactors, from entering into the reaction catalyzed by the enzyme. It is understood, that with random substitution, the resulting product may include enzyme which has been deactivated by ligand bonded at the reactive site, as well as enzyme which is active and has ligand bonded at other than the reactive site.

The close morphine analogs will have the following formula:

wherein:
any one of the W groups can be -X*;
-X*, A*, and n have been defined previously;
$W^{1'}$ is alkyl of from 1 to 3 carbon atoms, e.g., methyl;
$W^{4'}$ is hydrogen, hydroxy, oxo or acetoxy;
$W^{5'}$ is hydrogen or hydroxyl;
$W^{6'}$ is hydrogen, hydroxyl or taken together with $W^{5'}$ oxy (—O—); and
$W^{9'}$ is hydroxy, acetoxy, or alkoxy of from 1 to 3 carbon atoms;

Those preferred compounds having the basic morphine structure will have the following formula:

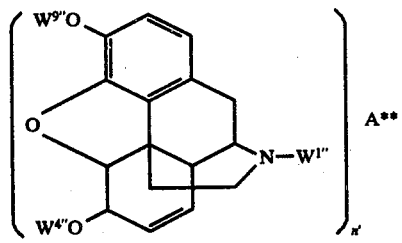

wherein:
one of $W^{1''}$ and $W^{9''}$ is -X; when other than -X;
$W^{1''}$ is methyl; and
$W^{9''}$ is hydrogen, methyl, acetyl or glucuronyl;
$W^{4''}$ is hydrogen or acetyl, usually hydrogen;
-X** is $$-Z\overset{O}{\underset{}{C}}-$$

wherein Z is hydrocarbylene of from 1 to 7 carbon atoms, preferably aliphatic, having from 0 to 1 site of ethylenic unsaturation; and -Z** is an enzyme, either specifically labelled with n' equal to 1 to 2 ligands or randomly (random as to one or more particular available reactive functionalities) labelled with n' equal to 2 to 30, more usually 2 to 20, the enzyme retaining a substantial proportion of its activity. The enzyme will be of from about 10,000 to 300,000, frequently about 10,000 to 150,000 molecular weight and is preferably an oxidoreductase, e.g., malate dehydrogenase, lactate dehydrogenase, glyoxylate reductase, or glucose 6-phosphate dehydrogenase, or a glycosidase, e.g., lysozyme or amylase.

Illustrative opiates which can be bound to an enzyme include morphine, heroin, hydromorphone, oxymorphone, metopon, codeine, hydrocodone, dihydrocodeine, dihydrohydroxycodeinone, pholcodine, dextromethorphan, phenazocine, and dionin and their metabolites.

Preferred compounds have $W^1$, or $W^9$ as -X*-A* or have $W^3$ and $W^4$ taken together to provide A*-X*-CHCH$_2$CH$_2$- or A*-X*-CH-CH=CH-.

Methadone

Another group of compounds having narcotic activity is methadone and its analogs, which for the most part have the following formula:

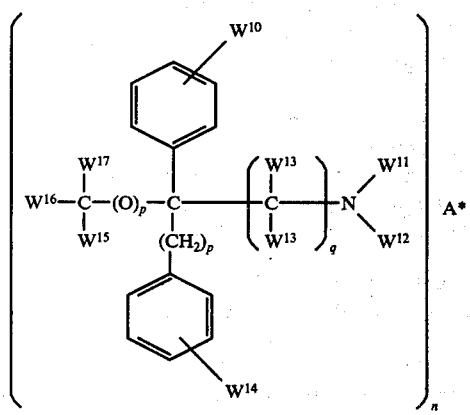

wherein:
any one of the W groups can be X*;
X*, A*, and n have been defined previously;
p is 0 or 1, usually being the same in both instances;
q is 2 or 3;
$W^{10}$ is hydrogen;
$W^{11}$ and $W^{12}$ are hydrogen, alkyl of from 1 to 3 carbon atoms, e.g., methyl, or may be taken together to form a six-membered ring with the nitrogen atom to which they are attached, e.g., pentylene-1,5 and 3-oxa or 3-azapentylene-1,5;
$W^{13}$ is hydrogen or methyl, only one $W^{13}$ being methyl;
$W^{14}$ is hydrogen;
$W^{15}$ is hydrogen or hydroxyl;
$W^{16}$ is hydrogen, acyloxy of from 1 to 3 carbon atoms, e.g., propionoxy, or hydroxy (when $W^{15}$ and $W^{16}$ are both hydroxy, the oxo group is intended); and
$W^{17}$ is hydrogen or alkyl of from 1 to 3 carbon atoms, e.g., ethyl.

Illustrative compounds which can be linked to an enzyme are methadone, dextromoramide, dipipanone, phenadoxone, propoxyphene (Darvon) and acetylmethadol.

Metabolites of methadone and methadone analogs are also included. Among the metabolites for methadone is N-methyl 2-ethyl-3,3-diphenyl-5-methylpyrroline.

Preferred compounds are when $W^{11}$ or $W^{17}$ is -X*.

A narrower class of methadone and its analogs are of the formula:

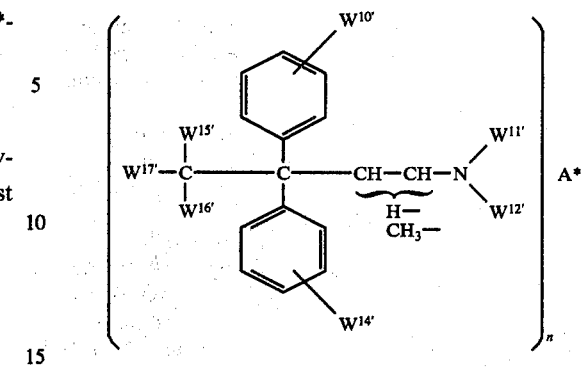

wherein:
any one of the W groups can be -X*;
X*, A* and n have been defined previously;
$W^{10'}$ and $W^{14'}$ are hydrogen;
$W^{11'}$ and $W^{12'}$ are methyl or are taken together with the nitrogen atom to which they are attached to form a morpholino or piperidine ring;
$W^{15'}$ and $W^{16'}$ are hydrogen, hydroxy, acetoxy, at least one being hydroxy or acetoxy; and
$W^{17'}$ is alkyl of from 1 to 3 carbon atoms.

The methadone derivatives will for the most part have the following formula:

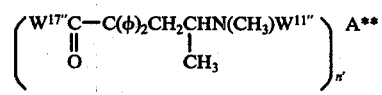

wherein:
one of $W^{11''}$ or $W^{17''}$ is X**;
X, A, and n' have been defined previously;
φ is phenyl;
when other than X**
$W^{11''}$ is methyl; and
$W^{17''}$ is propyl.

The metabolites of methadone and close analogs will for the most part have the following formula:

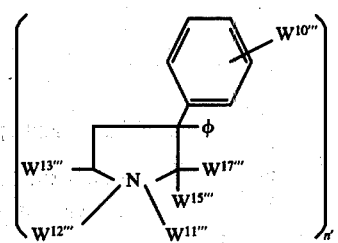

wherein:
any one of the W groups can be -X*, X*, A* and n have been defined previously;
φ is phenyl;
$W^{10'''}$ is hydrogen, hydroxyl, methoxyl or acetoxyl, that is of from 0 to 2 carbon atoms, and except when hydrogen of from 1 to 2 oxygen atoms;
$W^{11'''}$ is hydrogen, methyl, or a free valence joined with $W^{15'''}$;
$W^{12'''}$ is an unshared pair of electrons;
$W^{13'''}$ is hydrogen or methyl;
$W^{15'''}$ is hydrogen, hydroxy, or taken together with $W^{11'''}$ forms a double bond between the nitrogen atom and the carbon atom to which $W^{11''''}$ and $W^{15''''}$ are respectively attached; and $W^{17''''}$ is alkyl of from one to three carbon atoms, usually two carbon atoms, or may be taken together with $W^{15''''}$ to form alkylidenyl of from 1 to 3 carbon atoms, usually 2 carbon atoms.

Preferred compounds are those where $W^{11''''}$ or $W^{17''''}$ are X*, particularly $W^{17''''}$, with $W^{11''''}$ as methyl.

Illustrative compounds which may be linked to an enzyme include phenylbenzyl(1-dimethylamino-2-propyl)methyl succiate, phenylbenzyl(1-dimethylamino-2-propyl)methyl oxalate, diphenyl(2-dimethylamino-1-propyl)methyl maleate, O-carboxymethyl 4,4-diphenyl-7-dimethylamino-2-heptanone oxime, 4,4-diphenyl-7-dimethylamino-3-octyl succiate, N-(2,2-diphenyl-3-methyl-4-morpholinobutyryl)glycine, 3-ethyl-4,4-diphenyl-6-dimethylaminohept-2-enoic acid, 6-keto-7,7-diphenyl-9-diphenyl-9-(dimethylamino) decanoic acid, N-carboxymethyl 2-ethyl-3,3-diphenyl-5-methylpyrrolidine.

Meperidine

The third group of compounds which have narcotic activity and are meperidine or meperidine analogs, have for the most part the following formula:

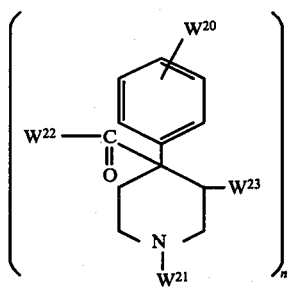

wherein:
any one of the W groups can be -X*;
X*, A*, and n have been defined previously;
$W^{20}$ is hydrogen;
$W^{21}$ is hydrogen, alkyl of from 1 to 3 carbon atoms, e.g., methyl, aminophenylakyl, e.g., β-(p-aminophenyl)ethyl, or phenylaminoalkyl, e.g., phenylaminopropyl, (alkyl of from 2 to 3 carbon atoms);
$W^{22}$ is alkoxy of from 1 to 3 carbon atoms, e.g, ethoxy; and
$W^{23}$ is hydrogen or methyl.

Illustrative compounds are meperidine, alphaprodine, alvodine and anileridine.

Preferred compounds are those where $W^{21}$ or $W^{22}$ is -X* or a hydrogen of $W^{21}$ is replaced with -X*.

Indole Alkaloids

A second group of ligands of interest are based on tryptamine and come within the class of indole alkaloids, more specifically ergot alkaloids. These compounds will have the following minimal structure:

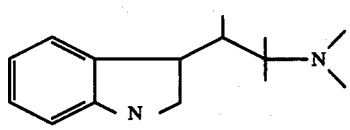

wherein the free valences are satisfied by a variety of groups, primarily carbon and hydrogen, although other substituents may be present such as carboxyl groups, hydroxyl groups, keto groups, etc. The most common member of this class which finds use is lysergic acid, primarily as its diethylamide. Other members of the indole alkaloid family which can also be assayed for are the strychnine group and the indolopyridocoline group, which finds yohimbine and reserpine as members.

The enzyme substituted indole alkaloids will have the following formula:

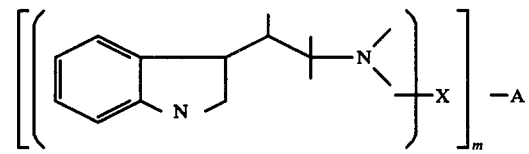

wherein m, X and A have been defined previously.

Other groups of alkaloids include the steroid alkaloids, the iminazolyl alkaloids, the quinazoline alkaloids, the isoquinoline alkaloids, the quinoline alkaloids, quinine being the most common, and the diterpene alkaloids.

For the most part, the alkaloids bonded to an enzyme will be of from about 300 to 1,500 molecular weight, more usually of from about 400 to 1,000 molecular weight. They are normally solely composed of carbon, hydrogen, oxygen, and nitrogen; the oxygen is present as oxy and oxo and the nitrogen present as amino or amido.

Catecholamines

The first group in this category are catecholamines of the formula:

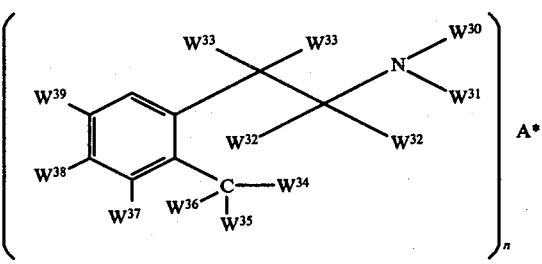

wherein:
any one of the W groups can be -X*;
X*, A* and n have been defined previously;
$W^{30}$ is hydrogen or alkyl of from 1 to 3 carbon atoms, e.g., methyl;
$W^{31}$ is hydrogen, or alkyl of from 1 to 3 carbon atoms, e.g., methyl;
$W^{32}$ and $W^{33}$ are hydrogen;
$W^{34}$ is hydrogen, hydroxy, dimethoxycarboxyphenacyl, and dimethoxy-α-phthalidyl;
$W^{35}$ and $W^{36}$ are hydrogen, one of which may be taken with $W^{31}$ to form a bond, and when $W^{31}$ and $W^{35}$ are taken together, each of $W^{32}$ and $W^{33}$, and $W^{30}$ and $W^{36}$ may be taken together to form a double bond;
$W^{37}$ is hydrogen or alkoxy of from 1 to 3 carbon atoms; e.g., methoxy;
$W^{38}$ and $W^{39}$ are hydroxy or alkoxy of from 1 to 3 carbon atoms, e.g., methoxy.

Illustrative compounds include cotainine, narceine, noscapine and papaverine.

Preferred compounds are where $W^{30}$, $W^{38}$ or $W^{39}$ are -X* or have a hydrogen replaced with -X*.

A group of compounds related to the catecholamines are epinephrine, amphetamines and related compounds. These compounds have the formula:

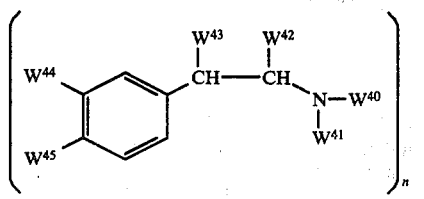

wherein:
any one of the W groups can be -X*;
X*, A* and $n$ have been defined previously;
$W^{40}$ and $W^{41}$ are hydrogen or alkyl of from 1 to 3 carbon atoms, e.g., methyl and isopropyl, preferably one is hydrogen;
$W^{42}$ is hydrogen, alkyl of from 1 to 3 carbon atoms, e.g., methyl and ethyl, or may be taken together with $W^{40}$ to form a ring having six annular members with the nitrogen as the only heteroatom;
$W^{43}$ is hydrogen, hydroxyl, carbomethoxy, or may be taken together with $W^{40}$ to form a morpholine ring;
$W^{43}$ is carbomethoxy, when $W^{40}$ and $W^{42}$ are taken together to form a piperidine ring; and
$W^{44}$ and $W^{45}$ are hydrogen, hydroxyl or alkoxyl of from 1 to 3 carbon atoms.

Illustrative compounds which can be bonded to an enzyme are ephedrine, epinephrine, L-dopa, benzidrine (amphetamine), paredrine, methamphetamine, methyl phenidate and norephedrine.

Illustrative compounds which can be linked to an enzyme include 3-(3',4'-dihydroxyphenyl)-3-hydroxypropionic acid, N-($\beta$-($\beta$,3,4-trihydroxyphen)ethyl) N-methyl glycine, N-(1-phenyl-2-propyl)oxalamic acid, O-(1-phenyl-2-methylamino-1-propyl)glycolic acid, p-(2-methylaminopropyl-1)phenoxyacetic acid, N-(1'-phenyl-2'-propyl) glycine, 4-methylamino-4-phenylvaleric acid, para-(2-aminopropyl-1)phenoxyacetic acid, 4-methylamino-5-phenylvaleric acid, and 3-amino-4-phenylbutyric acid.

Where $W^{44}$ and $W^{45}$ are hydrogen, preferred compounds will have the following formula:

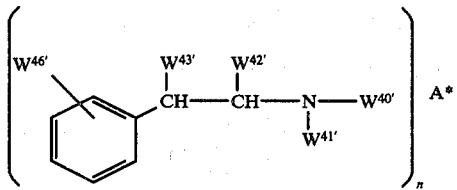

wherein:
any one of the W groups can be -X*;
X*, A* and $n$ have been defined previously;
$W^{40'}$ and $W^{41'}$ are hydrogen or alkyl of from 1 to 3 carbon atoms, preferably one is hydrogen;
$W^{42'}$ is hydrogen, methyl or may be taken together with $W^{40'}$ to form a piperidine ring;
$W^{43'}$ is hydrogen, hydroxyl or carbomethoxy; and
$W^{46'}$ is hydrogen.

Where $W^{44}$ and $W^{45}$ are oxy, the preferred compounds have the following formula:

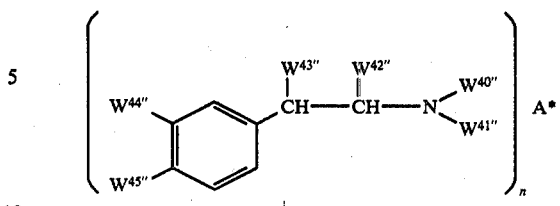

wherein:
any one of the W groups can be -X*;
X*, A* and $n$ have been defined previously;
$W^{40''}$, $W^{41''}$, and $W^{42''}$ are hydrogen or methyl;
$W^{43''}$ is hydrogen or hydroxyl; and
$W^{44''}$ and $W^{45''}$ are hydroxyl or methoxy.

Closely related compounds to the amphetamines are those where a saturated five or six membered ring is substituted for the phenyl ring. These compounds will have the following formula:

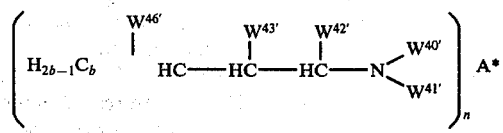

wherein:
any one of the W groups is -X*;
X*, A* and $n$ have been defined previously;
$W^{40'-41'}$ have been defined above;
$W^{42'}$ is hydrogen or methyl;
$W^{43'}$ is hydrogen or hydroxyl;
$W^{46'}$ is hydrogen; and
$b$ is an integer of from four to five.

Of particular interest are those amphetamines bonded to enzymes of the following formula:

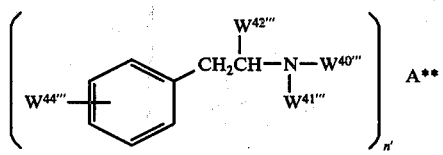

wherein one of $W^{40'''}$, $W^{42'''}$, and $W^{44'''}$ is -X; when other than -X
$W^{40'''}$ is hydrogen;
$W^{42'''}$ is methyl; and
$W^{44'''}$ is hydrogen;
$W^{41'''}$ is hydrogen or methyl;
X is -Z-CO-, wherein Z is hydrocarbylene of from 1 to 7 carbon atoms, usually aliphatic, having from 0 to 1 site of ethylenic unsaturaction, with the proviso that when $W^{44'''}$ is -X, -X** is -O-Z-CO-;
A** and $n'$ have been defined previously.

Barbiturates

A wide class of synthetic drugs which finds extensive and frequent abuse are the barbiturates. These compounds are synthetically readily accessible and their use only difficultly policed. The compounds which find use will come within the following formula:

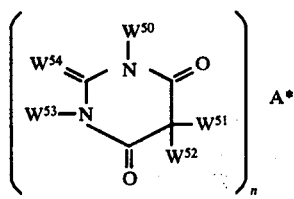

wherein:
any one of the W groups can be -X*;
X*, A*, and $n$ have been defined previously;
$W^{50}$ is hydrogen, alkyl of from 1 to 3 carbon atoms, e.g., methyl or alkali metal, e.g., sodium;
$W^{51}$ and $W^{52}$ are hydrogen, alkyl, alkenyl, cycloalkyl, cycloalkenyl, or aryl hydrocarbon of from 1 to 8, more usually 1 to 6 carbon atoms, e.g., ethyl, n-butyl, α-methylbutyl, isoamyl, allyl, $\Delta^1$-cyclohexenyl, and phenyl;
$W^{53}$ is hydrogen, or alkali metal, e.g., sodium;
$W^{54}$ is oxygen or sulfur.

Illustrative compounds are veronal, medinal, luminal, prominal, soneryl, nembutal, amytal, dial, phenadorn, seconal, evipan, phenobarbital and pentothal.

Preferred compounds would have $W^{50}$ or $W^{51}$ or a hydrogen of $W^{50}$ or $W^{51}$ as -X*. Also preferred is when one of $W^{51}$ and $W^{52}$ is hydrocarbyl of from 2 to 8 carbon atoms.

Illustrative compounds which may be linked to an enzyme include 5,5-diethyl-1-carboxymethylbarbituric acid, 5-ethyl-5-n-butyl-1-succinoylbarbituric acid, 5-ethyl-5-phenyl-1-(N'-(2'''-chloroethyl)-2''-aminoethyl)-barbituric acid, 5-(2'-carboxy-$\Delta^{1'2'}$-cyclohexenyl)-1,5-dimethylbarbituric acid, N-carboxymethyl phenobarbital, 5-(γ-crotonic acid)-5-(2'-pentyl)-barbituric acid, 5-(p-aminophenyl)-5-ethylbarbituric acid, 5-(5'-pentanoic acid)-5-(2'-pentyl)barbituric acid, and 1-methyl-5-ethyl-5-(p-carboxyphenyl)barbituric acid.

Of particular interest are those barbiturates bonded to an enzyme of the formula:

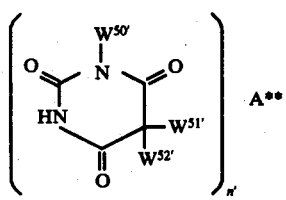

wherein one of $W^{50'}$ and $W^{51'}$ is -X; when other than -X:
$W^{50'}$ is hydrogen, methyl or alkali metal, e.g., sodio; and
$W^{51'}$ is hydrocarbon of from 1 to 8 carbon atoms, having from 0 to 1 site of ethylenic unsaturation;
$W^{52'}$ is hydrocarbon of from 2 to 8 carbon atoms, having from 0 to 1 site of ethylenic unsaturation;
X** is -Z-CO-, wherein Z is hydrocarbylene of from 1 to 7 carbon atoms, usually aliphatic, having from 0 to 1 site of ethylenic unsaturation;
A** and $n'$ have been defined previously.

Glutethimide

Another compound of interest is glutethimide, wherein the enzyme bound analog will have the following formula:

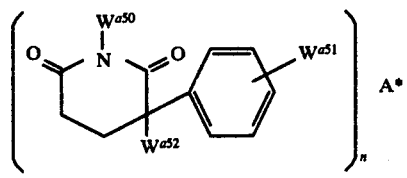

wherein:
any one of the W groups can be -X*;
X*, A* and $n$ have been defined previously;
$W^{a50}$ and $W^{a51}$ are hydrogen; and
$W^{a52}$ is lower alkyl of from 1 to 3 carbon atoms, e.g., ethyl.

Cocaine

A drug of significant importance in its amount of use is cocaine. The enzyme bound cocaine or cocaine metabolites or analogs, such as ecgonine, will for the most part have the following formula:

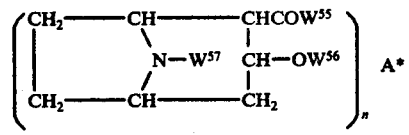

wherein:
any one of the W groups can be -X*;
X*, A* and $n$ have been defined previously;
$W^{55}$ is hydroxy, methoxy, amino or methylamino;
$W^{56}$ is hydrogen or benzoyl; and
$W^{57}$ is hydrogen or alkyl of from 1 to 3 carbon atoms, e.g., methyl.

Of particular interest are those ecgonine derivatives (including cocaine derivatives) of the formula:

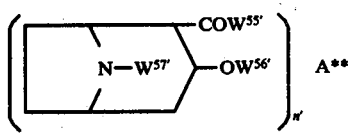

wherein one of $W^{56'}$ and $W^{57'}$ is -X; when other than -X:
$W^{56'}$ is hydrogen or benzoyl; and
$W^{57'}$ is methyl;
$W^{55'}$ is hydroxy or methoxy;
X** is

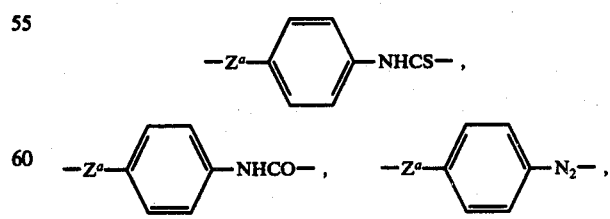

wherein $Z^a$ is methylene or carbonyl; or -Z-CO- wherein Z is hydrocarbylene of from 1 to 7 carbon atoms, usually aliphatic, having from 0 to 1 site of ethylenic unsaturation;
A** and $n'$ have been defined previously.

Diphenyl Hydantoin

Another compound of interest is the antiepileptic drug diphenyl hydantoin. This compound and its analogs will have the following formula:

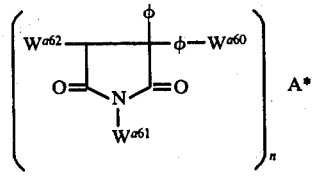

wherein:
any one of the W groups can be -X*;
X*, A* and n have been defined previously;
$\phi$ is phenyl;
$W^{a60}$, $W^{a61}$ and $W^{a62}$ are hydrogen.

Marijuana

Because of its ready availability and widespread use, tetrahydrocannabinol (the active ingredient of marijuana) and its congeners, cannabidiol and cannabinol and their metabolites are compounds of great interest, where a simple assay method would be of importance. The compounds which find use as analogs have the following formula:

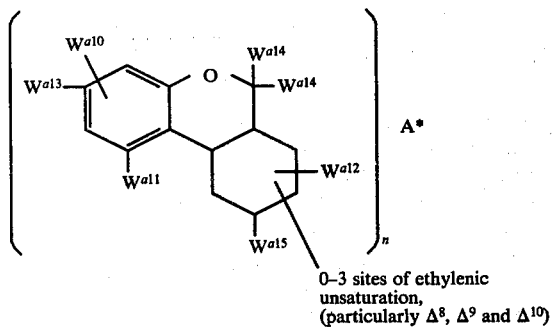

0–3 sites of ethylenic unsaturation,
(particularly $\Delta^8$, $\Delta^9$ and $\Delta^{10}$)

wherein:
any one of the W groups can be -X*;
X*, A* and n have been defined previously;
$W^{a10}$ is hydrogen or carboxyl;
$W^{a11}$ is hydroxyl or methoxyl;
$W^{a12}$ is hydrogen;
$W^{a13}$ is pentyl or hydroxypentyl;
$W^{a14}$ is hydrogen, methyl, or the two $W^{a14}$'s may be taken together to form a carbocyclic ring of from 5 to 6 annular members; and
$W^{a15}$ is methyl, hydroxymethyl or carboxyl.

Tranquilizers

A number of compounds have tranquilizer effects and because of their misuse or abuse do provide opportunities where the determination could be of use.

The first tranquilizer of interest is Meprobamate, also known as Miltown or Equanil. This compound and related analogs have the following formula:

$$\left( W^{a25}\overset{O}{\overset{\|}{C}}OCH_2-\overset{C_3H_7}{\underset{CH_3}{\overset{|}{\underset{|}{C}}}}-CH_2-O-\overset{O}{\overset{\|}{C}}W^{a26} \right)_n A^*$$

wherein:
any one of the W groups can be -X*;
X*, A* and n have been defined previously;
$W^{a25}$ and $W^{a26}$ are amino.

The next group of tranquilizers are benzdiazocycloheptanes and are known as Librium, Valium, Diazepam, or Oxazepam. These compounds and their related analogs will have the following formula:

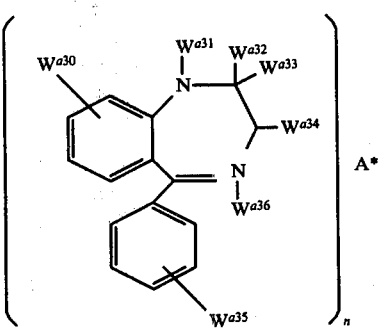

wherein:
any one of the W groups can be -X*;
X*, A*, and n have been defined previously;
$W^{a30}$ and $W^{a35}$ are hydrogen;
$W^{a31}$ is hydrogen, lower alkyl of from 1 to 3 carbon atoms, e.g., methyl, or may be taken together with $W^{a32}$ to form a double bond between the carbon and the nitrogen;
$W^{a33}$ is amino or lower alkylamino of from 1 to 3 carbon atoms, e.g., methylamino, or may be taken together with $W^{a32}$ to form a carbonyl;
$W^{a34}$ is hydrogen or hydroxyl; and
$W^{a36}$ is oxy or an unshared pair of electrons.

The next group of compounds are the phenothiazines of which chlorpromazine is a member. These compounds will for the most part have the following formula:

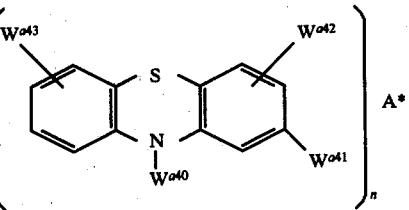

wherein:
any one of the W groups can be -X*;
X*, A*, and n have been defined previously;
$W^{a40}$ is hydrogen, alkyl of from 1 to 6 carbon atoms, dialkylaminoalkyl of from 4 to 8 carbon atoms, e.g., 3-(dimethylamino)propyl; N-hydroxyalkyl (alkyl of from 2 to 3 carbon atoms), N'-piperazinoalkyl (alkyl of from 2 to 3 carbon atoms), e.g., N-hydroxyethyl N'-piperazinopropyl; N-alkyl (alkyl of from 1 to 3 carbon atoms) N'-piperazinoalkyl (alkyl of from 2 to 3 carbon atoms), e.g., N-methyl N'-piperazinopropyl; and 2-(N-alkyl)-piperidinoalkyl, wherein the N-alkyl is of from 1 to 3 carbon atoms and the other alkyl is of from 2 to 3 carbon atoms, e.g., 2-(N-methyl)-piperidinoethyl, there being at least two carbon atoms between the heteroatoms;

$W^{a41}$ is hydrogen, chloro, trifluoromethyl, alkylmercapto of from 1 to 3 carbon atoms, e.g., methylmercapto and acyl of from 1 to 3 carbon atoms, e.g., acetyl; and $W^{a42}$ and $W^{a43}$ are hydrogen.

Amino Acids, Polypeptides and Proteins

The next group of compounds are the amino acids, polypeptides and proteins. For the most part, the amino acids range in carbon content from 2 to 15 carbon atoms, and include a variety of functional groups such as mercapto, dithio, hydroxyl, amino, guanidyl, pyrrolidinyl, indolyl, imidazolyl, methylthio, iodo, diphenylether, hydroxyphenyl, etc. These, of course, are primarily the amino acids related to humans, there being other amino acids found in plants and animals.

Polypeptides usually encompass from about 2 to 100 amino acid units (usually less than about 12,000 molecular weight). Larger polypeptides are arbitrarily called proteins. Proteins are usually composed of from 1 to 20 polypeptide chains, called subunits, which are associated by covalent or non-covalent bonds. Subunits are normally of from about 100 to 400 amino acid groups (~10,000 to 50,000 molecular weight).

Individual polypeptides and protein subunits will normally have from about 2 to 400, more usually from about 2 to 300 recurring amino acid groups. Usually, the polypeptides and protein subunits of interest will be not more than about 50,000 molecular weight and greater than about 750 molecular weight. Any of the amino acids may be used in preparing the polypeptide. Because of the wide variety of functional groups which are present in the amino acids and frequently present in the various naturally occurring polypeptides, the enzyme bonded compound can be bonded to any convenient functionality. Usually, the enzyme bonded compound can be bonded to a cysteine, lysine or arginine, tyrosine or histidine group, although serine, threonine, or any other amino acid with a convenient functionality, e.g., carboxy and hydroxy, may be used.

For the most part, the enzyme-labeled polypeptides will have the following formula:

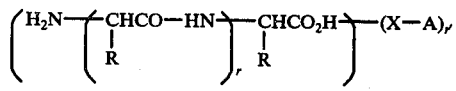

wherein X and A have been defined previously, and R is an amino acid residue, r being an integer of from 1 to 1,000, more usually of from 1 to 500, and most commonly of from 2 to 100. r' is an integer of at least one and not greater than the molecular weight of the polypeptide divided by 2,000.

Illustrative amino acids include glycine, alanine, serine, histidine, methionine, hydroxyproline, tryptophan, tyrosine, thyroxine, ornithine, phenylalanine, arginine, and lysine. Polypeptides of interest are ACTH, oxytocin, lutenizing hromone, insulin, Bence-Jones protein, chlorionic gonadotropin, pituitary gonadotropin, growth hormone, rennin, thyroxine bonding globulin, bradykinin, angiotensin, follicle stimulating hormone, etc.

In certain instances, it will be desirable to digest a protein and assay for the small polypeptide fragments. The concentration of the fragment may then be related to the amount of the original protein.

Steroids

Another important group of compounds which find use in this invention are the steroids, which have a wide range of functionalities depending on their function in the body. In addition to the steroids, are the steroidmimetic substances, which while not having the basic polycyclic structure of the steroid, do provide some of the same physiological effects.

The steroids have been extensively studied and derivatives prepared which have been bonded to antigenic proteins for the preparation of antibodies to the steroids. Illustrative compounds include: 17β-estradiol-6-(O-carboxymethyl-oxime)-BSA (bovine serum albumin) (Exley, et al, Steroids 18 593, (1971); testosterone-3-oxime derivative of BSA (Midgley, et al, Acta Endocr. 64 supplement 147, 320 (1970)); and progesterone-3-oxime derivative of BSA (Midgley, et al, ibid.)

For the most part, the steroids used have the following formula:

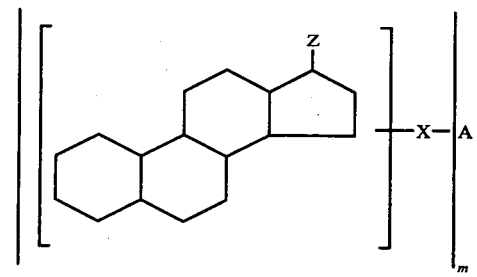

wherein m, X and A have been defined previously. Usually, the enzyme will be bonded to the A, B, or C rings, at the 2, 3, 4, 6 or 11 positions, or at the 16 or 17 positions of the D ring or on the side chains at the 17 position. Of particular interest is where X is bonded to the 6 position. The rings may have various substituents; particularly methyl groups, hydroxyl groups, oxocarbonyl groups, ether groups, and amino groups. Any of these groups may be used to bond the enzyme to the basic ring structure. For the most part, the steroids of interest will have at least one, usually 1 to 6, more usually 1 to 4 oxygen functionalities, e.g., alcohol, ether, esters, or keto. In addition, halo substituents may be present. The steroids will usually have from 18 to 27 carbon atoms, or as a glycoside up to 50 carbon atoms.

The rings may have one or more sites of unsaturation, either ethylenic or aromatic and may be substituted at positions such as the 6, 7 and 11 positions with oxygen substituents. In addition, there may be methyl groups at the 10 and 13 positions. The position marked with a Z, 17, may be and will be varied widely depending on the particular steroid. Z represents two monovalent groups or one divalent group and may be a carbonyl oxygen, an hydroxy group, an aliphatic group of from 1 to 8 carbon atoms, including an acetyl group, an hydroxyacetyl group, carboxy and carboxyalkyl of from 2 to 6 carbon atoms, an acetylenic group of from 2 to 6 carbon atoms or halo substituted alkyl or oxygenated alkyl group or a group having more than one functionality, usually from 1 to 3 functionalities.

For the second valence of Z, there may be a H or a second group, particularly hydroxyl, alkyl, e.g., methyl, hydrodyalkyl, e.g., hydroxymethyl; halo, e.g., fluoro or chloro, oxyether; and the like.

These steroids find use as hormones, male and female (sex) hormones, which may be divided into oestrogens, gestogens, antrogens, adrenocortical hormones (glucocorticoids), bile acids, cardiotonic glycosides and aglycones, as well as saponins sapogenins.

Steroid mimetic sustances, particularly sex hormones are illustrated by diethyl stilbestrol.

The sex hormones of interest may be divided into two groups; the male hormones (androgens) and the female hormones (oestrogens).

The androgens which find use will have the following formula:

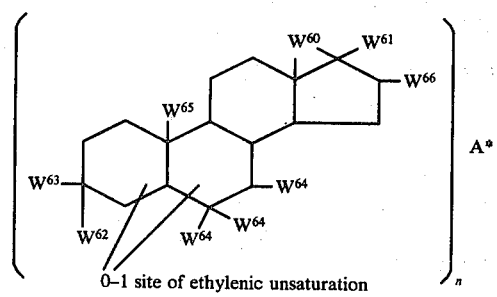

wherein:
any one of the W groups can be -X*;
X*, A* and n have been defined previously;
$W^{60}$ is hydrogen, or hydroxyl;
$W^{61}$ is hydrogen, methyl or hydroxyl (when two groups bonded to the same carbon atom are hydroxyl, oxo is intended);
$W^{62}$ and $W^{63}$ are hydrogen or hydroxyl, at least one of $W^{60-63}$ is hydroxy (either as hydroxy or oxo);
$W^{64}$ is hydrogen, or two $W^{64}$'s may be taken together to form a double bond;
$W^{65}$ is methyl; and
$W^{66}$ is hydrogen.

Illustrative compounds which may be bonded to an enzyme include testosterone, androsterone, isoandrosterone, etiocholanolone, methyltestosterone and dehydroisoandrosterone.

Illustrative compounds which may be linked to an enzyme include N-carboxymethoxy testosteroneimine, 17-monotestosteronyl carbonate, androsteronyl succinate, testosteronyl maleate, $O^3$-carboxymethyl $O^{17}$-methyl androst-5-ene-3β, 17β-diol, testosterone O-carboxypropyl oxime and androsteronyl carbonate.

The oestrogens have an aromatic A ring and for the most part have the following formula:

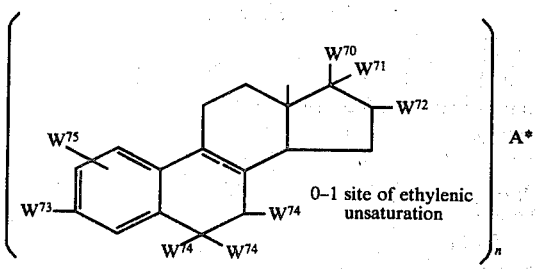

wherein:

any one of the W groups can be -X*;
X*, A* and n have been defined previously;
$W^{70}$ and $W^{71}$ are hydrogen, ethinyl or hydroxyl (when two hydroxyls are bonded to the same carbon atom, oxo is intended);
$W^{72}$ is hydrogen or hydroxyl;
$W^{73}$ is hydroxyl or alkoxyl of from 1 to 3 carbon atoms;
$W^{74}$ is hydrogen or two $W^{74}$'s may be taken together to form a double bond; and
$W^{75}$ is hydrogen.

Illustrative compounds which may be bonded to an enzyme are equilenin, β-estradiol, estrone, estriol, and 17-α-ethinyl-estradiol.

Illustrative compounds which may be linked to an enzyme include 3-carboxymethyl estradiol, b 2-chloromethylestrone, estrone glutarate, O-carboxymethyloxime of 6-ketoestradiol, equilenyl N-carboxymethyl thiocarbamate.

Another class of hormones are the gestogens which have the following formula:

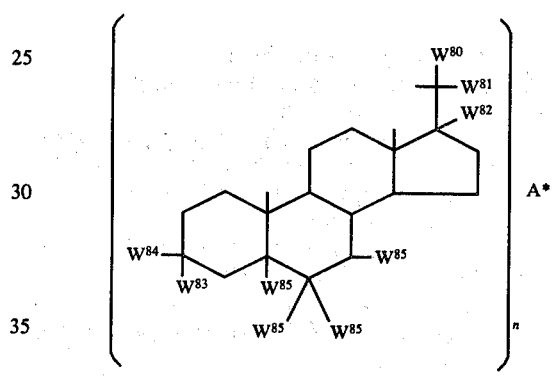

wherein:
any one of the W groups can be -X*;
X*, A* and n have been defined previously;
$W^{80}$ and $W^{81}$ are hydrogen or hydroxyl, at least one being hydroxyl (where two hydroxyl groups are bonded to the same carbon atom, oxo is intended);
$W^{82}$ is hydrogen or hydroxyl;
$W^{83}$ and $W^{84}$ are hydrogen or hydroxyl, at least one being hydroxyl; and
$W^{85}$ is hydrogen, or two $W^{85}$'s may be taken together to form a double bond.

Illustrative compounds which may be bonded to an enzyme include progesterone, pregnenolone, allopregnane-3a:20a-diol and allopregnan-3a-ol-20-one.

Illustrative compounds which may be linked to an enzyme include 20-progesterone O-carboxymethyl oxime, pregn-4-en-20-on-3-ylidinylmethylenecarboxylic acid, O-carboxymethyl progesterone 3-oxime, pregnenolonyl tartrate, O-pregnenolonyl tartrate, O-pregnenolonyl lactic acid, and allopreganane-3-carboxymethyl-20-ol.

The next important group of steroids is the corticosteroids which includes both the mineralcorticoids and the glucocorticoids. These compounds have the following formula:

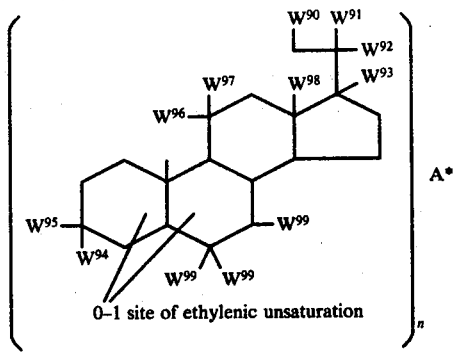

wherein:
any one of the W groups can be -X*;
X*, A* and n have been defined previously;
$W^{90}$ is hydrogen or hydroxyl;
$W^{91}$ and $W^{92}$ are hydrogen or hydroxyl, at least one of which is hydroxyl (when two hydroxyl groups are bonded to the same carbon atom, oxo is intended);
$W^{93}$ is hydrogen or hydroxyl;
$W^{94}$, $W^{95}$, $W^{96}$, and $W^{97}$ are hydrogen or hydroxyl, at least one of $W^{94}$ and $W^{95}$ is hydroxyl;
$W^{98}$ is methyl or formyl; and
$W^{99}$ is hydrogen or two $W^{99}$'s may be taken together to form a double bond.

Illustrative compounds which may be bonded to an enzyme are 17-hydroxydioxycorticosterone (Compound S), deoxycorticosterone, cortisone, corticosterone, 11-dihydrocortisone (Compound F), cortisol, prednisolone and aldosterone.

Illustrative compounds which may be linked to an enzyme include $O^{21}$-carboxymethyl corticosterone, N-carboxymethyl 21-carbamate cortisol, 21-cortisone succinate, 21-deoxocorticosterone succinate, and $O^{17}$-methyl, $O^{21}$-carboxymethyl cortisone.

An additional steroid family is the cardiotonic glycosides and aglycones of which digitalis is an important member. The basic compound is digitoxigenin, which is also found as the glycoside. The compounds of interest have the following formula:

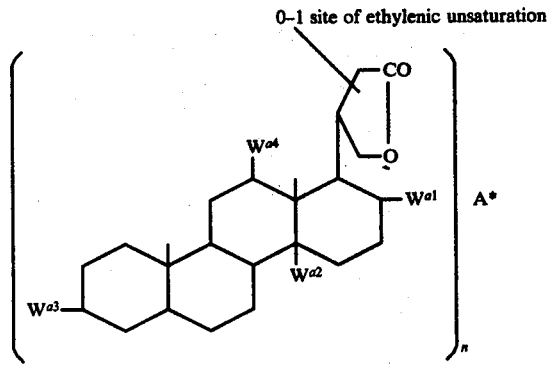

wherein:
any one of the W groups can be -X*;
X*, A* and n have been defined previously;
$W^{a1}$, $W^{a2}$, $W^{a3}$ and $W^{a4}$ are hydrogen, hydroxyl, or a glycoside, at least one being hydroxyl or a sugar, mostly as a glycoside. The sugars include xylose, glucose, cymarose, rhamnose, and galactose.

Also of interest are the saponins and sapogenins derived from plants. These compounds have a spiro ring structure at $C_{22}$.

Vitamins

The next group of compounds are the vitamins. Chemically, the vitamins do not provide a single chemical class, varying greatly in structure, but being classified as a group as to function. The vitamins include, vitamin A, which is a carotene, the B vitamin group which includes riboflavin, thiamine, niacin, pyridoxine, pantothenic acid, biotin, folic acid, and cyanocobalamine (Vitamin $B_{12}$); ascorbic acid (Vitamin C); the D vitamins which are steroidal derived; tocopherol (Vitamin E); and phytyl-1,4-naphthoquinone (Vitamin K).

Sugars

The next group of compounds are the sugars and saccharides. The saccharides are combinations of various sugars to form dimers, trimers and high molecular weight polymers, referred to as polysaccharides.

Prostaglandin

Another group of compounds of biological importance are the prostaglandins. These compounds when bonded to enzymes have for the most part the following formula:

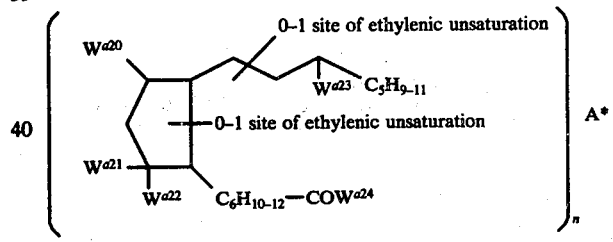

wherein:
any one of the W groups can be -X*;
X*, A* and n have been defined previously; $W^{a20}$ is hydrogen or hydroxyl;
$W^{a21}$ and $W^{a22}$ are hydrogen or hydroxyl, (where two hydroxyl groups are bonded to the same carbon atom, oxo is intended);
$W^{a23}$ is hydrogen or hydroxyl; and
$W^{a24}$ is hydroxyl, amino or an oxy group of from 1 to 6 carbon atoms, e.g., alkoxy.

Miscellaneous

Included in this group are the antibiotics such as penicillin, chloromycetin, actinomycetin, tetracycline, terramycin, and nucleic acids or derivatives, such as nucleosides and nucleotides.

Also of interest is serotonin which is 3-(2'-aminoethyl)-5-hydroxyindole. -X* may be bonded at either of the amino nitrogen atoms or the hydroxyl group.

Of course, many of the compounds which are of interest undergo metabolic changes, when introduced into a vertebrate. The particular physiological fluid which is tested may have little, if any of the original compound. Therefore, the original presence of the compound might only be detectable as a metabolite. In many instances, the metabolite may be the glucuronide, either oxy or oxo derivative of the original compound. In other instances, the original compound may have undergone oxidation, e.g., hydroxylation, reduction, acetylation, deamination, amination, methylation or extensive degradation. Where the metabolite still retains a substantial portion of the spatial and polar geometry of the original compound, it will be frequently possible to make the ligand analog based on either the original compound or metabolite. Where the metabolite is distinctively different than the original compound, the ligand analog will be based on the metabolite.

Of particular interest as metabolites, particularly of the steroids, are the sulfates and glucuronides.

Besides metabolites of the various drugs, hormones and other compounds previously described, of significant interest are metabolites which relate to diseased states. Illustrative of such compounds are spermine, galactose, phenylpyruvic acid and porphyrin Type 1, which are believed to be diagnostic of certain tumors, galactosemia, phenylketonuria and congenital porphyra, respectively.

Two compounds of interest which are metabolites of epinephrine are vanillylmandelic acid and homovanillic acid. With these compounds, either the hydroxyl or carboxyl groups can be used as the site for -X*.

Another general category of interest is the pesticides, e.g., insecticides, fungicides, bacteriocides and nematocides. Illustrative compounds include phosphates such as malathion, DDVP, dibrom; carbamates, such as Sevin, etc.

Since many of the biologically active materials are active in only one stereoisomeric form, it is understood that the active form is intended or the racemate, where the racemate is satisfactory and readily available. The antibodies will be specific for whatever form is used as the hapten.

Enzymes (A)

Enzymes vary widely in their substrates, cofactors, specificity, ubiquitousness, stability to temperature, pH optimum, turnover rate, and the like. Other than inherent factors, there are also the practical considerations, that some enzymes have been characterized extensively, have accurate reproducible assays developed, and are commercially available. In addition, for the purposes of this invention, the enzymes should either be capable of specific labelling or allow for efficient substitution, so as to be useful in the subject assays. By specific labelling is intended selective labelling at a site in relationship to the active site of the enzyme, so that upon binding of the receptor to the ligand, the enzyme is satisfactorily inhibited. By allowing for efficient substitution to be useful in the subject assay, it is intended that the enzyme be inhibited sufficiently when the ligand is bound to the receptor, and that the degree of substitution required to achieve this result does not unreasonably diminish the turnover rate for the enzyme nor substantially change the enzyme's solubility characteristics.

For the standpoint of operability, a very wide variety of enzymes can be used. But, as a practical matter, there will be a number of groups of enzymes which are preferred. Employing the International Union of Biochemists (I.U.B.) classification, the oxidoreductases (1.) and the hydrolases (3.) will be of greatest interest, while the lyases (4.) will be of lesser interest. Of the oxidoreductases, the ones acting on the CHOH group, the aldehyde or keto group, or the CH-NH$_2$ group as donors (1.1, 1.2, and 1.4 respectively) and those acting on hydrogen peroxide as acceptor (1.11) will be preferred. Also, among the oxidoreductases as preferable will be those which employ nicotinamide adenine dinucleotide, or its phosphate or cytochrome as an acceptor, namely 1.x.1 and 1.x.2, respectively under the I.U.B. classification. Of the hydrolases, of particular interest are those acting on glycosyl compounds, particularly glycoside hydrolases, and those acting on ester bonds, both organic and inorganic esters, namely the 3.1 and 3.2 groups respectively, under the I.U.B. classification. Other groups of enzymes which might find use are the transferases, the lyases, the isomerases, and the ligases.

In choosing an enzyme for commercialization, as compared to a single or limited use for scientific investigation, there will be a number of desireable criteria. These criteria will be considered below.

The enzyme should be stable when stored for a period of at least three months, and preferably at least six months at temperatures which are convenient to store in the laboratory, normally $-20°$ C or above.

The enzyme should have a satisfactory turnover rate at or near the pH optimum for binding to the antibody, this is normally at about pH 6 – 10, usually 6.0 to 8.0. Preferably, the enzyme will have the pH optimum for the turnover rate at or near the pH optimum for binding of the antibody to the ligand.

A product should be either formed or destroyed as a result of the enzyme reaction which absorbs light in the ultraviolet region or the visible region, that is in the range of about 250–750 nm, preferably 300–600 nm.

Preferably, the enzyme should have a substrate (including cofactors) which has a molecular weight in excess of 300, preferably in excess of 500, there being no upper limit. The substrate may either be the natural substrate, or a synthetically available substrate.

Preferably, the enzyme which is employed or other enzymes, with like activity, will not be present in the fluid to be measured, or can be easily removed or deactivated prior to the addition of the assay reagents. Also, one would want that there not be naturally occurring inhibitors for the enzyme present in fluids to be assayed.

Also, although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight limitations refer to the enzyme and not to the subunits.

For synthetic convenience, it is preferable that there be a reasonable number of groups to which the ligand may be bonded, particularly amino groups. However, other groups to which the ligand may be bonded include hydroxyl groups, thiols, and activated aromatic rings, e.g., phenolic.

Therefore, enzymes will preferably be chosen which are sufficiently characterized so as to assure the availability of sites for linking, either in positions which allow for inhibition of the enzyme when the ligand is bound to antibody, or there exist a sufficient number of positions as to make this occurrence likely.

A list of common enzymes may be found in Hawk, et al, Practical Physiological Chemistry, McGraw-Hill Book Company, New York (1954), pages 306 to 307. That list is produced in total as follows, including the source of the enzyme, the substrate and the end products.

| Name & Class | Distribution | Substrate | End-products |
|---|---|---|---|
| Hydrolases | | | |
| Carbohydrases | | Carbohydrates | |
| 1. Amylase | Pancreas, saliva, malt, etc. | Starch, dextrin, etc. | Maltose and dextrins |
| 2. Lactase | Intestinal juice and mucosa | Lactose | Glucose and galactose |
| 3. Maltase | Intestinal juice, yeast, etc. | Maltose | Glucose |
| 4. Sucrase | Intestinal juice yeast, etc. | Sucrose | Glucose and fructose |
| 5. Emulsion | Plants | $\beta$-Glucosides | Glucose, etc. |
| Nucleases | | Nucleic acid and derivatives | |
| 1. Polynucleotidase | Pancreatic juice intestinal juice etc. | Nucleic acid | Nucleotides |
| 2. Nucleotidase | Intestinal juice and other tissues | Nucleotides | Nucleotides and phosphoric acid |
| 3. Nucleotidase | Animal tissues | Nucleotides | Carbohydrate and bases |
| Amidases | | Amino compounds and amides | |
| 1. Arginase | Liver | Arginine | Ornithine and urea |
| 2. Urease | Bacteria, soybean, jack bean etc. | Urea | Carbon dioxide and ammonia |
| 3. Glutaminase | Liver, etc. | Glutamine | Glutamic acid and ammonia |
| 4. Transaminase | Animal tissues | Glutamic acid and oxalacetic acid, etc. | $\alpha$-Ketoglutaric acid, aspartic acid, etc. |
| Purine Deaminases | | Purine basesa and derivatives | |
| 1. Adenase | Animal tissues | Adenine | Hypoxanthine and ammonia |
| 2. Guanase | Animal tissues | Guanine | Xanthine and ammonia |
| Peptidases | | Peptides | |
| 1. Aminopolypeptidase | Yeast, intestines etc. | Polypeptides | Simpler peptides and amino acids |
| 2. Carboxypeptidase | Pancreas | Polypeptides | Simpler peptides and amino acids |
| 3. Dipeptidase | Plant and animal tissues and bacteria | Dipeptides | Amino acids |
| 4. Prolinase | Animal tissues and yeast | Proline peptides | Proline and simpler peptides |
| Proteinases | | Proteins | |
| 1. Pepsin | Gastric juice | Proteins | Proteoses, peptones, etc. |
| 2. Trypsin | Pancreatic juice | Proteins, proteoses, and peptones | Polypeptides and amino acid |
| 3. Cathepsin | Animal tissues | Proteins | Proteoses, and peptones |
| 4. Rennin | Calf stomach | Casein | Paracasein |
| 5. Chymotrypsin | Pancreatic juice | Proteins, proteoses and peptones | Polypeptides and amino acid |
| 6. Papain | Papaya, other plants | Proteins, proteoses, and peptones | |
| 7. Ficin | Fig sap | Proteins | Proteoses, etc. |
| Esterases | | Esters | Alcohols and acids |
| 1. Lipase | Pancreas, castor bean, etc. | Fats | Glycerol and fatty acids |
| 2. Esterases | Liver, etc. | Ethyl butyrate, etc. | Alcohols and acids |
| 3. Phosphatases | Plant and animal tissues | Esters of phosphoric acid | Phosphate and alcohol |
| 4. Sulfatases | Animal and plant tissues | Esters of sulfuric acid | Sulfuric acid and alcohol |
| 5. Cholinesterase | Blood, tissues | Acetylcholine | Choline and acetic acid |
| Iron Enzymes | | | |

-continued

| Name & Class | Distribution | Substrate | End-products |
|---|---|---|---|
| 1. Catalase | All living organisms except a few species of microorganisms | Hydrogen peroxide | Water and oxygen |
| 2. Cytochrome oxidase | All living organisms except a few species of microorganisms | Reduced cytochrome C in the presence of oxygen | Oxidized cytochrome C and water |
| 3. Peroxidase | Nearly all plant cells | A large number of phenols aromatic amines, etc. in the presence of $H_2O_2$ | Oxidation product of substrate and water |
| Copper Enzymes | | | |
| 1. Tyrosinase (poly-phenoloxidase, monophenoloxidase) | Plant and animal tissues | Various phenolic compounds | Oxidation product of substrate |
| 2. Ascorbic acid oxidase | Plant tissues | Ascorbic acid in the presence of oxygen | Dehydroascorbic acid |
| Enzymes Containing Coenzymes I and/or II | | | |
| 1. Alcohol dehydrogenase | Animal and plant tissues | Ethyl alcohol and other alcohols | Acetaldehyde and other aldehydes |
| 2. Malic dehydrogenase | Animal and plant tissues | L( ) Malic acid | Oxalacetic acid |
| 3. Isocritric dehydrogenase | Animal and plant tissues | L-Isocitric acid | Oxalosuccinic acid |
| 4. Lactic dehydrogenase | Animal tissues and yeast | Lactic acid | Pyruvic acid |
| 5. β-Hydroxybutyric dehydrogenase | Liver, kidneys, and heart | L-β-Hydroxybutyric acid | Acetoacetic acid |
| 6. Glucose dehydrogenase | Animal tissues | D-Glucose | D-Gluconic acid |
| 7. Robison ester dehydrogenase | Erythrocytes and yeast | Robison ester (hexose-6-phosphate | Phosphohexonic acid |
| 8. Glycerophosphate dehydrogenase | Animal tissues | Glycerophosphate | Phosphoglyceric acid |
| 9. Aldehyde dehydrogenase | Liver | Aldehydes | Acids |
| Enzymes which Reduce Cytochrome | | | |
| 1. Succinic dehydrogenase (as ordinarily prepared) | Plants, animals and microorganisms | Succinic acid | Fumaric acid |
| Yellow Enzymes | | | |
| 1. Warburg's old yellow enzyme | Yeast | Reduced coenzyme II | Oxidized coenzyme II and reduced yellow enzyme |
| 2. Diaphorase | Bacteria, yeasts, higher plants, and animals | Reduced coenzyme I | Oxidized coenzyme I and reduced yellow diaphorase |
| 3. Haas enzyme | Yeast | Reduced coenzyme II | Oxidized coenzyme II and reduced yellow enzyme |
| 4. Xanthine oxidase | Animal tissues | Hypoxanthine xanthine, aldehydes, reduced coenzyme I, etc. | Xanthine, uric acid, acids, oxidized coenzyme I, etc. In presence of air, $H_2O_2$ |
| 5. D-amino acid oxidase | Animal tissues | D-Amino Acids + $O_2$ | α-Keto-acids + $NH_3$ + $H_2O_2$ |
| 6. L-Amino acid oxidases | Animals, snake venoms | L-amino acids | Keto acids and ammonia |
| 7. TPN-Cytochrome C reductase | Yeast, liver | Reduced coenzyme II and cytochrome C | Oxidized coenzyme I and reduced cytochrome C |
| 8. DPN Cytochrome C reductase | Liver, yeast | Reduced coenzyme I and cytochrome C | Oxidized coenzyme I and reduced cytochrome C |
| Hydrases | | | |
| 1. Fumarase | Living organisms in general | Fumaric acid + $H_2O$ | L-Malic acid |
| 2. Aconitase | Animals and | Citric acid | cis-Aconitic |

-continued

| Name & Class | Distribution | Substrate | End-products |
|---|---|---|---|
| | plants | | acid and L-isocitric acid |
| 3. Enolase | Animal tissues and yeast | 2-Phosphoglyceric acid | Phospyruvic acid + $H_2O$ |
| Mutases | | | |
| 1. Glyoxalase | Living organisms in general | Methyl glyoxal and other substituted glyoxals | D (−) Lactic acid |
| Desmolases | | | |
| 1. Zymohexase (aldolase) | All cells | Fructose-1,6-diphosphate | Dihydroxyacetone phosphoric acid and phosphoglyceric acid |
| 2. Carboxylase | Plant tissues | Pyruvic acid | Acetaldehyde and $CO_2$ |
| 3. β-Keto carboxylases | Animals, bacteria, plants | β-Keto acids | α-Keto acids |
| 4. Amino acid decarboxylases | Plants, animals, bacteria | L-Amino acids | Amines and $CO_2$ |
| 5. Carbonic anhydrase | Erythrocytes | Carbonic acid | $CO_2 + H_2O$ |
| Other Enzymes | | | |
| 1. Phosphorylase | Animal and plant tissues | Starch or glycogen and phosphate | Glucose-1-phosphate |
| 2. Phosphohexoisomerase | Animal and plant tissues | Glucose-6-phosphate | Fructose-6-phosphate |
| 3. Hexokinase | Yeast, animal tissues | Adenosinetriphosphate | Adenosinediphosphate + glucose-6-phosphate |
| 4. Phosphoglucomutase | Plant and animals | Glucose-1-phosphate | Glucose-6-phosphate |

Of the various enzymes, the following table indicates enzymes of particular interest set forth in accordance with the I.U.B. classification.
1. Oxidoreductases
   1.1 Acting on the CH-OH group of donors
      1.1.1 With NAD or NADP as acceptor
         1. alcohol dehydrogenase
         6. glycerol dehydrogenase
         26. glyoxylate reductase
         27. L-lactate dehydrogenase
         37. malate dehydrogenase
         49. glucose 6-phosphate dehydrogenase
         17. mannitol 1-phosphate dehydrogenase
      1.1.2 With cytochrome as an acceptor
         3. L-lactate dehydrogenase
      1.1.3 With $O_2$ as acceptor
         4. glycose oxidase
         9. galactose oxidase
   1.2 Acting on the CH-$NH_2$ group of donors
   1.4.3 With $O_2$ as acceptor
         2. L-amino acid oxidase
         3. D-amino acid oxidase
   1.6 Acting on reduced NAD or NADP as donor
      1.6.99 With other acceptors
         diaphorase
   1.10 Acting on diphenols and related substances as donors
      1.10.3 With $O_2$ as acceptor
         1. polyphenol oxidase
         3. ascorbate oxidase
   1.11 Acting on $H_2O_2$ as acceptor
      1.11.1
         6. catalase
         7. peroxidase
3. Hydrolases
   3.1 Acting on ester bonds
      3.1.1 Carboxylic ester hydrolases
         7. cholinesterase
      3.1.3 Phosphoric monoester hydrolases
         1. alkaline phosphatase
      3.1.4 Phosphoric diester hydrolases
         3. phospholipase C
   3.2 Acting on glycosyl compounds
      3.2.1 Glycoside hydrolases
         1. α-amylase
         4. cellulase
         17. lysozyme
         23. β-galactosidase
         27. amyloglucosidase
         31. β-glucuronidase
   3.4 Acting on peptide bonds
      3.4.2 Peptidyl-amino acid hydrolase
         1. carboxypeptidase A
      3.4.4 Peptidyl-peptide hydrolase
         5. α-chymotrypsin
         10. papain
   3.5 Acting on C-N bonds other than peptide bonds
      3.5.1 In linear amides
         5. urease
   3.6 Acting on acid anhydride bonds
      3.6.1 In phosphoryl-containing anhydrides
         1. inorganic pyrophosphatase
4. Lyases
   4.1 Carbon-carbon lyases
      4.1.2 Aldehyde lyases
         7. aldolase
   4.2 Carbon-oxygen lyases
      4.2.1 Hydrolases
         1. carbonic anhydrase
   4.3 Carbon-nitrogen lyases
      4.3.1 Ammonia lyases
         3. histidase

Linking Group (X)

The ligand or ligand analog is normally bonded either directly to the enzyme, by a single or double bond, or preferably to a linking group. For those ligands, which are haptens, and for which the receptors are antibodies the ligand will have been bound to a protein for the purpose of preparing the antibodies. Since the antibodies will recognize that portion of the ligand molecule which extends from the protein, ordinarily the same linking group will be attached on the same site on the ligand, as was used in bonding the ligand to the protein to provide the antigenic substance.

The functional groups which will be present in the enzyme for linking are amino (including guanidino), hydroxy, carboxy, and mercapto. In addition, activated aromatic groups or imidazole may also serve as a site for linking.

Amino acids having amimo groups available for linking include lysine, arginine, and histidine. Amino acids with free hydroxyl groups include serine, hydroxyproline, tyrosine and threonine. Amino acids which have free carboxyl groups include aspartic acid and glutamic acid. An amino acid which has an available mercapto group is cysteine. Finally, the amino acids which have activated aromatic rings are tyrosine and tryptophan.

In most instances, the preferred linking group will be the amino group. However, there will be situations with certain enzymes, where one of the other linking groups will be preferred.

The ligand, of course, will have a great diversity of functionalities which may be present. In addition, as already indicated, the functionalities which are present may be modified so as to form a different functionality, e.g., keto to hydroxy or an olefin to aldehyde or carboxylic acid. To that extent, the choice of groups for linking to the ligand may be varied much more widely than the choice of groups for linking to the enzyme. In both cases, however, a wide variety of different types of functionalities have been developed, specifically for linking various compounds to proteins and particularly enzymes.

Where a linking group is employed for bonding the ligand to the enzyme, it will be the more frequent procedure to bond the linking group to the ligand to provide an active site for bonding to the enzyme. This may be achieved in a single step or may require a plurality of synthetic steps, including blocking and unblocking the active groups on the ligand, other than the one involved in providing the linking group. The linking groups which are reported hereafter are solely concerned with the bridge bonding the enzyme and the ligand.

Where a linking group is used, there will normally be from one atom to 14 atoms in the chain, more usually from two atoms to 8 atoms in the chain bonding the ligand to the enzyme. Where cyclic structures are involved, the cyclic structure will be equated to the number of atoms providing a similar length to the chain.

The linking group (excluding the atoms derived from the ligand and enzyme), when other than a direct bond is involved, will be of from about 1 to 30 atoms — carbon, hydrogen, nitrogen, oxygen, phosphorus, and sulfur — more usually 4 to 20 atoms.

Preferably, the linking group will normally be of from zero to 14 carbon atoms, usually from 1 to 8 carbon atoms and from 1 to 8 heteroatoms, and frequently of from 1 to 8 carbon atoms and from 1 to 4 heteroatoms, which are oxygen, sulfur and nitrogen, more usually oxygen and nitrogen. The most frequent heterofunctionalities present in the linking group are nonoxocarbonyl or thiocarbonyl, amino, imino (oxime or imidate) diazo, or oxy.

A group of linking groups are derived from a group having a nonoxocarbonyl functionality and when a second functionality is present, the second functionality may be based on a second nonoxocarbonyl functionality, a haloalkyl, O-substituted hydroxylamine, imino, amino or diazo. The linking group will normally have from 2 to 8 carbon atoms and from 1 to 4 heteroatoms which are usually oxygen and nitrogen (the heteroatoms of the ligand and enzyme are not included in the above range of heteroatoms). Such determination is somewhat arbitrary, so that between a carbon atom of the ligand and a carbon atom of the enzyme, there may be as many as six heteroatoms. The heteroatoms may be part of the linking group chain or branched from the chain, e.g., non-oxocarbonyl oxygen.

One group of linking groups will have from 2 to 6 carbon atoms, more usually 2 to 4 carbon atoms and be an aliphatic non-oxo carbonyl functionality. Another group of linking groups will have from 2 to 8 carbon atoms and have from 1 to 2 heteroatoms, e.g., oxygen and nitrogen, in the chain, such as amino, oximino, diazo, oxy, and the like.

The following tabulation indicates various linking groups, varying with the functionalities present on the ligand and the enzyme. Except as indicated, the linking group satisfies one to two valences on the ligand and enzyme functional groups to which it is bound.

| Ligand | Enzyme |
|---|---|
| amino ($-NH-$), or hydroxyl ($-OH$) | amino($-NH_2$), hydroxyl ($-OH$) or mercapto ($-SH$) |
| | $-\overset{O}{\underset{\|}{C}}-$ |
| | $-\overset{S}{\underset{\|}{C}}-$ |
| | $-\overset{O}{\underset{\|}{C}}-Z-\overset{O}{\underset{\|}{C}}-$ |
| | $-\overset{O}{\underset{\|}{C}}-NH-CH_2\overset{O}{\underset{\|}{C}}$ |
| | $-P(O)(OR^8)-$ |
| | $-P(O)(R^8)-$ |
| | $-\overset{O}{\underset{\|}{C}}-C(R^9)_2-$ |
| | $-\overset{O}{\underset{\|}{C}}-Z-S-$ |
| | $-C(R^9)_2C(R^9)_2-$ |
| | $-\overset{S}{\underset{\|}{C}}-Z-\overset{S}{\underset{\|}{C}}-$ |
| | $-\overset{S}{\underset{\|}{C}}-NHCH_2-\overset{S}{\underset{\|}{C}}-$ |
| (only primary amino) | $-\overset{C}{\underset{\|}{C}}-Z-S-$ |
| | $\overset{O}{\underset{\|}{\diagup}}\phantom{xx}\overset{}{\diagdown}\overset{O}{\underset{\|}{}}$ |
| | $-Z-\overset{O}{\underset{\|}{C}}-$ |
| | $-Z-\overset{S}{\underset{\|}{C}}-$ |
| | $-Z-SO_2-$ |

Z- bond, hydrocarbylene of from 1 to 10 carbon atoms, more specifically alkylene of from 1 to 6 carbon atoms, alkenylene of from 2 to 6 carbon atoms, alkynylene of from 2 to 6 carbon atoms, cycloalkylene of from 4 to 10 carbon atoms and arylene of from 6 to 10 carbon atoms; oxaalkylene of from 4 to 8 carbon atoms; and azaalkylene of from 4 to 8 carbon atoms;

$R^8$ — alkyl of from 1 to 6 carbon atoms;

$R^9$ — hydrogen or alkyl of from 1 to 3 carbon atoms;

Z or non-oxo carbonyl are preferred for bonding to hydroxyl, while non-oxo carbonyl, non-oxo thiocarbonyl and Z are preferred with amino.

| Ligand | Enzyme |
|---|---|
| oxocarbonyl ($>$C=O) | amino (—NH$_2$), hydroxyl (—OH), or mercapto (—SH) |
| =NOZ— | |
| =NOZ—CO— | |
| =NO$_2$CZCO— | |
| =CHCO— | |
| =NNHZ—CO | |
| =NNHZ—CS— | |
| =NOZCS— | |
| =NO$_2$CZCS— | |
| =CHCS— | |
| =NOZS— | |
| non-oxo carbonyl (—$\overset{O}{\underset{\|}{C}}$—) | amino (—NH$_2$), hydroxyl (—OH), or mercapto (—SH) |
| —O—Z—CO— | |
| —N(R$^9$)—Z—CO— | |
| —N(R$^9$)—Z— | |
| —O—Z— | |
| —O—Z—CS— | |
| —N(R$^9$)—Z—CS— | |
| arylamino (—Z"NH$_2$) | methine (≡CH) amino (—NH$_2$) |
| =N— | |
| amino (—NH$_2$); hydroxyl (—OH) | methine (≡CH) amino (—NH$_2$) |
| —Z"—N$_2$— | |
| —Z"—N$_2$— | |
| non-oxo carbonyl ($>$C=O) | methine (≡CH) |
| | amino (—NH$_2$) |
| —O—Z"—N$_2$— | |
| —N(R$^9$)—Z"—N$_2$— | |

Z" — arylene of from 6 to 10 carbon atoms.

Where the enzyme is to be linked through a carboxyl group of the ligand or a linking group bonded to the ligand, either esters or amides will be prepared. The ligand may be bonded to any of the linking groups wwhich are appropriate to provide a link between the ligand and the alcohol or amine group of the enzyme to form the ester of amide group respectively. When the enzyme has an activated aromatic ring, the ligand may be bonded to an aromatic diazonium salt to provide the desired bridge.

The linking group will be selected in accordance with the following considerations. The bonds formed must be stable under the conditions of the assay. When bonding the ligand through the linking group to the enzyme, the enzyme must retain at least a portion of its activity upon isolation. The enzyme must not prevent binding of the ligand to the receptor. The functionalities should permit some selectivity, so that bonding can be directed to specific groups or types of groups in both the ligands and enzymes.

A few illustrations of how linking groups may be introduced are considered worthwhile. For example, if the ligand has an amino group, the amino may be bonded to form α-bromoacetamide. This product may then be used to form a carbon nitrogen bond to an amino acid of an enzyme which has a free amine group, e.g., lysine.

If the ligand has a keto group, the carbonyl may be condensed directly with an amine group of the enzyme, or the O-carboxy methyloxime may be preapred with O-carboxymethyl hydroxylamine. A mixed anhydride, with isobutyl chloroformate is formed, which may then be used to form the carboxamide with the amino group of the lysine.

Where a carboxyl group is present in the ligand, it may be convenient to react the carboxy group to form the monoamide of phenylenediamine. The resulting compound may then be diazotized to form the diazo salt which may be coupled with tyrosine present in the enzyme.

Another way to form the linking group would be to have an alcohol of a ligand react with succinic anhydride to form the monoester. The free carboxy group can then be activated by preparing the mixed anhydride and be used for reaction with an amine in the enzyme.

With an amino group present on the ligand, this may be reacted with maleic anhydride under forcing conditions to prepare the maleimide. The maleimide may then be combined with cysteine in the enzyme to provide by a Michael's addition the 3-thiosuccinimide.

For polyfunctionalized ligands such as proteins it will usually be necessary to use special techniques to prevent the formation of enzymes coupled together which are then bonded to the ligand. Having the two or more enzymes coupled would make inhibition difficult. Techniques can be employed where one group of a bifunctional reagent can be made unreactive, while the other group reacts with the enzyme or protein ligand. The other group can then be activated to carry out the second stage of linking the protein ligand to an enzyme.

Various bifunctional reagents can be employed. For example, a functionalized diazosulfonate can be used. One of the proteins can be bonded to the functionality and then the modified protein added to the other protein and the diazosulfonate group activated with light.

While for the most part, the enzyme may be bonded to any convenient position of the ligand, either through a functionality naturally present in the ligand or one introduced synthetically, there are preferred methods of bonding the enzyme to the ligand. First, it should be recognized that the ligand of the enzyme-bound-ligand need not have any biological activity. One is primarily concerned in not disturbing the geometry and polar site relationships of a substantial portion of the ligand molecule. Where the ligand is a hapten, the enzyme will therefore normally be bonded at the same site as was employed for attachment to the protein in the preparation of the antigen. Where the ligand is an intact antigen, several sites may be employed for attachment to one or more enzyme molecules with the obvious limitation that the number of enzyme molecules must not be so great as to prevent binding to the antibody. Where the ligand has a natural receptor other than an antibody, the point(s) of attachment will also be determined primarily by the necessity to preserve strong binding to the receptor.

Furthermore, if one is attempting to assay one of a variety of molecules which are quite similar, for example steroids, but differing in their substituents at the 17 position, one would choose to mark the molecule with the enzyme at a site distant from the distinguishing functionality. Following the steroid analogy, it would frequently be preferable to bond at the 3 position, rather than at the 17 position, since the distinctive portion of the molecule is usually at the 17 position. For the most part, the 3 position is either an alcohol or a ketone, the ketone normally being associated with aliphatic unsaturation. Also, the 6 position is a useful site.

The same or similar consideration will be present with other ligands. For example, with a polypeptide, which has a natural receptor site, one would preferably bond away from the receptor site.

The number of ligands which may be bonded to the enzyme will be limited by the number of available sites for bonding to the enzyme. In most cases this will be the amino groups which are present, but as already indicated, carboxyl, hydroxyl, thiol and activated aromatic rings, e.g., phenolic, are also useful sites.

Various factors will affect the number of ligands which is optimum for a specific enzyme and a specific ligand. Of prime consideration is the number required for obtaining the desired degree of inactivation when receptor is bound to the enzyme-bound-ligand. The number required will vary with the mode of attachment and the conditions for attachment of the ligand to the enzyme. Except under special circumstances, e.g., affinity labelling, there will usually be differences in degree of inactivation, as to each site to which the receptor is bound to the enzyme through a ligand. In addition, there may be cumulative effects, with an increase in the number of receptors bound to the enzyme through ligand.

Other considerations as to the number of ligands per enzyme will be the effect of the increasing number of ligands on: solubility of the enzyme-bound-ligand; activity of the enzyme-bound-ligand in the absence of receptor; and the sensitivity of the assay. Therefore, the choice of the number of ligands bonded to the enzyme is usually empirically determined, based on the effect of varying the number of ligands on the enzyme has on the assay.

With small enzymes, e.g., lysozyme, those that have molecular weights in the range of 10,000 to 30,000 from 2 to 10 ligands can be sufficient. With larger enzymes, e.g., malate dehydrogenase, of molecular weight in the range of 30,000 to 150,000, 2 to 30 ligands can be sufficient. For malate dehydrogenase 2 to 22 ligands on the average will be employed. As few ligands as possible should be bonded to the enzyme to achieve the desired degree of inhibition. Desireably, the number of ligands per enzyme should be in the range of 1 to 20, more preferably 1 to 12.

As already indicated, because of the diversity of enzymes which can be used for the assay and the variety of functionalities in the enzyme available for attachment, and the varying activities of the functionalities for being bonded to the ligand as well as their relative position to the active site of the enzymes, different numbers of ligands will be necessary for obtaining the desired degree of inhibition, when the enzyme-bound-ligand is bonded to antibody. Furthermore, the desired degree of inhibition may vary, depending on the sensitivity required for an asssay for a particular ligand.

It is found, for the most part, that increasing the average number of ligands increases the amount of inhibition, up to a degree of substitution, where further substitution does not provide a significant increase in inhibition. Therefore, by varying the conditions for the reaction between the modified ligand (ligand and linking group) and the enzyme, varying degrees of substitution can be achieved. The time for the reaction, the mole ratio of ligand to enzyme and the like can be varied. Also, the reactive functionality on the linking group can be varied to change the number and sites for substitution. One can then empirically determine the number of ligands required for the desired degree of inhibition.

It should also be noted that in referring to inhibition of an enzyme, the substrate for the enzyme plays a role. Different degrees of inhibition may be achieved with different substrates. Thus, not only can one obtain varying degrees of inhibition by varying the number of ligands bonded to the enzyme, and the sites to which the ligands are bonded, but also, with some enzymes, by varying the substrate for the enzyme.

It is also found that with increasing substitution of the enzyme by ligand, there can be reduction in enzyme activity. The turnover number diminishes and there is a concomitant increase in the Michaelis constant. The decrease in turnover number with increasing substitution will vary with the enzyme. By employing enzymes which have a high initial activity, a loss of as much as 75 percent of initial activity can be tolerated.

(Turnover number is the number of substrate molecules transformed per unit time per enzyme molecule. Lehninger, Biochemistry, Worth Publishers, New York, 1970. Since the turnover number is reported at varying temperatures and on varying bases, e.g., weight of protein as an indication of number of enzymes or change in a spectrophotometric value as an indication of number of substrate molecules, there is at the present no simple conparison between the turnover number of different enzymes. Therefore, no minimum numerical turnover number for preferred enzymes can be given.)

Also, the ligand will be attached to the enzyme by a relatively short chain, usually of the order of 1.5 to about 20 A, more usually about 3 to 10 A.

Enzyme Assay

Turning now to a consideration of the determination of the amount of active enzyme, assaying for enzymatic activity is well established for a wide variety of enzymes. A wide diversity of media, conditions and substrates have been determined for measuring enzymatic activity. See, for example, Bergmeyer, Methods for Enzymatic Analysis, Academic Press, New York, 1965. Since there are differences, not only between assays for different enzymes, but even in the variety of assays for a particular enzyme, no general description of the assay techniques can be given.

Receptor

In the subject invention, for the most part, the receptors will be macromolecules which have sites which recognize specific structures. The recognition of the specific structures will be based on van der Waals forces, which provide a specific spatial environment which maximizes the van der Waals forces; dipole interactions, either by permanent or induced dipoles; hydrogen and ionic bonding; coordinate covalent bonding; and hydrophobic bonding. For a detailed discussion of mechanisms by which receptors bind ligands, see Goldstein, et al., Principles of Drug Action, Harper and Rowe, New York, 1968.

The macromolecules of greatest interest are proteins and nucleic acids which are found in cell membranes, blood, and other biological fluids. These compounds include enzymes, antibodies, ribonucleic acid (RNA) and deoxyribonucleic acid (DNA) and natural receptors.

The most convenient group of proteins for use in the subject invention are antibodies. These materials are conveniently used in the analysis of the category of ligands referred to as haptens. Antibodies are produced by introducing an immunogenic substance into the bloodstream of a living animal. The response to the introduction of the immunogenic substance for anitgen is the production of antibodies which act to coat the antigen and detoxify it or precipitate it from solution. The protein forms a coat which is geometrically arranged so as to have the antigen fit the spatial arrangement of the protein. This may be analogised to a lock and key. The interaction is normally reversible, in that the antigen is subject to displacement or removal by various means without destruction of the receptor site.

There are many materials which are antigens and will produce an immunogenic response by being introduced into the bloodstream of a vertebrate. However, a number of materials of interest are not antigens, but are haptens, and in that situation, an extra step in preparing the antibody is required. This method of preparing antibodies with materials other than antigens is well known and may be found in Microbiology, Hoeber Medical Division, Harper and Rowe, 1969. See also, Landsteiner, Specificity of Serological Reactions, Dover Publications, N.Y. 1962; Kabat, et al., Experimental Immunochemistry, Charles C. Thomas, Springfield, Illinois, 1967; and Williams, et al, Methods in Immunology and Immunochemistry, Vol. I, Academic Press, New York, 1967.

The material which is to be assayed is bonded to a protein by any convenient means and the modified protein introduced into the blood stream. The same type of bonding groups used with the enzyme attachment to the ligand may be employed. The antibodies which form will include groups of antibodies which are shaped to fit the foreign moiety bonded to the protein. Therefore, antibodies are obtained which are specific to the compound or moiety bonded to the protein. By careful separation techniques, the antibodies primarily concerned with the moiety in question, can be concentrated so as to provide an antibody composition which is primarily related to the specific moiety which was bonded to the protein.

To illustrate this method, para-aminobenzene arsonate is diazotized to form the diazo salt. By combining the diazo salt with rabbit globulin, the rabbit globulin may be labeled with para-azobenzene arsonate. By introducing this composition into the blood stream of an animal other than a rabbit, for example a sheep, antibodies can be formed which will have a spatial arrangement which accepts solely the azobenzene arsonate.

In addition to antibodies, there are a number of naturally occurring receptors which are specific to compounds of biological interest. Compounds for which receptors are naturally occurring include thyroxine, corticosterone, cortisone, 11-desoxycortisol, 11-hydroxyprogesterone, estrogen, insulin and angiotensin. See, for example, Vonderhaar et al, Biochem. Biophysics Acta., 176, 626 (1969). All of these ligands have been studied and reported upon in the literature in connection with studies on their binding with specific receptors.

Table I

| Ligand | Receptor for Ligand Reference | Ligand Structure |
| --- | --- | --- |
| Thyroxin | Thyroxin Binding Globulin (TBG) Thyroxin Binding Prealbum (TBA) B.E.P. Murphy, C.J.J. Pattee, J. Clin. Endocr., 24, 187 (1964) | 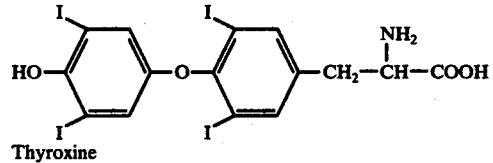 Thyroxine |
| Corticosterone | Protein From Brain Cell Nuclei, B. McEwen, L. Plapinger Nat. 226, 263 (1970) | 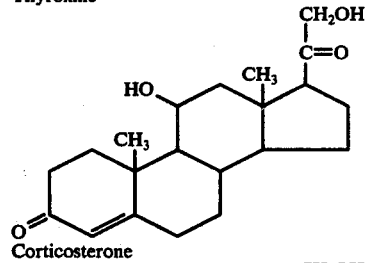 Corticosterone |
| Cortisol (R = OH,H) Cortisone (R=O) 11-desoxycortisol (R = H,H) | B.E. Murphy, J. Clin. Endocr., 28, 343 (1968), 27, 973 (1967) Corticosteroid Binding Globulin (Transcortin) | 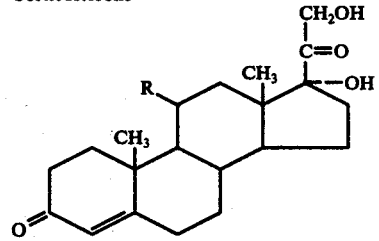 Cortisone |
| Estradiol | Receptor Site for Estrogen From Uterus, BBA, 176, 626 (1969) | 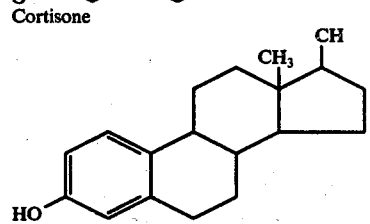 |

Table I-continued

| Ligand | Receptor for Ligand Reference | Ligand Structure |
|---|---|---|
| Insulin | C.R. Morgan, W.M. Holland, III Diabetes, 1966 | Estradiol *see below |

*H-Gly-Ile-Val-Glu-Glu-Cys-Cys-Ala-Ser-Val-Cys-Ser-Leu-Tyr-Glu-Leu-Glu-Asp-Tyr-Cys-Asp-OH with disulfide bridges (S—S) and NH$_2$ groups as shown, linked to:

H-Phe-Val-Asp-Glu-His-Leu-Cys-Gly-Ser-His-Leu-Val-Glu-Ala-Leu-Tyr--Leu--Val--Cys-Gly-Glu-Arg-Gly
  |    |
  NH$_2$ NH$_2$

...Phe-Phe-Tyr-Thr-Pro-Lys-Ala-OH

| Angiotensin II | L. B. Page, E. Haber, A. Y. Kimura A. Pernode, J. Clin. End. 28, 200 (1969) | *see below |

*Asp-Arg-Val-Tyr-Ileu-His-Pro-Phe

---

Generally, the experience obtained in bonding a specific hapten to a specific enzyme can be used in bonding other haptens to the same enzyme. This is truer the more similar the haptens. Therefore, with drugs having similar solubilities one will ordinarily expect to obtain similar results with different but similar haptens, when bonding the haptens to the enzyme with the same linking functionality. It has therefore been found synthetically convenient to employ O$^3$-carboxymethylmorphine as a prototype to evaluate a wide variety of enzymes when bonded to a carboxyl group by means of a mixed anhydride. The information thus obtained can be readily extrapolated to what one would expect from bonding other similar drugs in an analogous manner to the same enzyme.

EXPERIMENTAL

The following examples are offered by way of illustration and not by way of limitation.

(All temperatures are recorded in Centigrade).

INDEX

A. Preparation of morphine antibodies to O$^3$-carboxymethyl morphine conjugate and binding to support.
1. Morphine
1.1 O$^3$-Carboxymethyl morphine conjugate to amylase
1.2 O$^3$-Carboxymethyl morphine conjugate to horse radish peroxidase.
1.3 O$^3$-Carboxymethyl morphine conjugate to lysozyme.
1.4 O$^3$-Carboxymethyl morphine conjugate to malate dehydrogenase.
1.5 O$^3$-Carboxymethyl morphine conjugate to malate dehydrogenase with varying ratios of morphine to malate dehydrogenase.
1.6 O$^3$-Carboxymethyl morphine conjugate to lactate dehydrogenase.
1.7 O$^3$-Carboxymethyl morphine conjugate to glyoxylate reductase.
1.8 O$^3$-(α-Isopropyl)carboxymethyl morphine conjugate to malate dehydrogenase.
1.9 O$^3$-Carboxymethyl morphine conjugate to glucose 6-phosphate dehydrogenase.
1.10 O$^3$-Imidoylmethyl morphine conjugate to lysozyme.
1.11 O$^3$-Imidoylmethyl morphine conjugate to glucose 6-phosphate dehydrogenase.
2. Methadone
2.1 6-Keto-7,7,-diphenyl-9-dimethylaminodecanoic acid conjugate to lysozyme.
3. Meperidine
3.1 4-Carbethoxy-1-carboxymethyl-4-phenylpiperidine conjugate to lysozyme.
4. Amphetamine
4.1 N-Carboxymethyl amphetamine conjugate to lysozyme.
5. Barbiturates
5.1 N-Carboxymethyl phenobarbital conjugate to lysozyme.
5.2 5-(γ-Crotonic acid)-5-(2'-pentyl)-barbituric acid conjugate to lysozyme.
5.3 N-Carboxymethyl glutethimide.
5.4 N-(4-Carboxybutyl)phenobarbital conjugate to lysozyme.
5.5 5-(γ-Crotonic acid)-5-(2'-pentyl)barbituric acid conjugate to lysozyme.
6. Cocaine
6.1 Ecgonine conjugate to lysozyme.
6.2 p-Diazobenzoyl ecgonine conjugate to lysozyme.
7. Insulin
7.1 p-Diazobenzamide modified insulin conjugate to malate dehydrogenase.
8. Steroids
8.1 Testosterone-3-carboxymethyloxime conjugate to malate dehydrogenase.
8.2 3-(O-Carboxymethyl)estradiol conjugate to malate dehydrogenase.

EXAMPLE A

Preparation of Morphine Antibodies and Binding to Support

1. Morphine (900 mg.) was dried for 4 hours at 50° C., 0.01 mm. Hg. The dried morphine was dissolved in 18 ml. of abs. ethanol and 125 mg. sodium hydroxide was added, followed by the addition of 350 mg. dry sodium chloroacetate. After purging with nitrogen, the solution was stirred and refluxed for four hours. The hot solution was treated with 3.8 ml. ethanolic hydrogen chloride (0.85 M) and then filtered while still warm. On cooling overnight, a precipitate (272 mg.) formed which was collected and recrystallized from ethanol/water. On addition of ether to the original filtrate an additional precipitate was obtained which was also recrystallized from ethanol/water. Total yield 600 mg (55%). On heating this product to 75° C in vacuo there was a weight loss corresponding to 0.48 molecule of ethanol or 1.15 molecule of water. The dried compound decomposes at 190°–220° (depends on rate of heating).

Anal: $C_{19}H_{21}NO_5$; % Theor: C,66.45; H,6.16; N,4.08: % Found: C,65.87; H,6.98; N, 4.09,4.07: NMR($C_5D_5N$) 2.44 ppm (-$CH_3$), 5.08 ppm (-$CH_2$-COO).

2. Carboxymethyl morphine (240 mg) suspended in 8 ml dry dimethyl formamide (DMF) was cooled to −15° C and treated with 84 μl isobutyl chloroformate. The solid dissolved while stirring for 30 minutes at −15° C. Bovine serum albumin (BSA) (400 mg) dissolved in 56 ml water containing 2.6 g sodium bicarbonate was added to this solution and the mixture was kept at 0° C overnight. It was then dialyzed against distilled water with four changes of water (dialysis 1:80) and lyophilized to give 350 mg of conjugate.

Hapten concentration on the protein:

| $MW_{CMM} = 327$ | $\epsilon^{280}_{BSA} = 41600$ |
|---|---|
| $MW_{BSA} = 64\ 400$ | $\epsilon^{280}_{CMM} = 1070$ |

The ultraviolet spectrum was measured at 280 nm. in a 1 cm.cell; d=0.59 when the concentration was 0.287 g/l in water. The degree of conjugation can be determined from the above data and the formula:

$$d = \frac{(X\epsilon_{CMM} + \epsilon_{BSA})W}{XMW_{CMM} + MW_{BSA}}$$

where X = number of haptens per molecule, W = weight of protein conjugate per liter and MW is the molecular weight where CMM refers to the hapten carboxymethylmorphine, and BSA refers to the protein.
X = 46.6 haptens/molecule 3. Antisera may be obtained as follows: The antigen (hapten coupled to an appropriate protein, see above example) is made up in a saline solution (9 g./liter) at a 2 mg./ml. concentration. Per b 1.0 ml. aliquot of the above solution, introduced, there is introduced simultaneously 2 ml. of Complete Freund's Adjuvant in homogenized form by means of a two-way needle. For subcutaneous injections, approximately 0.3 ml. (antigen + Freund's solution) is injected per site and for intraperitoneal injections, approximately 0.4 ml. is injected. The total dosage is about 4.0 ml. per rabbit.

After 3 to 4 weeks, a booster shot is given intramuscularly consisting of 0.5 ml. of the above saline solution and 0.5 ml. of Complete Freund's Adjuvant. A period of 5 to 7 days is allowed to pass and the rabbit is bled by heart puncture.

When the desired amount of blood is collected, the blood is allowed to clot and the clot removed. The remaining solution is then centrifuged at 2,000 R.P.M. for 10 minutes. The serum is collected free of loose red cells.

An equal volume of saturated ammonium sulfate solution is added to the serum dropwise with stirring at 4° C. After standing for 1 hour at that temperature, the solution is centrifuged at 10,000 R.P.M. for 15 minutes and the supernatant removed. The residue is suspended in as small a volume as possible of 1 X BB (borate buffer, see below for description), transferred to a dialysis bag and dialyzed overnight against BB, pH 8.0. The residue in the dialysis bag is then isolated and frozen.

(To make borate buffer, dissolve 24.6 g. boric acid in water, adjust the pH with sodium hydroxide to a pH 7.9-8.0, add 0.1 g. of sodium azide and 0.01 g. of ethylmercurithiosalicylate and bring the total volume to one liter).

4. Into 20 ml. of dimethyl formamide is introduced 400 mg. aminoethyl-Bio-Gel P-300 and 300 mg. of carboxymethyl morphine (See Example A-1) and 1 g. sodium bicarbonate is added. After stirring the suspension for two days at 4° C., the suspension is filtered, the residue is washed with water until the washings are neutral, and then the residue is dried in vacuum.

The resulting product is then suspended in 20 ml. rabbit serum containing morphine antibodies and is stirred for 4 hours at 4° C. Filtration gives a residue which is resuspended in 5 ml. phthalate buffer, pH 3.8 (0.1 M) and is stirred for 2 hours. The gel is separated by centrifugation and the supernatant liquid is dialyzed against phosphate buffer, pH 7.4 (0.1 M) to give a buffered solution of substantially pure antibodies.

5. Into a flask were combined 5 ml. Sepharose 4B suspension, 5 ml. water, and 5 ml. 100 mg./ml. CNBr solution and the pH adjusted to 11.5 with 4N NaOH. While stirring the mixture, the pH was metered and maintained at 11-11.5 with 4N NaOH until no further change in pH was noted. The mixture was filtered and washed with 100 ml. of 0.1 M carbonate buffer, pH 9.0.

Morphine antibodies were pretreated by passing 3 ml. of the antibodies through a 10 X 0.9 cm. column of Sephadex G-25 equilibrated against 0.1 M carbonate, pH 9.0. The eluate was 4 ml.

Sepharose prepared above was suspended in 5 ml of carbonate buffer (cold) and added to the morphine antibody solution. the mixture was stirred for 36 hours at 4° C, filtered and washed with 100 ml of 0.1 M carbonate buffer, pH 9. Ultraviolet analysis of the washings showed 65% of the protein bonded to the Sepharose.

6. Receptor sites can be determined as follows: Enzyme activity of a solution containing enzyme-bound-ligand is determined according to normal methods. Antibody for the ligand is added until there is no further change in enzyme activity by the further addition of antibody. This determines the residual activity with substantially all of the enzyme-bound-ligand bound to antibody.

A second solution is provided of antibodies and enzyme-bound-ligand is added incrementally with the enzyme activity monitored after each addition. The enzyme activity is plotted against the amount of enzyme-bound-ligand added. In effect, antibody is being titrated with enzyme-bound-ligand. At some point, substantially all the receptor sites will be filled and one will obtain a straight-line relationship between the increase in enzyme activity and the amount of enzyme-bound-ligand added. By extrapolating the straight line portion to the abscissa, one obtains the effective number of antibody sites in inhibiting enzyme-bound-ligand. By increasing the effective number by the percent of residual activity, a close approximation of the absolute number of antibody sites is obtained.

EXAMPLE 1.1

A. To a solution of 100 mg. of amylase in 15 ml. of water containing 600 mg. of sodium bicarbonate was added $4.6 \times 10^{-2}$ M of the mixed anhydride of morphine (prepared as described in Example A.2) in 1 ml. DMF at 0°–5°. The solution was stirred at 0° for 18 hours, transferred to a dialysis bag and dialyzed against water for 2 days at 0°. The residue was lyophylized to a white solid.

The activity of the morphine modified amylase was determined as follows: Morphine modified amylase was mixed with a suspension of dyed amylose at 37°. After an arbitrary time, the reaction was quenched, centrifuged and the supernatant liquid transferred to a cuvette and the optical density measured. This was repeated a number of times so that the optical density could be plotted versus time to give a linear graph. The slope of the line indicated the enzyme activity. It was found that the modification of the amylase with morphine had little, if any, effect on the enzymatic activity of the starting amylase.

B. A measured amount of morphine antiserum (concentration of active sites equals $2 \times 10^{-7}$ M per liter) was added to a $6.4 \times 10^{-8}$ M./l carboxymethylmorphine modified amylase solution. The amylase activity test was then carried out at 37° for a total time of 20 minutes. The following table indicates the results:

| Determination | Volume of carboxymethylmorphine modified amylase, μl. | Volume of antibody solution, ml. | Optical Density |
|---|---|---|---|
| 1 | 100 | 0.0 | 0.910 |
| 2 | 100 | 0.020 | 0.720 |
| 3 | 100 | 0.050 | 0.560 |
| 4 | 100 | 0.100 | 0.450 |
| 5 | 100 | 0.150 | 0.390 |

The above table shows that with increasing concentration of antibody, there is decreasing activity of the carboxymethylmorphine modified amylase.

C. The effect of addition of codeine was determined by running one sample containing antibody and carboxymethylmorphine in the absence of codeine and one sample in the presence of codeine.

With 0.2 ml. of a solution containing antibodycarboxymethylmorphine modified enzyme complex employed in the amylase determination, the resulting optical density was 0.450. However, when 0.030 ml. of a $10^{-7}$ M of codeine solution was added to the same amount of antibody-enzyme complex, the resulting optical density in the amylase assay was 0.580. In this manner, a solution containing $10^{-7}$ M codeine could be assayed where only 30 microliters were available. This is not intended to indicate, however, that this is the minimum concentration required, but rather only that it can be successfully employed. The above method could also be used with morphine, morphine glucuronide, as well as other close structural analogs of morphine and codeine.

EXAMPLE 1.2

(1) To 10 mg ($2.5 \times 10^{-7}$ M) horseradish peroxidase (3400 I.U./mg) and 20 mg NaHCO$_3$ in 1 ml water was added 0.09 ml ($9 \times 10^{-6}$ M) of a 100 μmole/ml solution of carboxymethylmorphine mixed anhydride (see below) in dimethyl formamide (DMF) and the mixture was allowed to stand overnight at 4° C. The solution was then passed through a 1 × 10 cm column packed with Sephadex G-25 and the effluent used for peroxidase-bound-morphine in assaying for morphine.

(2) The isobutylchloroformate O$^3$-carboxymethylmorphine mixed anhydride was prepared as 100 μmole/ml DMF solution. Five mg of horseradish peroxidase (HRP) ($1.5 \times 10^{-6}$ mole of lysine residues) was dissolved in 0.5 ml of water. The solution was cooled to 4° C and the pH was adjusted to 9.5 with dilute NaOH solution. Ninety μl ($9 \times 10^{-6}$ mole) of the mixed anhydride was added in 10 μl portions while the pH was maintained at 9 - 10 by intermittent addition of NaOH. The mixture was stirred for one hour and dialyzed exhaustively against water.

EXAMPLE 1.3

A first solution (solution A) was prepared by dissolving 100 mg of lysozyme ($6.9 \times 10^{-6}$ mole) in 10 ml of water and adding sodium carbonate until a pH of 8.0 was obtained.

A second solution was prepared by suspending 34.3 mg ($1 \times 10^{-4}$ M) of carboxymethylmorphine in 2 ml of anhydrous DMF. After cooling to $-15°$ C, 13.1 μl of isobutyl chloroformate ($1 \times 10^{-4}$ M) was added to form a mixed anhydride. The solution was stirred at $-15°$ C for about 30 minutes at which time the solids had dissolved.

Solution A was cooled in an ice bath and the above morphine mixed anhydride added. After storing at 4° C for 14 hours, the solution was dialyzed against distilled water for 4 days (2,000 ml of water replaced twice daily).

The protein was lyophilized and the residue dissolved in 10 ml of 0.128M sodium phosphate, pH 7.15. The product mixture was fractionated on a weak acid cation exchange resin column (Biorex 70), eluting at a rate of 1 ml per minute with a 400 ml linear gradient ranging from 0.128 to 0.400M sodium phosphate, pH 7.15. The eluent was collected in 2 ml fractions. The chromatography was continuously monitored by measuring ultra-violet absorption at 280 nm. Five fractions were obtained. The lysozyme activity was measured according to the following technique.

A 0.35 mg/ml suspension of dried bacteria, Micrococcus lysodeikticus, in 0.05M sodium phosphate, pH 7.0 is prepared. To 2.85 ml of the suspension contained in a 3 ml cuvette is added 0.10 ml of 8.76% (W/V) (g/l.) sodium chloride solution and 0.025 ml enzyme solution ($7.5 \times 10^{-6}$ g of protein). The contents are mixed and placed in a spectrophotometer set at 436 nm at 30°. The rate of decrease of optical density with time is recorded and the rate expressed as optical density units per minute per $7.5 \times 10^{-6}$ g of protein. The following table indicates the fractions, the milligrams of protein per milliliter, and the rate of reaction.

| Fractions | mg protein/ml | rate OD/min/ $7.5 \times 10^{-6}$g protein |
|---|---|---|
| a | 0.15 | 0.027 |
| b | 0.18 | 0.033 |
| c | 0.26 | 0.040 |
| d | 0.28 | 0.047 |
| e | 0.31 | 0.043 |
| Lysozyme | 0.30 | 0.070 |

Except where otherwise indicated, the following is the procedure for assaying, when the ligand is conjugated to lysozyme. A buffer solution is prepared of Tris-Maleate, 0.025 M, pH 6.0, by dissolving 3.03 g of Tris and 2.9 g of maleic acid in 800 ml of distilled water. After adjusting the pH to 6 with 1N sodium hydroxide, the solution is diluted to a final volume of 1 liter. A 0.1 weight percent bovine serum albumin (BSA) solution in the above buffer was prepared by diluting 1 g of BSA in 1 l of the buffer. A substrate solution was prepared by suspending 30 mg of M. lysodeikticus (also referred to as M. luteus) (Miles, lyophilized) in 50 ml of the above buffer and is prepared 12 hours before use and stored at 4° in a plastic container. The stock solution of the carboxymethylmorphine conjugated to lysozyme is diluted with the BSA solution so as to obtain a reagent solution having a rate of lysis of about $0.210 \pm 0.020$ OD/min.

The active lysozyme content of the working solution is determined by measuring at 436 nm the rate of bacterial lysis at 30°. The solution is prepared by mixing 0.200 ml of bacterial solution, 0.020 ml of the BSA solution, 0.080 ml of synthetic urine, and 0.500 ml of the enzyme solution.

The antibody solution employs a 0.025 M Tris-Maleate buffer at pH 7.4 and is employed in a sufficient amount in the assay to inhibit 92 – 96% of the enzyme activity of the stock enzyme solution.

In carrying out the assay 0.2 ml of the bacterial suspension is pipetted into a flask to which is added 20 $\mu$l of the antibody solution. A urine sample is then introduced carefully, and 0.5 ml of the enzyme solution added. The reaction mixture is then aspirated into the spectrometer and the decrease in optical density measured at 436 nm for 10 seconds (any time interval from 10–60 seconds may be used) at 30°. The concentration of morphine present in the urine sample may then be determined from a standard curve.

EXAMPLE 1.4

Porcine heart malate dehydrogenase (MDH) (0.3 cc, $1 \times 10^{-7}$ moles mDH) as a 10 mg/ml suspension in 3.2 M ammonium sulfate, was centrifuged. The pellet was dissolved in 0.2 cc of water and dialyzed against 125 cc of water at 3° for 3.5 hours with one water change. The dialysate was diluted to 1 cc with a solution 0.15 M sodium phosphate and 0.075 M sodium carbonate at pH 9.0. Seventy-four $\mu$l of the mixed anhydride solution prepared as described previously was added in 5 $\mu$l increments with stirring at 0°. During the addition, the pH was maintained between 8.8 and 9.0. After the addition was complete, the solution was adjusted to pH 9.5 and stirred for 1.5 hours at room temperature. The solution was dialyzed for 24 hours against 125 ml of 0.05 M phosphate-0.05 M carbonate buffer, pH 9.3 at 3° with three buffer changes. The malate dehydrogenase was found to have about 27 morphine groups per enzyme molecule.

EXAMPLE 1.5

The following was a study concerning the effect of increasing substitution by carboxymethylmorphine with porcine heart malate dehydrogenase.

Malate dehydrogenase (4.0 ml, 40.0 mg, Calbiochem Lot 101089) was centrifuged (17,500 rpm, 20 minutes). The resulting pellet was dissolved in 1 ml of distilled water and dialyzed against 250 ml of 0.01 M phosphate buffer, pH 7.5 at 3° with 2 × 250 ml buffer changes in 4 hours. The resulting dialysate was diluted to 5 ml with 0.15 M phosphate — 0.075 M carbonate, pH 9.0, to give a solution approximately 0.1 M phosphate — 0.05 M carbonate. The solution was divided into two 2.5 ml portions.

One of the portions was cooled to approximately 0° in an ice bath, and a 0.1 M solution of radioactive $O^3$-carboxymethylmorphine ($2.43 \times 10^5$ counts per minute per $\mu$mole) was added with rapid stirring in 4 – 5 $\mu$l increments. Four aliquots of from 0.4 – 0.5 ml were withdrawn at appropriate times, the additions and withdrawals being carried out at the following schedule, while maintaining the pH of the solution between 8.8 and 9.0. The samples were withdrawn when the pH indicated reaction had occurred.

The total additions prior to each sample withdrawal were: (1) 15 $\mu$l; (2) 25 $\mu$l; (3) 19.8 $\mu$l; (4) 34 $\mu$l; (5) 41.5 $\mu$l. Five minutes after the last aliquot was added, the sample was withdrawn.

The pipettes employed to withdraw the 0.5 ml samples were each rinsed with 0.25 ml 0.05 M phosphate — 0.05 M carbonate buffer, pH 9.5. The original solutions and rinses were quantitatively transferred to dialysis sacks with proper rinsing and dialyzed for about 48 hours at 3° against the same phosphatecarbonate buffer with 5 × 250 ml buffer changes.

The samples were then quantitatively removed from the dialysis bags, using the same buffer rinses and diluted to 2 ml with the same buffer. Sample number four had a small amount of precipitate, while sample number five had a large amount of precipitate. Both samples were centrifuged, (17,500 rpm, 20 minutes). The pellet from sample four was wahsed with buffer, twice with small amounts of water, followed by an alcohol wash, and then dried in a nitrogen stream, to yield 0.2 mg. Efforts to dissolve the precipitate from sample number five were not satisfactory.

From each of the samples, a 0.5 ml aliquot was withdrawn, (the supernatant of sample four was employed) and each added to 10 ml of scintillation fluid and counted. Sample number one had a count of 11,350; sample number two 33,700, sample number three 55,200; and sample number four 80,100.

This calculates out to 3.4, 10.4, 17.3, and 27.8 morphine molecules per enzyme for the first to fourth samples. Because of the substantial insolubility of the fifth sample, no data were obtained for it.

The second sample of enzyme was treated substantially in the same manner described above to give an additional four samples of carboxymethylmorphine substituted malate dehydrogenase, labeled with 3.2, 6.1, 13.2, and 17.3 morphine.

The samples were then assayed as follows: an assay solution was prepared by combining 0.92 ml of 0.5 M phosphate buffer, 50 $\mu$l of 7 mM oxaloacetate in phosphate buffer, 20 $\mu$l of 14 mM NADH and 1 $\mu$l of $3.67 \times 10^{-5}$ in binding sites of antibody (binding sites determined by FRAT®, an ESR technique supplied by Syva Corp.) which is a large excess over the morphine present. To this solution was added 10 – 20 $\mu$l of the carboxymethylmorphine modified malate dehydrogenase, which had been diluted 1,000 fold with 1 M potassium monoacid phosphate solution.

The rate of the reaction can be followed by metering the change in optical density, at 340 nm. Approximately 30 seconds is required to mix the various reagents and the reading is then taken for the second or the third minute, depending on which gave the faster rate. Since thermodynamic equilibrium is not achieved within the time the readings are taken, the rate is changing with time. However, by repeating the same procedure before and after the addition of antibody, relative percents inhibition can be obtained for the time limit which is desirable for a commercial assay.

| Sample No. | Activity without Ab OD/min. | Activity with Ab OD/min. | % Inhibition |
|---|---|---|---|
| 1 a | 0.117 | 0.087 | 26 |
| b | 0.141 | 0.116 | 18 |
| 2 a | 0.078 | 0.039, 0.037 | 53 |
| b | 0.125 | 0.087 | 30 |
| 3 a | 0.071 | 0.017, 0.015 | 78 |
| b | 0.125 | 0.048 | 62 |
| 4 a | 0.066 | 0.008, 0.009 | 86 |
| b | 0.143 | 0.033 | 77 |

The above data demonstrate two facts for malate dehydrogenase: (1) with increasing substitution there is decreasing initial activity; and (2) with increasing substitution there is increased inhibitability for the enzyme. Therefore, when randomly substituting malate dehydrogenase, one compromises between the percent inhibition to obtain an acceptable assay and initial activity of the enzyme.

EXAMPLE 1.6

Beef heart lactate dehydrogenase (LDH) (molecular weight 142,000; 50 IU/mg) was employed as a 34 mg/ml suspension in ammonium sulfate solution. A 0.47 ml aliquot of the suspension was centrifuged and the pellet containing 8 mg of LDH was dissolved in 0.5 ml 0.01 M phosphate buffer, pH 7.5 and dialyzed, against the buffer. The dialysate solution was diluted to 20 ml with 0.15 M phosphate — 0.05 M carbonate buffer, pH 9.0 and the solution divided in half.

Each half containing 4 mg of enzyme ($5.64 \times 10^{-8}$ mole) was cooled to 4° and radioactive $O^3$-carboxymethylmorphine mixed anhydride with isobutyl carbonate (100 μmole/ml dimethyl formamide) was added. To the first sample 17 μl ($1.7 \times 10^{-6}$ mole) was employed, while with the second sample 34 μl ($3.4 \times 10^{-6}$ mole) was employed. During the reaction, the pH was maintained at 9 by addition of dilute NaOH.

After 30 minutes, the solutions were dialyzed exhaustively against 0.05 M phosphate — 0.05 carbonate solution, pH 9.3. The dialysate solutions were then diluted to 2 ml.

Scintillation counting of the samples showed that sample number 1 had an average of about one carboxymethylmorphine per enzyme molecule, and sample number two had an average of 2.5 carboxymethylmorphines per enzyme molecule.

The products were then assayed in the conventional manner employing pyruvic acid, sodium salt, and NADH. (See Worthington enzyme catalog for details.)

The results are as follows. With 3 μl of the first enzyme sample, the activity was found to be 0.141 OD/min. When 10 μl of $8.3 \times 10^{-5}$ M antibody (based on binding sites) was added, the rate was 0.110 OD/min. When, in addition to antibody, 30 μl of $3 \times 10^{-4}$ M codeine was added, the rate rose to 0.132 OD/min.

With the second sample 3 μl of the enzyme solution had an activity of 0.142 OD/min. The addition of 10 μl of $8.3 \times 10^{-5}$ M antibody reduced the rate to 0.095 OD/min. When, in addition to the antibody, 30 μl of $3 \times 10^{-4}$ M codeine, the rate rose to 0.125 OD/min.

EXAMPLE 1.7

Spinach leaf glyoxylate reductase (GR) was obtained as a suspension in ammonium sulfate (5 mg/ml) solution. An aliquot of the suspension was centrifuged and the pellet containing 5 mg of GR was dissolved in 0.5 ml 0.01 M phosphate, pH 7.5 and dialyzed against the phosphate buffer. The solution was then diluted to 2 ml with 0.15 M phosphate — 0.05 M carbonate buffer, pH 9.0 and divided in half. Each half, containing 2.5 mg of GR ($2.46 \times 10^{-8}$ mole) was cooled to 4° and radioactive $O^3$-carboxymethylmorphine mixed anhydride with isobutyl carbonate (100 μmole/ml DMF) added: to the first aliquot, 8 μl ($8 \times 10^{-7}$ mole); to the second aliquot 16 μl ($1.6 \times 10^{-6}$ mole). The pH was maintained at 9 by addition of dilute sodium hydroxide. After 30 minutes, solutions were dialyzed exhaustively against 0.05 M phosphate-0.05 M carbonate, pH 9.3. The dialysate solutions were then diluted to 2 ml.

Scintillation counting indicated 2.2 carboxymethylmorphines per enzyme in the first sample, and 5.5 carboxymethylmorphines for the second sample.

The assays were carried out in the same manner as that employed for lactate dehydrogenase. The enzyme samples were diluted ten-fold before use.

With the first sample, 5 μl had an activity of 0.098 OD/min. which diminished to 0.093 OD/min. when 10 μl of $8.3 \times 10^{-3}$ M of antibody was added. With the second sample 5 μl had an activity of 0.85 OD/min., which diminished to 0.070 OD/min. when 10 μl of antibody solution was added. When 30 μl of a $3 \times 10^{-4}$ M codeine solution was added to the mixture containing antibody, the rate was 0.075 OD/min.

EXAMPLE 1.8

A. A mixture of 9.45 g (30.2 mmoles) morphine and 1.22 g (30.2 mmoles) sodium hydroxide in 50 ml absolute ethanol was degassed and refluxed under $N_2$ until dissolution. The solvent was evaporated in vacuo and residue dried at 0.05 mm Hg for 1 hour. The residue was dissolved in 50 ml freshly distilled hexamethylphosphoramide (HMPA), 6.6 g (33.3 mmoles) of methyl α-bromo-β-methylbutyrate and 1 g sodium iodide added, the mixture degassed and heated at 65° for 4 days under $N_2$. The cooled mixture was then poured into 400 ml of ice slurry and extracted with $3 \times 100$ ml ether. The combined ethereal extracts were washed wtih 100 ml 5% aqueous sodium carbonate, 100 ml water, 50 ml saturated aqueous sodium chloride, dried over sodium carbonate, evaporated in vacuo and stored at 0.05 mm Hg for one hour. The residue was dissolved in 400 ml dry ether and hydrogen chloride added until precipitation ceased. Filtration and washing with 1 liter of dry ether yielded a white powder which was dissolved in 100 ml water and made basic with sodium carbonate solution. The resulting oil was taken up in $2 \times 200$ ml ether, dried over magnesium sulfate, evaporated in vacuo and placed on pump overnight to give 5.4 g (45%). A yellow oil cyrstallized on standing. m.p. 98°–107°.

B. The above prepared ester (450 mg, 1.2 mmoles) was refluxed in 10 ml 2 N hydrochloric acid for 3 hours. The reaction mixture was evaporated in vacuo, the vacuum maintained for 1 hour. The residue was taken up in 10 ml water and the pH adjusted to 6 with 2 N sodium hydroxide. The resulting suspension was centrifuged until clear and the supernatant decanted and washed with 20 ml of ether, 20 ml of benzene, then evaporated in vacuo and dried with a pump vacuum for 1 hour. Hot ethanol (abs.) (2 ml) was added to the residue and the resulting brown suspension was centrifuged and the supernatant decanted into 10 ml of acetone.

Filtration and washing with 10 ml of a 2:1 mixture of acetone:abs. ethanol yielded 100 mg (22%) of off-white crystals.

C. Into a reaction vessel was introduced 16.9 mg (44 μmole) of the α-isopropyl carboxymethylmorphine prepared above, 5.25 μl (40 μmoles) of isobutyl chloroformate and 1 cc of dimethyl formamide and the mixture allowed to stand for one hour at −15°.

D. A solution of 0.8 ml of 4 mg of porcine heart MDH in 0.1 M phosphate — 0.05 M carbonate buffer, pH 9, was combined with 50 μl of the above solution and the pH maintained at 9 with dilute NaOH. The mixture was stirred for one hour at 4° and diluted with sufficient 0.05M phosphate buffer, pH 7.5 to give a total volume of 5cc. The solution was then dialyzed against that buffer to provide α-isopropylcarboxymethylmorphine conjugated malate dehydrogenase.

EXAMPLE 1.9

Glucose-6-phosphate dehydrogenase (G6PDH) from Leuconostoc mesenteroides was used. A solution of 4 mg of G6PDH ($3.12 \times 10^{-8}$ mole) in 0.05 phosphate — 0.025 M carbonate buffer, pH 9.0 was treated while stirring at 4° C with 25 μl of a 50 μmole/ml DMF solution of the isobutylchloroformate mixed anhydride of O-3-carboxymethylmorphine ($^{14}$C in N-methyl). After one hour the solution was dialyzed exhaustively against 0.05 M phosphate, pH 7.5. Scintillation counting of an aliquot revealed 9.3 haptens/G6PDH incorporated.

The assay mixture was constituted as follows:

| | |
|---|---|
| 0.055 M Tris-HCl-0.033 M MgCl$_2$, pH 7.8 | 0.900 ml |
| 0.10 M NAD | 0.020 ml |
| 0.066 M Glucose-6-phosphate | 0.050 ml |
| Enzyme solution | Variable |

The reagents are mixed and the increase in absorbance at 340 nm is read in a spectrophotometer.

Data:

1. A 1/50 dilution of the stock enzyme solution in assay buffer was prepared. Ten μl gave a rate of 0.125 OD/min.
2. Addition of 3 μl of $3.7 \times 10^{-5}$ M (binding site concentration) opiate antibody prior to addition of 10 μl of enzyme gave a rate of 0.059 OD/min.
3. Addition of 30 μl of $1.67 \times 10^{-3}$ M codeine prior to addition of the reagents mentioned in 2 gave a rate of 0.125 OD/min.

EXAMPLE 1.10

A. To a solution of 5 g of morphine monohydrate in 40 ml of dry dimethyl formamide (DMF) and 300 ml of acetone, 25 g of finely powdered potassium carbonate and 5 ml of chloroacetonitrile was added. The solution was allowed to reflux for 20 hours, cooled to room temperature and filtered. The filtrate was washed three times with acetone-DMF in a 20:1 mixture and then evaporated to dryness in vacuo. Methylene chloride (500 ml) was added and the mixture heated to reflux, filtered while hot and the filtrate evaporated to give a brown oil. Addition of 200 ml of ethyl acetate led to crystallization by cooling overnight in the icebox. Total yield, 4.4 g of cyanomethylmorphine. m.p. 186°–188°.

B. To a solution of 1.0 g (3.09 mmoles) of cyanomethylmorphine in 50 ml of dry methanol was added 7 ml of a 0.0435 M sodium methoxide solution in methanol. The reaction was allowed to stir at room temperature for 48 hours. After this time, 18 μl of glacial acetic acid was added, the reaction was stirred and then evaporated to dryness. The residue was dissolved with ethylene chloride and filtered, to remove sodium acetate. After filtration, the organic phase was evaporated to give 1.2 g of a light yellow salt.

C. A solution of 18 mg (0.5 mmoles) of O$^3$-methoxyimidoylmethylmorphine in 0.5 ml of dry DMF was added dropwise to a cold (0°) solution of 60 mg of lysozyme in 6 ml of water. The aqueous solution was first adjusted to pH 7.5 with 0.05 M sodium hydroxide. The solution was then stirred at 0° overnight. The pH was adjusted to 7 and the aqueous solution was dialyzed against water for 48 hours. The resulting dialysate was suitable for enzyme immunoassay. It could be inhibited by morphine antibodies, and full recovery of activity could be achieved upon the addition of an aqueous solution of morphine.

EXAMPLE 1.11

To 4 mg of glucose 6-phosphate dehydrogenase (L. mesenteroides) in 0.05 M sodium phosphate, pH 8.5, was added 75 μl of a solution containing 73 mg of O$^3$-methoxyimidoylmethyl morphine per ml of DMF (200 μmole per ml) at 4°. The pH was maintained at 8.5 by addition of dilute HCl as needed. The reaction was allowed to proceed for 4 hours, after which the solution is exhaustively dialyzed against 0.055 M Tris HCl-0.033 M magnesium chloride, pH 7.8. The solution was diluted to 8 cc with the same buffer. The enzyme was found to contain 10.5 morphine groups per molecule.

The activity of 10 μl of a 1:50 dilution of this solution was found to 0.099 OD/min. With addition of 5 μl of an opiate antibody, $1.3 \times 10^{-4}$ M binding sites, the rate was 0.019 3OD/min. When 20 μl of $1.7 \times 10^{-3}$ M codeine was added prior to adding the antibody, the rate was 0.102 OD/min.

EXAMPLE 2.1

A. A solution of tetramethylene dibromide (32.4 g, 150 mmoles) in dry ether (150 ml) was added to magnesium (10.9 g, 450 mmoles) in ether (80 ml) at such a rate that the ether refluxed. The reaction was carried out under argon. After the addition was completed, the reaction mixture was boiled for one hour. A solution of 2,2-diphenyl-4-dimethylaminovaleronitrile (I), (prepared according to J. W. CUSIC, J. Am. Chem. Soc., 71, 3546. (1949)) (8.4 g, 30 mmoles) in dry xylene (100 ml) was added during 30 min. at room temperature, and the mixture was stirred at 55° C for 1 hour. The reaction mixture was cooled in an ice-water bath and CO$_2$ was passed through with fast stirring for four hours. Water (200 ml) and concentrated HCl (100 ml) were added, the magnesium filtered off, and the filtrate was refluxed for 2 hours. The cooled clear solution was washed with ether (3 × 150 ml) and extracted with dichloromethane (3 × 150 ml). This extract was evaporated to dryness, and the residue dissolved in 0.5 liter of 0.5 sodium hydroxide.

This solution was washed with ether (3 × 100 ml), made acidic with conc, HCl (150 ml), saturated with sodium chloride and extracted with dichloromethane (3 × 200 ml). Evaporation of the solvent left an oil (7.55 g, 60%) 6-keto-7,7-diphenyl-9-(dimethylamino)decanoic acid hydrochloride, which moves as a single spot on TLC (HCCl$_3$:MeOH 8:2 and 7:3).

| U. V. Spectrum | |
| --- | --- |
| 0.02% CF$_3$COOH | |
| | 293 ($\Sigma$ =540); |
| | 264 ($\Sigma$ =500); |
| $\lambda_{max}$ | 259 ($\Sigma$ =535); |

B. The acid, 20.1 mg (50 μmoles) was dissolved in 1 ml dry dimethylformamide, 2 drops of triethylamine were added, and the chilled solution was treated with 6.5 μl of isobutylchloroformate as described previously in other preparations.

C. Lysozyme (120 mg, 50 μmoles of lysine) was dissolved in 12 ml of water. The pH was adjusted to 10 with 0.05 N sodium hydroxide, and maintained there during the dropwise addition of the mixed anhydride solution. After 30 minutes additional stirring, the mixture was centrifuged. The supernatant fraction remained homogeneous through dialysis against water and contained the lysozyme conjugate to the methadone analog.

D. The assay employed is described in Example 1.3 for the carboxymethylmorphine lysozyme conjugate. The compositions employed were an enzyme solution at a concentration of $1.6 \times 10^{-5}$ M and an antibody solution having a concentration of $3.66 \times 10^{-5}$ M, based on binding sites, and having a binding constant of $6.55 \times 10^7$. The reagent solutions were combined to have an enzyme concentration at $2 \times 10^{-7}$, an antibody concentration based on binding sites of $2.3 \times 10^{-7}$ and a total volume including 0.080 ml of urine of 0.800 ml. Readings were taken at 40 seconds. Sensitivity to methadone was found to be $1 \times 10^{-6}$ (0.35 μg per ml).

EXAMPLE 3.1

A. 4-Cyano-4-phenylpiperidine hydrochloride (2.23 g) was dissolved in 15 ml water to which was added 4 ml of 50% aqueous potassium hydroxide. The oil was extracted with 3 × 15 ml ether and the organic layers were dried over an anhydrous magnesium sulfate. Filtration and evaporation of the solution gave a residue which was placed in a glass ampoule along with 3 ml of methanol and 1.23 ml of 50% aqueous potassium hydroxide. The sealed ampoule was heated to 165°-170° for 3.5 hours and diluted with 50 ml water. After extraction with chloroform the aqueous phase was neutralized with DOWEX 50-X8 (H+ form) to pH 6. Filtration and evaporation yielded a residue (0.82 g) which melted above 300°. Recrystallization from water and drying over phosphorous pentoxide gave a compound with m.p. 285°-286°.

B. 4-Carboxy-4-phenylpiperidine (1.8 g) was refluxed in 50 ml of 5% ethanolic hydrochloride for 4 hours. The residue on evaporation of the solvent was dissolved in acetone and the insoluble part filtered off. From the acetone solution a viscous oil remained on evaporation which crystallized on standing; m.p. 107°-110° (1.068 g). It was used without further purification.

B'. A solution of about 7.2 g of 4-cyano-4-phenylpiperidine hydrochloride in 6 ml 66% sulfuric acid was heated to 45° and stirred for 45 min. On cooling to 125° the solution became slightly more viscous. The addition of alcohol (stem of the addition funnel below the surface of the reaction mixture) lowered the temperature to 105°. It was kept there for 4 hours. During the first hour 20 ml alcohol were added, in the next hours 6 ml each. The alcohol vapors were removed by a continuous distillation. At the end of the addition the temperature was raised to 125° until condensate is no longer formed. The hot solution was poured into 6 ml water/40 g ice containing 8g sodium hydroxide. After extraction with 3 × 70 ml ether, drying over anhydrous magnesium sulfate and removal of the solvent, an oil remained which was distilled at 112°-115°/0.2 mm Hg, 4.01 g (54%).

C. 4-Carbethoxy-4-phenylpiperidine (4.01 g) was dissolved in 13 ml absolute alcohol and refluxed together with 2.01 g sodium chloroacetate. After 7 hours no starting material was present as evidenced by TLC. The precipitated sodium chloride was removed by filtration and washed with 3 ml ethanol. On cooling of the filtrate white crystals appeared. Filtration and drying gave 2.9 g (58%) of the title compound. m.p. 138°-140° C. Evaporation of the mother liquor gave a glass which did not crystallize from acetone/hexane.

D. To a solution of 29.7 mg (0.1 mmole) of 4-carbethoxy-1-carboxymethyl-4-phenylpiperidine in 1.0 ml dry dimethyl formamide at 0° was added 13.1 μl isobutyl chloroformate (0.1 mmole). The mixture was stirred at 0° for one hour.

E. The cold solution of mixed anhydride (prepared above) was added dropwise to a solution of 100 mg lysozyme (6.9 μmole) and 100 mg sodium bicarbonate in 10 ml water at 0°. The reaction was stirred at 4° for 24 hours then dialyzed against water for 48 hours. The water was changed three times a day. The partially purified enzyme conjugate was then chromatographed on Bio-Rex-70 using a 0.05-0.20M pH 7.15 phosphate buffer gradient. Lysozyme activity in the eluent was followed by the conventional lysozme assay employing Micrococcus lysodeikticus (20 mg/50 ml buffer). The addition of γ-globulin from rabbit or sheep immunized with the BSA-conjugate of the meperidine acid caused the lysozyme-meperidine conjugate to be nearly completely inhibited. Addition of free meperidine to the inhibited enzyme-antibody complex led to restoration of lysozyme activity.

EXAMPLE 4.1

A. Amphetamine sulphate (3.68 g, 20 mmoles of amine) was dissolved in 0.5 N sodium hydroxide (80 ml). The alkaline solution was extracted with ether, the ether dried and evaporated. The residue was dissolved in benzene (50 ml) and diisopropylethylamine (3 ml) was added followed by ethylbromoacetate (2.2 ml, 20 mmoles). The reaction mixture was refluxed for one hour, cooled, filtered and the filtrate evaporated. The residue was taken up in ether, washed several times with water, the ether dried and evaporated. The pure amino-ester was obtained by column chromatography on silica (hexane:ether 7:3). Yield 3.1 g (70%), NMR and IR agree with the structure.

B. The amino-ester (2.5 g, 11.3 mmoles) was dissolved in 1:1 mixture of methanol and 1N sodium hydroxide (50 ml) and left at room temperature overnight. The mixture was evaporated to a small volume, washed twice with ether (2X25 ml) and acidified to pH 6 with conc. HCl. The crystals that separated out were recrystallized from ether-acetone to give two fractions: 900 mg, m.p. - 222°-25° (m.p. lit. 220°-5° C, Tetra. Letters. 1966, 4603-7) and 450 mg, m.p. 219°-218°. Only the first fraction was used for further reactions. $\lambda_{max}^{H_2O}$ 257 nm, $\epsilon = 159$.

C. Amphetamine-carboxylic acid (700 mg, 3.8 mmoles) was suspended in dry dioxane at 50° (50 ml) and phosgene (12.5 wt.%) in benzene (20 ml) was added in one portion. The reaction mixture was stirred at 40°–50° C for 3½ hours, evaporated to dryness and redissolved in dry dioxane (20 ml). This solution was kept on ice for the next step.

D. N-carboxymethyl amphetamine (25 mg, 0.133 mmole) was suspended in 1.8 ml of dry dioxane at 40° C. Phosgene (12.5 volume percent in benzene) (0.715 ml) was added in one portion. The reaction mixture was stirred at 40° for 3½ hours before an additional 0.2 ml of phosgene (12.5 volume percent in benzene) was added. After stirring an additional 30 minutes the solution became homogeneous. The solvent was removed in vacuo at 25° in the hood. An additional 0.70 ml of dry dioxane was added for use in the next step.

E. The cold dioxane solution of the above product was added dropwise over 5 minutes to a stirred, cold (0°) solution of 200 mg sodium bicarbonate and 100 mg lysozyme in 10 ml water. The milky reaction mixture was stirred at 4° for 48 hours and then dialyzed against water (1 liter changed three times daily) for 48 hours. The residue was lyophylized and the residue used for activity and inhibition studies.

EXAMPLE 5.1

A. Sodium phenobarbital (5.08 g, 0.02 moles), methyl chloracetate, (2.16 g, 0.02 moles) methanol (14 ml) and a catalytic amount of DMF (1 ml) were refluxed for 2 hours. A white precipitate separated out during this period. The reaction mixture was cooled to room temperature and filtered. The methanolic filtrate was evaporated to dryness to yield about 5 g of a gummy material which solidified on standing. (The precipitate from the above filtration partially dissolved when rewashed with distilled water. The water-insoluble material, about 50 mg, proved to be the dialkylated product).

The solidified material was stirred with 20 ml of 1 N NaOH solution for 15 minutes and then filtered. This separated the alkali-insoluble derivatives, the monoalkylated product and unreacted phenobarbital. The alkaline filtrate was acidified with conc. HCl to a pH 2 and the white gummy precipitate which formed was taken up in methylene chloride.

Drying (MgSO$_4$) and evaporation of the organic solvent yielded 4 g of gummy material. This was dissolved in benzene and chromatographed over a column of silica gel (40 g). Elution was with chloroform and 100 ml fractions were collected. (The progress of the chromatography was followed by TLC, since the dialkylated product has an $R_f$ 0.9, the monoalkylated material $R_f$ 0.6 and phenobarbital $R_f$ 0.1 with chloroform/methanol 95:5).

Fractions 2-5 combined yielded on evaporation 1.6 g of a gum which solidified on standing. Trituration with petroleum ether and filtration yielded 1.5 g of a white powder which was shwon by NMR to be the required monoalkylated derivative, N-methoxycarbonylmethyl phenobarbital.

Further elution with chloroform (500 ml) yielded 1.5 g of a white solid which was shown to be unreacted phenobarbital.

B. The monoester prepared above (1 g) was refluxed with 10 ml of 20% HCl solution for 3.5 hours. The cooled reaction mixture was diluted with water (20 ml) and extracted with ether. Evaporation of the other extract yielded 0.98 g of a colorless gum which very slowly solidifed on standing. NMR and TLC showed that complete hydrolysis had occurred to the acid.

A pure sample of the acid was prepared by preparative TLC for UV analysis, with chloroform/methanol (5:1) as eluent. C. To a cold (0°) solution of 29.6 mg N-carboxymethyl phenobarbital (0.1 mmoles) and 14.3 μl triethyl amine (0.1 mmoles) in 1.0 ml dry dimethyl formamide was added 13.1 μl isobutyl chloroformate (0.1 mmoles). The solution was stirred at 4° for 1 hour before use.

D. The cold solution of mixed anhydride was added dropwise with stirring to a cold (4°) solution of 0.100 g lysozyme 6.9 mmole) and 0.100 g sodium bicarbonate in 10 ml water. The resulting heterogeneous solution was stored at 4° for 48 hours before being dialyzed against water for 48 hours. (The water was changed three times daily). The dialysate was then chromatographed on Bio-Rex 70 employing a 0.05–0.20 M pH 7.15 phosphate buffer gradient for elution.

E. The assay employing the phenobarbital conjugate had an enzyme concentration in the enzyme conjugate stock solution of $1.71 \times 10^{-5}$M, an antibody concentration based on binding sites in the stock solution of $1.66 \times 10^{-5}$ and a binding constant for the antibody of $5.94 \times 10^7$. The assay solution had a total volume of 0.800 ml, employed a urine volume of 0.080 ml, had an enzyme concentration of $2.14 \times 10^{-7}$ and an antibody concentration based on binding sites of $2.08 \times 10^{-7}$. The assay was carried out for 40 seconds and the sensitivity was found to be 0.3 μg/ml, the minimum detectable amount.

EXAMPLE 5.2

A. Ozone was passed through a cooled (dry ice/acetone) solution of sodium secobarbital (2.6 g, 0.01 mole) in methanol (250 ml). After ozonlysis was completed (positive KI test), nitrogen was passed through the reaction mixture to remove all traces of ozone and then dimethyl sulfide (7 ml) was added to the cold solution with a syringe and allowed to stand overnight at room temperature. After evaporation of the solvent, the residue was diluted with water (20 ml), acidified with conc. HCl and extracted with chloroform (3 × 20 ml). The chloroform extract was dried (MgSO$_4$) and evaporated to yield 2.4 g of gummy colorless material. NMR showed the presence of an aldehyde group at 89.7 ppm. This was used without further purification in the reaction with malonic acid.

B. A sample of pure aldehyde (0.24 g, 1 mmole), malonic acid (0.21 g, 2 mmoles) 20 ml pyridine and 1 ml piperidine were refluxed together for 6 hours. The solvent was removed on the flash evaporator and the residue dissolved in 10% sodium bicarbonate solution. The bicarbonate solution was washed with ether (3 × 20 ml) and then acidified with conc. HCl. Extraction with ether (2 × 20 ml) and then with chloroform (2 × 25 ml) followed by drying (MgSO$_4$) and evaporation of the combined organic layers yielded 0.23 g (80% yield) of a white solid shown by NMR to be the desired acid 5-(γ-crotonic acid)-5-(1'-methylbutyl) barbituric acid. Recrystallization from CHCl$_3$/CCl$_4$ yielded 0.16 g of pure material.

C. To a solution of 5-(α-crotonic acid)-5-(1'-methylbutyl) barbituric acid, (0.282 g, 1 mmole) in DMF (3 ml), cooled to −15° (ice-salt bath) there was added triethylamine (0.28 ml, 2 mmoles) and isobutylchloroformate (0.13 ml, 1 mmole). Stirring was continued at −15° for 15 minutes and then at 0° for 30 minutes. The reaction mixture was then added dropwise, with a syringe, to a cooled solution of BSA (400 mg) in water (56 ml) containing NaHCO$_3$ (2.6 g). The reaction mixture was stirred at 0° (cold room) for 5 days when initial trubidity had nearly all disappeared. The solution was then dialyzed against 4 1. of phosphate buffer (pH 8) followed by distilled water to yield the desired conjugate.

D. Lysozyme, 240 mg (100 μmoles of lysine) was dissolved in 20 ml of water and the solution chilled to 0° C. The solution was adjusted to pH 10.2 with 0.05 N sodium hydroxide and the mixed anhydride (100 μmoles) in 1.5 ml dry dimethyl formamide added dropwise while the solution was kept between pH 9.6 - 9.9 by addition of base as required. The pH was maintained at 9.6 for another 30 minutes, after which time the mixture was centrifuged.

The supernatant was dialyzed against 0.05 mole Tris-maleate, pH 8.0. The pellet formed by centrifugation dissolved in 20 ml 8M urea, and was dialzyed as described above, yielding additional amounts of enzyme. The urea dialysis treatment was repeated until only 10 mg of insoluble material remained.

E. An enzyme stock solution was prepared of the secobarbital conjugate to lysozyme having a concentration of enzyme of $2.08 \times 10^{-5}$ M. The antibody stock solution was $1.42 \times 10^{-5}$ M based on binding sites, and the anitbody had a binding constant of $8.4 \times 10^7$ by FRAT$^R$. In the assay solution, the enzyme concentration was $1.56 \times 10^{-7}$ M, the antibody concentration based on binding sites was $2.66 \times 10^{-7}$ M, the total assay volume was 0.800 ml, the urine volume 0.080 ml, the time for the assay 40 seconds, and the sensitivity found to 0.2 μg/ml.

EXAMPLE 5.3

Sodium hydride (0.85 g of a 50% oil paste, 18 mmoles) was added in small amounts to a stirred solution of glutethimide, (3.7 g, 17 mmoles) in dry DMF (10 ml). Stirring was continued for about 5 minutes, when gas evolution was no longer observed. Sodium chloroacetate (2.2 g) was then added and the reaction mixture was stirred with heating in an oil bath at 100° for 3 hours. After cooling, the reaction mixture was diluted with 50 ml water, acidified with conc. HCl and then poured into 200 ml ether. The ether layer was spearated and washed with water (2 × 50 ml). The organic layer was dried (MgSO$_4$) and evaporated to yield 3.4 g of a white solid. Recrystallization from carbon tetrachloride/methylene chloride yielded the analytical sample of the acid.

Anal. Calcd. for C$_{15}$H$_{17}$NO$_4$: C, 65.44; H, 6.22; N, 5.08 Found: C, 64.92; H, 6.20; N, 4.99.

The N-carboxymethyl glutethimide can be conjugated to lysozyme as set forth in the conjugation for the barbitals. Antibodies can be prepared by conjugating the N-carboxymethyl glutethimide to bovine serum albumin (BSA) and injecting the conjugated BSA into animals to obtain the appropriate antibodies. The assay is carried out in the same manner as previously described for lysozyme.

EXAMPLE 5.4

A. To a suspended solution of sodium phenobarbital (1.0 g, 3,93 mmoles) in dry dimethylformamide (12 ml) was added ethyl-5-bromovalerate (920 mg, 4.43 mmoles) with stirring, and the mixture was heated at 40° for 10 minutes to give a clear solution. The mixture was stirred at room temperature for 15 hours, and then potassium iodide (200 mg) was added to complete the reaction, which was followed by TLC (silica gel, 5% methanol — 95% chloroform). Most of the solvent was evaporated under reduced pressure to leave an oil, which was dissolved in dichloromethane (50 ml) and washed with water. The solution was shaken once with 2.5 wt.% sodium carbonate solution (25 ml) to remove unchanged starting phenobarbituric acid. The dichloromethane layer, after being washed with water and dried over anhydrous sodium sulfate, was evaporated to leave an oil (1.4 g). This oil was separated into two fractions by preparative TLC, silica gel. The oil was developed with 5% methanol - 95% chloroform, and each fraction was collected by cutting and extracted with acetone. The products, after removal of the solvent, were dissolved in dichloromethane, washed with water, and dried over anhydrous sodium sulfate. One fraction (R$_f$ 0.7) gave a colorless oil (0.5 g, 36%) which proved to be analytically pure monoalkylated compound II by IR and PMR spectra, and microanalysis:

Anal. Calcd. for C$_{19}$H$_{24}$O$_5$N$_2$: C, 63.32; H, 6.71; N, 7.77; Found; C, 63.35; H, 6.75; N, 7.86.

B. The ethyl ester prepared above (120 mg, 0.333 mmole) was dissolved into a mixture of conc. hydrochloric acid (2.5 ml) tetrahydrofuran (5 ml) and water (1 ml), and then kept at room temperature overnight. After evaporation of tetrahydrofuran under reduced pressure, the residue was diluted with saturated sodium chloride solution (10 ml) and extracted with dichloromethane. The dichloromethane layer was extracted with saturated sodium bicarbonate solution, and the combined alkaline layers, after being carefully acidified with conc. hydrochloric acid in an ice bath, were extracted with dichloromethane. The dichloromethane solution was washed with water, dried over anhydrous sodium sulfate, and evaporated to dryness to give an oily residue (100 mg, 93%), which crystallized on standing. Recrystalliztion from ether/n-hexane gave an analytical sample of the desired acid.

Anal. Calcd. for C$_{17}$H$_2$O O$_5$N$_2$: C, 61.43; H, 6.07; N, 8.43; Found: C, 61.48; H, 6.08; N, 8.43.

C. A sample of the above prepared acid was dried overnight under vacuum at 80° C before use.

In a flask protected from moisture, 166 mg of the acid was dissolved in 5 cc of dry DMF and 150 μl of triethylamine added. The solution was cooled to −15° and then 65 μl (0.5 mmole) of isobutyl chloroformate added. The mixture was stirred for one hour with the temperature maintained between −5° and 0°.

Lysozyme (1.2 g, 0.5 mmole lysine) was dissolved in 80 ml distilled water in a beaker equipped with a magnetic stirrer. The solution was cooled in an ice-water bath to 4° and the pH was adjusted to 9.5 with 0.5 M NaOH. The anhydride reaction mixture prepared above was added dropwise with stirring. The pH was kept at 9.5 - 9.7 during this addition by the slow addition of 0.5 M NaOH. The solution was stirred an additional 90 minutes at 4°.

The pH was then lowered to 8.5 by the addition of 1 M HCl and the mixture centrifuged at 12,000 rpm for 20 minutes. The supernatant fraction (S) was dialyzed against 6 changes of 0.05 M Tris buffer pH 8.0. The precipitate on being stirred briefly with 100 ml 8 M urea dissolved completely (P$_1$). Upon dialysis (as for S) a significant amount of material came out of solution. The precipitated material, separated by centrifugation, was redissolved in urea and redialyzed (P$_2$, P$_3$, P$_4$ fractions). The various fractions of soluble enzyme (P$_1$, P$_2$, P$_3$, P$_4$, etc.) were all tested for inhibition with phenobarbital antisera (equal amount of antisera was used with all fractions). The fractions $P_1$, $P_2$, $P_3$ and $P_4$ showed inhibitions of 77, 85, 86 and 92% respectively. A pool of $P_2$, $P_3$ and $P_4$ was prepared for use in the assay.

EXAMPLE 5.5

A sample of the secobarbital acid prepared as described in Example 5.2 was dried overnight under vacuum at 80° before use.

In a flask equipped with a magnetic stirrer and a drying tube was dissolved 140 mg of the above acid in 5 ml dry DMF. After the addition of 137 μl dry triethylamine the mixture was cooled to −15° and 68.5 μl of isobutyl chloroformate added. The reaction was stirred at −5° to 0° for 1 hour and then conjugated to lysozyme.

A solution of lysozyme (1.2 g, 0.5 mmole lysine) in 80 ml distilled water was cooled in an ice bath to 4° and the pH adjusted to 9.5 with 0.5 M NaOH. The acid anhydride prepared above was added dropwise with stirring as the pH was maintained at 9.5 - 9.7 by the slow addition of 0.5 M NaOH. The heterogeneous reaction mixture was allowed to stir an additional 90 minutes at 4° before the pH was lowered to 8.5 with 1 M HCl. The mixture was centrifuged at 12,000 rpm for 20 minutes. The precipitate, on being stirred with 100 ml 8 M urea dissolved completely but a significant amount of material came out of solution during dialysis (6 changes with 0.05 M tris at pH 8.0). The dialysate was centrifuged and the supernatant ($P_1$) retained. The pellet was again suspended in 8 M urea and dialyzed, and in this manner a number of soluble enzyme fractions ($P_2$, $P_3$. . . $P_n$) were obtained. The precipitate fractions were all tested for their ability to be inhibited with seconal antisera (the same amount of antisera was used for fractions). Inhibition of activity of 75, 80, 91 and 93% was obtained for fractions $P_1$, $P_2$, $P_3$ and $P_4$ respectively. The $P_1$ fraction was not considered suitable for use in the assays, but fractions $P_2$, $P_3$ and $P_4$ were all combined and used as a pool.

EXAMPLE 6.1

A. Cocaine (5 g) was refluxed in 25 ml water for 6.5 hours. The remaining oil after evaporation of the solution was dissolved in 5 ml hot water. On cooling long, white crystals separated (2.87 g). Another 543 g were obtained from the mother liquor.

B. Benzoylecgonine (1 g) was refluxed in 25 ml 2N hydrochloric acid for 1 hours. After cooling, the solution was filtered and extracted with ether. The aqueous phase was neturalized with sodium bicarbonate to pH 5.8. On evaporation a white residue remained which was refluxed with 40 ml ethanol (95%), filtered and the solvent evaporated. The oily residue (580 mg) recrystalized on addition of 0.5 ml ethanol (130 mg). m.p. 195°–197° (decomp).

C. To a suspension of 22.7 mg (0.1 mmole) ecgonine hydrochloride in 1.0 ml dry dimethyl formamide at 0° was added 13.7 μl isobutyl chloroformate (0.1 mmole). The mixture was stirred at 0° for 2 hours and then used for the conjugation.

D. To a cold (4°) solution of 100 mg lysozyme (6.9 μmole) and 100 mg sodium bicarbonate in 10 ml water was added the dimethyl formamide suspension of the mixed anhydride. The homogeneous solution was stirred at 4° for 40 hours and then dialyzed against water (1 liter changed three times daily) for 4 days. The dialyzed material was then lyophylized to dryness. Activity and inhibition studies were performed on this material.

EXAMPLE 6.2 p-Aminobenzoyl ecgonine (50 mg.) in 1 ml. of 0.2 N HCl at 0° was added dropwise to 11.3 mg. $NaNO_2$ in 1 ml. $H_2O$ at 0°. A yellow color developed. The resulting diazonium salt was added dropwise over 5 min. to a solution of 200 mg. lysozyme (Miles 6 × recryst.) in 10 ml. water at 0°, pH 9.0. A red color developed, and some precipitate appeared. The pH was maintained at 9.0 with stirring, 1.5 hrs. at 0°. The mixture was then centrifuged.

The supernatant was yellow, and the precipitate red. The precipitate was readily dissolved in 8 M urea. Both fractions were dialyzed against $H_2O$.

The supernatant fraction was recovered from the dialysis and tested for inhibition and sensitivity towards benzoyl ecgonine.

Assay

1. Antibody omitted (50 μl) Rate is 168; 171 OD/min.
2. Antibody included (1:1) Rate is 45 OD/min.
3. (2) + 0.5 μg/ml. benzoyl ecgonine Rate is 50;52 OD/min.
4. (2) + 5.0 μg/ml benzoyl ecgonine Rate is 70;75 OD/min.
5. (2) + 50 μg/ml benzoyl ecgonine Rate is 122;125 OD/min.

EXAMPLE 7.1

A. To a suspension of 4.1 g (30 mmoles) of p-aminobenzoic acid in 300 cc of water was added 4.5 cc of concentrated hydrochloric acid. The suspension was warmed slightly to hasten solution, at which time an addition of 9 cc of concentrated hydrochloric acid was added and the slution cooled to 0° - 5°. To this stirring solution was added at once a precooled solution of 2.1 g of sodium nitrite in 6 cc of water. After 15 minutes at 0° a test with starch iodide paper indicated excess nitrous acid. The pH was raised to the pH range of congo red by the addition of saturated aqueous sodium acetate. To this solution was added at once 6.3 g of sodium sulfite in 15 cc of water. A certain amount of color was produced at this step and some precipitation was observed as well. The solution could be assayed for active diazonium salt or the reactive syn isomer, (1) by touching a drop to filter paper which had been treated with β-naphthol in aqueous alcoholic carbonate solution. An instantaneous red color signaled the presence of the reactive species. After one hour at room temperature, this spot test showed no active diazonium species remaining. The aqueous solution was treated with decolorizing charcoal and filtered. The addition of solid sodium chloride to saturation caused the precipitation of the desired anti-diazosulfonate as a yellow crystalline solid which is shown by spectroscopic techniques to be the monohydrate.

B. To 500 mg of disodio para-(anti-diazosulfonato) benzoate ($1.7 \times 10^{-3}$ moles) and 10 ml of dry dimethyl formamide (DMF) cooled in an ice bath to 0° was added one ml of isobutyl chloroformate ($7.61 \times 10^{-3}$ moles) followed by 1.5 ml of triethylamine. The mixture was stirred for 4 hours at 0° followed by standing for 2 days in a cold room with stirring. Excess chloroformate and dimethylformamide were removed by rotary evaporation at 40°.

C. The supernatant resulting from slurrying 30 mg of insulin with pH 8.8 tris-barbital buffer was combined with 50 λ (6.85 × 10$^{-3}$ mmoles) of the anhydride prepared above. The mixture was stirred for 2.5 hours at 4°, at the end of which time, the solution was dialyzed against pH 8.8 tris-barbital buffer.

The above solution was then combined with 0.25 ml (10 mg/ml, 3.4 × 10$^{-5}$ mmoles) of dialyzed malate dehydrogenase (dialyzed against tris-barbital buffer, pH 8.8) and the solution irradiated with visible light (greater than 398 nm) for approximately 45 minutes. A small sample was combined with β-naphthol, the solution turning red, indicating that all the diazosulfonate had not reacted.

The resulting product was chromatographed through a column of Sephadex G-50 swelled with bicarbonate pH 8.8 buffer. Five λ of the solution had an activity when assayed for malate dehydrogenase of about .12 OD/min.

EXAMPLE 8.1

The testosterone-3-carboxymethyloxime, 36.1 mg (100 μmole), was dissolved in 1 ml of dimethylformamide containing 3 drops of triethylamine. The solution was cooled to −15° C and 13.1 μl (100 μmole) of isobutylchloroformate were added. Stirred for 1 hour at −15° to −5° C during which time the solution turned light orange.

Malate dehydrogenase, 0.5 cc of 10 mg/ml suspension in 2.8M ammonium sulfate (5 mg MDH, 6.8 × 10$^{-8}$ mole MDH, 4.4 × 10$^{-6}$ mole lysine residues) was centrifuged at 15,000 rpm for 20 min. The pellet was dissolved in 1 ml of water and the solution was dialyzed against water at 4° C for 5 hours (3 changes). The solution was brought to pH 8.5 with dilute NaOH at 4° C and 44 μl of the mixed anhydride solution (4.4 mmole mixed anhydride; corresponds to 1 hapten per lysine) was added to the stirred enzyme solution in three portions over 5 minutes. Sodium hydroxide solution was added as needed to keep the pH at 8.5. Initially the solution was turbid, but cleared during 1 hour stirring at 4° C.

The solution was exhaustively dialyzed against 0.05M phosphate buffer, pH 7.5. A small amount of sediment was removed by centrifugation.

Assay: Because of the instability of highly diluted enzyme solutions, the stock solution (5 mg/ml; 3.4 × 10$^{-5}$M) was diluted 1 to 500 just prior to each assay. The order of addition of reagents to the assay mixture was as follows: 1)antibody (when used), 2)diluted enzyme, 3)oxalacetic acid, 4)NADH. The final enzyme concentration was 2.7 × 10$^{-9}$M. The antibody concentration was not known. Sufficient antibody was used to achieve greater than 40% inhibition of the enzyme activity. This corresponded to an equivalent of 10 μl of antibody containing serum.

(1) Enzyme Alone — 0.073 OD/min. (2) Enzyme + Antibody — 0.042 OD/min. (3) Enzyme + Antibody + 50 μl 10$^{-5}$M testosterone (added first) — 0.073 OD/min.

EXAMPLE 8.2

To 33.0 mg (10$^{-4}$ mole) of 3-(O-carboxymethyl)estradiol dissolved in 1 ml of anhydrous dimethylformamide was added 2 drops of triethylamine. The solution was cooled to −15°, and 13.1 μl (10$^{-4}$ mole) of isobutylchloroformate was added. The solution was maintained at −15° for 1 hour.

The above solution (44 μl) was added to a solution of 5 mg malic dehydrogenase in 0.004 M Na$_2$HPO$_4$, pH 9 which had been cooled to 4°. During the reaction the pH was maintained at 8.5 to 9.0 by adding sodium hydroxide solution. The solution, turbid initially, cleared after 2 hours. It was dialyzed exhaustively against 0.05 M sodium phosphate, pH 7.5; then clarified by centrifugation.

Assay

The stock enzyme solution was diluted 1 to 1000 with 1M Na$_2$HPO$_4$ solution and assayed in the customary manner entailing following the oxidation of reduced nicotinamide adenine dinucleotide (NADH) in the presence of oxaloacetic acid at 340 nm, 30° C. Anti-estradiol antibodies were prepared in rabbits and the γ-globulin (4×10$^{-7}$M binding sites) fraction was used in this assay.

1. 20 μl of the enzyme solution has an activity of 0.107 OD/min.
2. Addition of 5 μl of the antibody solution reduced the activity to 0.070 OD/min.
3. Addition of a) 5 μl of antibody, and b) 20 μl of the enzyme to the assay mixture containing 20 μl of 10$^{-3}$M estradiol gave 0.106 OD/min.

Assays

To further demonstrate the utility of the subject invention and its versatility in being able to distinguish a wide range of different compounds and to quantitatively or semi-quantitatively determine the concentration of these compounds in different physiological fluids, a number of assays were carried out. In these assays, the sensitivity of the assays was determined as to minimum concentrations required for detectable levels. Also comparisons were made with a wide variety of compounds to determine whether the antibodies employed would respond to compounds other than those which were intended to be assayed. In many instances the results were checked not only by thin layer chromatography, but also by an electron spin resonance technique entitled FRAT$^R$, supplied by Syva Corp.

As previously indicated, various protocols can be employed While the order of addition is not crucial, one order is preferred, particularly where the binding of the receptor to the enzyme-bound-ligand is stronger than the binding of the receptor to the ligand.

The preferred order is to combine the unknown medium with the receptor. The binding of ligand with receptor is rapid, so that the addition of the enzyme-bound-ligand may be made promptly after combining the unknown medium and receptor, usually within a minute. After the addition of the enzyme-bound-ligand a short time interval is usually allowed to pass, and the enzymatic activity determined as the average rate over one-half to a few minutes, usually fewer than five minutes.

In some situations, e.g., low ligand concentration, it may be desirable to measure enzymatic activity at equilibrium. For measurements at equilibrium, the binding constants of the ligand and enzyme-bound-ligand should be within about one order of magnitude.

The first system to be considered is the morphine conjugate to lysozyme. Following the assay for lysozyme as previously described, cross-reactivities were carried out in order to determine which compounds other than morphine, the antibody would recognize, and would therefore provide a positive result for the assay. The following table illustrates the cross-reactivity for a number of compounds. The results show, that the antibody will recognize those compounds which have substantially the same ring structure as morphine, but would not recognize those compounds which do not have the same ring structure.

| MORPHINE CROSS-REACTIVITY | | | |
|---|---|---|---|
| Compound | Concentration $\mu$g/ml | — | % max rate |
| Codeine | 3 | $1 \times 10^{-5}$ | 90 |
|  | 0.3 | $1 \times 10^{-6}$ | 7 |
| Morphine glucuronide | 10 | $2.1 \times 10^{-5}$ | 77 |
|  | 0.3 | $6.35 \times 10^{-7}$ | 4 |
| Morphine | 3 | $1 \times 10^{-5}$ | 67 |
|  | 0.3 | $1 \times 10^{-6}$ | 5 |
| Hydromorphine | 3 | $1 \times 10^{-5}$ | 55 |
|  | 0.3 | $1 \times 10^{-6}$ | 6 |
| Thorazine | 35 | $9.9 \times 10^{-5}$ | 6 |
| Methadone | 30 | $8.7 \times 10^{-5}$ | 1 |
| Darvon | 300 | $8 \times 10^{-4}$ | 4 |
| Cocaine | 300 | $1 \times 10^{-3}$ | 2 |
| Pentazocine | 300 | $7.5 \times 10^{-4}$ | 3 |
| Phenobarbital | 300 | $1.2 \times 10^{-3}$ | 0 |

A total of 91 samples of patient urine were taken from a methadone clinic. All of the urines had been checked by thin layer chromatography, without hydrolysis, and four were found to contain morphine. Where morphine is present as the glucuronide it is not detected by the chromatographic system normally employed. The urines were then tested, both by FRAT ® and the subject enzyme assay. Of the 91 samples, both the FRAT ® and the subject enzyme assay showed the same 17 samples to be positive, which included the four positive samples found by thin layer chromatography. The amounts of morphine detected varied from a low of about 0.3 $\mu$g/ml to a high of about 14.3 $\mu$g/ml.

Morphine has also been assayed in saliva. The following reagent solutions were prepared: 0.1 M potassium phosphate buffer solution, pH 7.5, containing 100 mg per liter of disodioethylene diamine tetraacetic acid; 14 mM nicotinamide adenine dinucleotide (NADH); 7 mM oxaloacetate in potassium phosphate buffer; morphine antibody having a binding constant as determined by an electron spin resonance technique (FRAT ®, supplied by Syva Corp.) of $2.1 \times 10^7$ and at a concentration based on binding sites of $3.4 \times 10^{-5}$ M and malate dehydrogenase bound $O^3$-$\alpha$-isopropylcarboxymethylmorphine in 1 M potassium phosphate buffer containing 0.25% bovine serum albumin as a stabilizer.

The assays were carried out at 37° C and 340 nm. The level of inhibition varied with time, so that the assay is carried out for one minute of a specific period, usually after two minutes of mixing the reagents.

The saliva which is employed in the assay is prepared as follows, in order to destroy any malate dehydrogenase activity present in the saliva and reduce the viscosity of the saliva, 0.05 ml of saliva is combined with 0.5 ml of 0.036 N HCl, mixed, and the mixture allowed to stand two minutes at ambient temperature. To the mixture is then added 0.1 ml of 0.018 N NaOH, the mixture agitated and then centrifuged for 10 minutes at 12,000 G at 0°. The saliva is then ready for use in the assay.

Into a 2 ml cup is introduced 350 $\mu$l of the 0.1 M potassium phosphate buffer, 20 $\mu$l of NADH, 150 $\mu$l of the oxaloacetate, 200 $\mu$l of the treated saliva, 10 $\mu$l of the antibody solution and 20 $\mu$l of the malate dehydrogenase bound $O^3$-$\alpha$- isopropylcarboxymethylmorphine, with the measuring sampler being rinsed with 250$\mu$l of the 0.1 M potassium phosphate buffer after addition of antibody and enzyme to insure accurate transfer.

The rate in the period from the second minute to the third minute is then determined from the zero time of the introduction of the mixture into the spectrophotometer. The rate is determined by subtracting the change in optical density (OD) of the enzyme inhibited with antibody from the OD of the sample and this value divided by the value obtained by subtracting the OD of the inhibited enzyme from the OD of the uninhibited enzyme. The value for the uninhibited enzyme is an average of the first and second minute reading, where the second minute reading is employed for the rate determination of the sample.

It was found appropriate to clean the cuvette employed in the spectrophotometer with dithioerythritol after each use.

Twenty-one samples were spiked with morphine. Of the samples spiked, with $5 \times 10^{-7}$ M morphine, the results ranged from 2.8 to $5.0 \times 10^{-7}$, only 5 of the results being below $4 \times 10^{-7}$ M. When the samples were spiked with $5 \times 10^{-8}$ M, the results varied from 4.0 to $10 \times 10^{-8}$, with most of the results being between 4 and $7.5 \times 10^{-8}$.

The next ligand to be considered is methadone. The methadone lysozyme conjugate was employed in the normal assay for lysozyme. The following table indicates the results from the cross-reactivity study. The results are reported as relative reactivity to methadone at 0.5 $\mu$g/ml. That is, the relative activity is the ratio of the concentration of the drug in question to the concentration of methadone necessary to give the same optical density reading. The smaller the relative reactivity, the less reactivity the compound has in the assay. While a large number of compounds were studied, only a few compounds showed any response. The following table indicates the results.

| METHADONE CROSS-REACTIVITY | |
|---|---|
| Compound | Relative Reactivity |
| Methadone | 1 |
| Chlorpromazine | 0.011 |
| Dextromethorphan | 0.0042 |
| Dextropropoxyphone | 0.00089 |
| Phenergan | 0.0125 |

A group of 12 urines was collected from known heroin addicts. The urines were all shown to be positive morphine and negative methadone by thin layer chromatography. However, when the urines were assayed by the FRAT ® method as well as by the subject enzyme method, both of these immunoassay techniques agreed on the presence of methadone in three of the samples, as well as the positive presence of morphine in all the samples. When 100 samples were taken from a methadone clinic, there was 100% agreement between the FRAT ® method and the enzyme immunoassay method as far as positive or negative for the presence of methadone and substantially good quantitative agreement between the determinations by the two different methods.

The next drug to be considered is amphetamine. Again, the same procedure is employed for lysozyme as for the prior assays, except that 50 $\mu$l of urine is employed. The relative reactivity is related to 1 $\mu$g/ml amphetamine.

provided in the following table for the reagents of Examples 5.1 and 5.2.

| Compound | BARBITAL CROSS-REACTIVITY | | | | | |
|---|---|---|---|---|---|---|
| | Concentration | | Phenobarbital | Concentration | | Secobarbital |
| | µg/ml | M × $10^5$ | % Max Rate | µg/ml | M × $10^5$ | % Max Rate |
| Phenobarbital | 2.54 | 1 | 42.4 | 2.54 | 1 | 0 |
| | 0.254 | 0.1 | 10.0 | 0.25 | 0.1 | 0 |
| Secobarbital | 13 | 5 | 16.7 | 2.6 | 1 | 30.1 |
| | 1.3 | .5 | 9.9 | 0.26 | 0.1 | 3.3 |
| Amobarbital | 2.5 | 1 | 16.7 | 2.48 | 1 | 16.3 |
| | 0.25 | .1 | 6.1 | 0.25 | 0.1 | 3.3 |
| Tabutal | 3 | 1.34 | 12.4 | 3 | 1.34 | 9.1 |
| | 0.3 | .13 | 3.9 | 0.3 | 0.13 | 1.4 |
| Thiopental | 3 | 1.13 | 15.8 | 3 | 1.13 | 16.0 |
| | 0.3 | .11 | 4.8 | 0.3 | 0.11 | 1.4 |
| Glutethimide | 21.7 | 10 | 9.0 | 21.7 | 10 | 0.8 |
| | 2.17 | 1 | 1.4 | | | |
| Morphine | 285 | 100 | 2.2 | 285 | 100 | 2.8 |
| Demerol | 284 | 100 | 0 | 284 | 100 | 2.1 |
| Diphenyl hydantoin | 300 | 100 | 18.4 | 300 | 100 | 7.7 |

| AMPHETAMINE CROSS-REACTIVITY | |
|---|---|
| Compoound | Relative Reactivity |
| Amphetamine | 1 |
| Methamphetamine | 1.1 |
| Mephentermine, phentermine | 0.62 |
| Propylhexedrine | 0.05 |
| Phenethylamine | 0.2 |
| Cyclopentamine | 0.33 |
| Ephedrine | 0.22 |
| Phenylpropanolamine | 0.33 |
| Nylidrin | 0.27 |
| Isoxsuprine | 0.2 |
| p-Hydroxyamphetamine | 0.022 |

A series of urine samples were obtained which were verified to contain amphetamine by gas-liquid chromatography. The samples were then assayed by both the FRAT ® assay and the subject enzyme assay. Excellent quantitative agreement was obtained between the FRAT ® assay and the subject amphetamine assay.

It is found that phenylpropanolamine which has a relatively high relative reactivity is available in over-the-counter prescriptions. In order to avoid false positives, when a positive result is obtained from a urine, the urine is treated with sodium periodate and tetramethyl ammonium hydroxide for a few minutes at ambient temperatures. The pH of the urine should be in the range of about 8 to 9. This treatment is effective in removing phenylpropanolamine as an interferant. The other compounds which cross-react are not of a sufficient occurrence to be of substantial concern.

The next system is the barbiturate system. The cross-reactivity for phenobarbital and secobarbital assays are Comparison of results of the subject enzyme assay with results obtained from thin layer chromatography were in agreement with one exception as to the presence or absence of barbiturates. By using the two different antibodies for the two barbiturates, a qualitative judgment could be made of the class of barbiturates present.

A barbiturate assay was carried out by combining antibodies to phenobarbital and secobarbital and the lysozyme conjugate prepared as described in Examples 5.4 and 5.5. The phenobarbital-lysozyme conjugate (11 µl, 1.066 × $10^{-5}$M) was combined with 4.65 µl (1.89 × $10^{-5}$M) of the secobarbital-lysozyme conjugate, 5 µl of 1% BSA in pH 6.0 tris-maleate 0.025 M buffer and 29.35 µl of pH 5.0 tris-maleate 0.025 M buffer to provide 50 µl of reagent with a maximum rate of ≈ 300 OD/min. (enzyme units). The antibody solution was prepared by combining 22.8 µl of phenobarbital antibody (1.03 × $10^{-5}$M based on binding sites) with 15.4 µl of secobarbital antibody (1.14 × $10^{-5}$M based on binding sites) and 11.8 µl of pH 7.4 tris- maleate 0.025 M buffer.

The assay for lysozyme was carried out in the conventional manner, employing 50 µl of urine.

A group of 21 barbiturate positive urine samples were collected and analyzed by thin layer chromatography (TLC), gas-liquid chromatography (GLC), FRAT ® and the subject enzyme assay technique. The following table indicates the results.

TABLE

| Sample | Independent Laboratory | TLC | GLC µg/ml | PRAT ® µg/ml | Enzyme Assay µg/ml |
|---|---|---|---|---|---|
| 1 | pentobarbital unidentified barb methadone | pentobarbital | pentobarbital (3.5) | 15 | 5.8 |
| 2 | phenobarbital methadone | phenobarbital | phenobarbital (1.0) butabarbital (2.0) | 1.6 | 2.15 |
| 3* | phenobarbital methadone | phenobarbital | phenobarbital (15.0) | 9.0 | 4.7 |
| 4 | unidentified barb methadone | pento or amobarbital | amobarbital (2.5) | 22 | 7.1 |
| 5 | pentobarbital methadone | amo, pento or butabarbital | pentobarbital (6.5) secobarbital | 31 | >100 |
| 6* | phenobarbital methadone | phenobarbital | phenobarbital (12) | 8 | 1.1 |
| 7* | phenobarbital | phenobar- | phenobarbi- | 9 | 0.8 |

TABLE-continued

| Sample | Independent Laboratory | TLC | GLC μg/ml | PRAT ® μg/ml | Enzyme Assay μg/ml |
|---|---|---|---|---|---|
| | tal methadone | bital | tal (14) | | |
| 8 | phenobarbital morphine methadone | phenobarbital | phenobarbital (4) | 2.9 | 2.2 |
| 9 | phenobarbital | pheno, amo, buta or pentobarbital | phenobarbital (32) | 140 | 64 |
| 10 | pentobarbital phenobarbital unident. narc. | amo, buta, or phenobarbital | amobarbital (<.2) phenobarbital (12) | 24 | 32.5 |
| 11 | phenobarbital methadone | phenobarbital | phenobarbital (0.7) | 2.4 | 1.1 |
| 12 | secobarbital methadone | pentobarbital | phenobarbital (0.3) secobarbital (1.7) | 11 | 5.9 |
| 13 | phenobarbital methadone amphetamine | phenobarbital | phenobarbital (1.5) amobarbital (<.2) | 3.7 | 3.0 |
| 14 | phenobarbital methadone | phenobarbital | phenobarbital (2.5) | 2.2 | 1.2 |
| 15 | phenobarbital methadone | phenobarbital | phenobarbital (1.8) | 3.7 | 1.7 |
| 16 | pentobarbital methadone | amobarbital butabarbital | amobarbital (1) | 23.0 | 40.0 |
| 17 | pentobarbital methadone | amobarbital pentobarbital | amobarbital (1.8) secobarbital (0.9) | 14.0 | 8.8 |
| 18 | unidentified barb methadone | phenobarbital | phenobarbital (1.7) | 1.9 | 1.55 |
| 19 | phenobarbital methadone | phenobarbital | phenobarbital (14.0) pentobarbital (<.4) | 17.0 | 5.3 |
| 20 | phenobarbital methadone | phenobarbital | phenobarbital (0.7) | 9.4 | 2.4 |
| 21 | pentobarbital methadone | pentobarbital | pentobarbital (0.1) | 0.5 (negative) | negative |

*These samples were all basic (pH 8 - 9.5) after standing at room temperature with no preservative for up to two months. The enzyme assay barbiturate levels were obtained after the pH of these samples was adjusted to pH ≃6.0.

The results show the excellent qualitative and quantitative correlation between the various methods. The combined enzyme assay is sensitive to 0.5 μg/ml of secobarbital with somewhat less sensitivity to other barbiturates. As expected, the enzyme assay will be most sensitive for the barbiturates to which the antibodies were prepared.

In accordance with the invention, concentrations required for assaying of a wide variety of ligands are of the order of $10^{-7}$ M or less with samples of 50 μl or less of unknown. With extremely small amounts of reagents, a very high degree of sensitivity is obtained. Furthermore, the excellent specificity of the receptor sites to a particular compound or its close analogs permits a wide range of assay possibilities with a high degree of sensitivity and specificity to particular compounds. Therefore, extremely minor amounts of biologically active materials may be assayed in the various body fluids, such as blood, saliva or urine.

The subject invention provides an extraordinarily sensitive probe for the assaying of extremely minute amounts of specific materials with a high degree of specificity and accuracy. Alternatively, the method can be used qualitatively to determine the presence or absence of particular materials with a high degree of specificity.

Much technology for enzyme assays has already been developed. Enzyme assays are well known: the optimum conditions for the assay, the substrates, and methods for detecting enzymatic activity are amply developed in the literature. Furthermore, much of the work involved in radioimmunoassay is directly applicable to the subject invention. The antisera available for radioimmunoassay are substantially applicable to ligands employed in the subject invention.

Methods for bonding compounds to enzymes at other than the active site are also well developed. There is ample literature on the functionalities which can be employed in bonding a particular compound to a particular site or amino acid in an enzyme, without substantially affecting the activity of the enzyme. The above examples demonstrate that the presence of an antibody when bound to a ligand which is bound to an enzyme can significantly reduce the activity of the enzyme. This is done either sterically or by altering the conformation of the enzyme. Furthermore, the enzymatic activity is substantially regenerated by introducing a ligand into the medium which can effectively displace the ligand bound to the enzyme, thus freeing the enzyme from the antibody.

By having an enzyme bound to a ligand, for each ligand that displaces an enzyme-bound-ligand from its receptor, a large number of substrate molecules will react and the concentration of the remaining substrate or the product can be measured. Thus, a significant amplification results (by coupling the enzyme to a ligand) because many molecules are modified by virtue of the presence of a single molecule.

The subject invention permits assays of compounds which are present in extremely low concentrations or absolute amounts. First, because receptors are available having high specificity, one or a group of compounds can be determined without significant interference from other compounds. By virtue of having one or more enzymes present in relation to a specific ligand, one can obtain a large change in concentration of the enzyme substrate based on a single ligand. In addition, the use of enzymes provides a great versatility in the detection system which is employed.

Although the foregoing invention has been described in some detail by way of illustration and example by purposes of clarity of understanding, it will be obvious that certain changes and modifications may be practiced within the scope of the invention, as limited only by the scope of the appended claims.

What is claimed is:

1. An enzyme-bound-ligand of the formula:

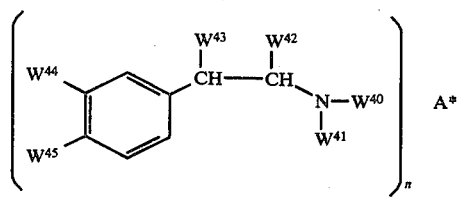

wherein:
any one of the W groups other than $W^{44}$ and $W^{45}$ can be $-X^*$ or an H of any of the W groups other than $W^{44}$ or $W^{45}$ may be replaced by $-X^*$, wherein $-X^*$ is a bond or a linking group;

$A^*$ is an enzyme bonded at other than its reactive site, having $n$ ligands, wherein $n$ is in the range of 1 to the molecular weight of $-A^*$ divided by 2,000;

$W^{40}$ and $W^{41}$ are hydrogen or alkyl of from 1 to 3 carbon atoms;

$W^{42}$ is hydrogen, alkyl of from 1 to 3 carbon atoms, or may be taken together with $W^{40}$ to form a ring having 6 annular members with a nitrogen as the only heteroatom;

$W^{43}$ is hydrogen, hydroxyl, carbomethoxy, or may be taken together with $W^{40}$ to form a morpholine ring, with the proviso that $W^{43}$ is carbomethoxy, when $W^{40}$ and $W^{42}$ are taken together; and $W^{44}$ and $W^{45}$ are hydrogen, hydroxyl, or alkoxyl of from 1 to 3 carbon atoms.

2. An enzyme-bound-ligand of the formula:

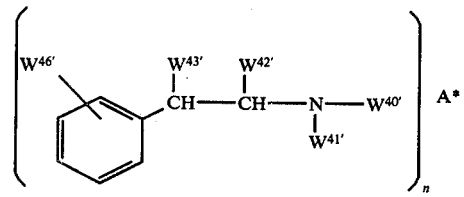

wherein:
any one of the W groups other than $W^{46'}$ can be $-X^*$ or an H of any of the W groups other than $W^{46'}$ may be replaced by $-X^*$, wherein $-X^*$ is a bond or a linking group;

$A^*$ is an enzyme bonded at other than its reactive site, having $n$ ligands wherein $n$ is in the range of 1 to the molecular weight of $A^*$ divided by 2,000;

$W^{40'}$ and $W^{41'}$ are hydrogen or alkyl of from 1 to 3 carbon atoms;

$W^{42'}$ is hydrogen, methyl, or may be taken together with $W^{40'}$ to form a piperidine ring;

$W^{43'}$ is hydrogen, hydroxyl, or carbomethoxy with the proviso that $W^{43'}$ is carbomethoxy when $W^{42'}$ is taken together with $W^{40'}$; and $W^{46'}$ is hydrogen.

3. An enzyme-bound-ligand of the formula:

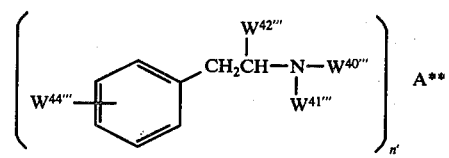

wherein:
one of $W^{40'''}$, and $W^{42'''}$ is $-X^{**}$;
when other than $-X^{**}$,
$W^{40'''}$ is hydrogen;
$W^{42'''}$ is methyl; and
$W^{44'''}$ is hydrogen;
$W^{41'''}$ is hydrogen or methyl;
$X^{}$ is $-Z-C=O$ wherein Z is hydrocarbylene of from 1 to 7 carbon atoms, with the proviso that when $W^{44'''}$ is $-X^{}$, $-X^{**}$ is

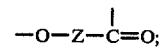

and
$A^{**}$ is an enzyme having $n'$ ligands, wherein $n'$ is in the range of 1 to 20, and said enzyme has a molecular weight in the range of 10,000 to 300,000.

4. An enzyme-bound-ligand according to claim 3, wherein said enzyme is an oxidoreductase.

5. An enzyme-bound-ligand according to claim 3, wherein said enzyme is a hydrolase.

6. An enzyme-bound-ligand according to claim 3, which is N-carboxymethylamphetamine conjugate to lysozyme, having from 2 to 4 of said amphetamine groups.

7. An enzyme-bound-ligand according to claim 3, which is N-carboxymethylamphetamine conjugate to malate dehydrogenase, having from 2 to 22 of said amphetamine groups.

8. An enzyme-bound-ligand according to claim 3, which is N-carboxymethylamphetamine conjugate to glucose 6-phosphate dehydrogenase, having from 2 to 22 of said amphetamine groups.

* * * * *